US010293498B2

(12) United States Patent
Lohmeier et al.

(10) Patent No.: US 10,293,498 B2
(45) Date of Patent: May 21, 2019

(54) SURGICAL ROBOT SYSTEM

(71) Applicant: KUKA Deutschland GmbH, Augsburg (DE)

(72) Inventors: Sebastian Lohmeier, Munich (DE); Cuong Nguyen-Xuan, Waldkirch (DE); Wolfgang Schober, Pottmes (DE)

(73) Assignee: KUKA Deutschland GmbH, Augsburg (DE)

( * ) Notice: Subject to any disclaimer, the term of this patent is extended or adjusted under 35 U.S.C. 154(b) by 291 days.

(21) Appl. No.: 14/523,353

(22) Filed: Oct. 24, 2014

(65) Prior Publication Data
US 2015/0150638 A1    Jun. 4, 2015

Related U.S. Application Data

(63) Continuation of application No. PCT/EP2013/001252, filed on Apr. 25, 2013.

(30) Foreign Application Priority Data

Apr. 27, 2012  (DE) .................. 10 2012 008 535
Aug. 6, 2012   (DE) .................. 10 2012 015 541
Sep. 18, 2012  (DE) .................. 10 2012 018 432

(51) Int. Cl.
*A61B 34/30*       (2016.01)
*B25J 19/00*       (2006.01)
(Continued)

(52) U.S. Cl.
CPC .......... *B25J 19/0075* (2013.01); *A61B 34/30* (2016.02); *A61B 90/40* (2016.02); *A61B 90/90* (2016.02);
(Continued)

(58) Field of Classification Search
CPC ......... A61B 34/30; A61B 50/30; A61B 90/40; A61B 90/90; A61B 90/98;
(Continued)

(56) References Cited

U.S. PATENT DOCUMENTS 5,784,890 A * 7/1998 Polkinghorne ......... F25B 21/02
165/104.12
6,223,794 B1 * 5/2001 Jones .................. B23Q 11/005
144/135.2
(Continued)

FOREIGN PATENT DOCUMENTS

CH          697260 B1     7/2008
CN         101443162 A    5/2009
(Continued)

OTHER PUBLICATIONS

European Patent Office; Invitation to Pay Additional Fees in International Patent Application No. PCT/EP2013/001252 dated Jul. 24, 2013; 6 pages.
(Continued)

*Primary Examiner* — Gary Jackson
*Assistant Examiner* — Zahed Kabir
(74) *Attorney, Agent, or Firm* — Dorton & Willis, LLP

(57) ABSTRACT

A robotic surgery system includes a robot assembly comprising at least one robot and an instrument assembly comprising at least one instrument that is guided by the robot assembly. The instrument assembly includes at least one instrument housing having at least one drive unit housing part containing a cavity designed to hold the drive unit. The drive unit housing part includes a seal for the sterile sealing of an insertion opening of the cavity in addition to a dynamic sterile barrier which delimits the cavity in a sterile manner and across which the drive train arrangement can be actuated. The drive unit is offset laterally in relation to a
(Continued)

longitudinal axis of the instrument shaft towards a connection between the instrument housing and the robot assembly.

18 Claims, 24 Drawing Sheets

(51) Int. Cl.
    *A61B 17/00*     (2006.01)
    *A61B 90/40*     (2016.01)
    *A61B 90/90*     (2016.01)
    *A61B 50/30*     (2016.01)
    *A61B 90/98*     (2016.01)
    *A61B 90/00*     (2016.01)

(52) U.S. Cl.
    CPC .............. *A61B 50/30* (2016.02); *A61B 90/98* (2016.02); *A61B 2017/00464* (2013.01); *A61B 2017/00477* (2013.01); *A61B 2017/00526* (2013.01); *A61B 2034/301* (2016.02); *A61B 2034/305* (2016.02); *A61B 2090/0811* (2016.02); *A61B 2090/0813* (2016.02)

(58) Field of Classification Search
    CPC .... A61B 2090/0813; A61B 2090/0811; A61B 2017/00464; A61B 2017/00477; A61B 2017/00526; A61B 2034/301; A61B 2034/305; A61B 19/2203; B25J 19/0075
    USPC .......................................... 606/1; 901/30, 36
    See application file for complete search history.

(56) References Cited

U.S. PATENT DOCUMENTS

| | | | |
|---|---|---|---|
| 7,972,298 B2* | 7/2011 | Wallace | A61B 34/20 600/114 |
| 2005/0096661 A1 | 5/2005 | Farrow et al. | |
| 2005/0228440 A1 | 10/2005 | Brock et al. | |
| 2006/0074415 A1* | 4/2006 | Scott | A61B 18/1445 606/45 |
| 2007/0137371 A1* | 6/2007 | Devengenzo | B25J 15/04 74/490.01 |
| 2007/0299427 A1* | 12/2007 | Yeung | B25J 9/047 606/1 |
| 2009/0024142 A1* | 1/2009 | Ruiz Morales | B25J 9/041 606/130 |
| 2009/0030428 A1 | 1/2009 | Omori et al. | |
| 2009/0247942 A1* | 10/2009 | Kirschenman | A61M 25/0147 604/95.04 |
| 2009/0248039 A1* | 10/2009 | Cooper | A61B 46/10 606/130 |
| 2009/0326324 A1 | 12/2009 | Munoz Martinez et al. | |
| 2010/0130986 A1* | 5/2010 | Mailloux | A61B 19/2203 606/130 |
| 2010/0175701 A1* | 7/2010 | Reis | A61B 19/081 128/852 |
| 2010/0268249 A1 | 10/2010 | Stuart | |
| 2010/0274087 A1 | 10/2010 | Diolaiti et al. | |
| 2011/0118756 A1 | 5/2011 | Brock | |
| 2011/0245833 A1 | 10/2011 | Anderson | |
| 2011/0277775 A1 | 11/2011 | Holop et al. | |
| 2012/0043100 A1* | 2/2012 | Isobe | A61B 17/1631 173/42 |
| 2012/0071894 A1* | 3/2012 | Tanner | A61B 6/12 606/130 |
| 2012/0115005 A1* | 5/2012 | Stulen | A61B 17/00234 429/120 |
| 2012/0115007 A1* | 5/2012 | Felder | A61B 17/00234 429/121 |

FOREIGN PATENT DOCUMENTS

| | | |
|---|---|---|
| CN | 101500470 A | 8/2009 |
| CN | 101866396 A | 10/2010 |
| CN | 102208835 A | 10/2011 |
| CN | 102256550 A | 11/2011 |
| DE | 102006058867 A1 | 6/2008 |
| DE | 102010040415 A1 | 3/2012 |
| DE | 102011105748 A1 | 12/2012 |
| DE | 10 2012 008 535 A1 | 10/2013 |
| DE | 10 2012 008 537 A1 | 10/2013 |
| EP | 1015068 A1 | 7/2000 |
| EP | 1946706 A1 | 7/2008 |
| EP | 2340611 A1 | 7/2011 |
| EP | 2396796 A1 | 12/2011 |
| EP | 2428337 A1 | 3/2012 |
| EP | 2578177 A2 | 4/2013 |
| JP | 2009045428 A | 3/2009 |
| WO | 2009061915 A2 | 5/2009 |
| WO | 2009123925 A1 | 10/2009 |
| WO | 2010036980 A1 | 4/2010 |
| WO | 2010/050771 A2 | 5/2010 |
| WO | 2010093997 A1 | 8/2010 |
| WO | 2010138715 A1 | 12/2010 |
| WO | 2011002215 A2 | 1/2011 |
| WO | 20110143024 A1 | 11/2011 |
| WO | 2011149187 A2 | 12/2011 |

OTHER PUBLICATIONS

European Patent Office; Published Search Report in International Patent Application No. PCT/EP2013/001252 dated Oct. 31, 2013; 14 pages.
European Patent Office; Written Opinion in International Patent Application No. PCT/EP2013/001252 dated Oct. 22, 2013; 20 pages.
German Patent Office; Examination Report in German Patent Application No. 10 2012 008 535.4 dated Nov. 14, 2012; 5 pages.
German Patent Office; Examination Report in German Patent Application No. 10 2012 015 541.7 dated Feb. 8, 2013; 5 pages.
German Patent Office; Examination Report in German Patent Application No. 10 2012 018 432.8 dated Apr. 23, 2013; 5 pages.
Korean Patent Office; Office Action in Korean Patent Application No. 2014-7032821 dated Jun. 29, 2016; 5 pages.
Chinese Patent Office; Office Action in Chinese Patent Application No. 201510041821.4 dated Jun. 1, 2016; 10 pages.
U.S. Patent Office; Office Action in U.S. Appl. No. 14/523,468 dated Jun. 17, 2016; 22 pages.
Korean Patent Office; Office Action in Korean Patent Application No. 20147032823 dated Jun. 29, 2016; 5 pages.
Korean Patent Office; Office Action in Korean Patent Application No. 20147032822 dated Jun. 29, 2016; 5 pages.
Chinese Patent Office; Office Action in Chinese Patent Application No. 201510041852.X dated Jun. 3, 2016; 10 pages.
Chinese Patent Office; Office Action in Chinese Patent Application No. 201510041943.3 dated Jun. 24, 2016; 10 pages.
Chinese Patent Office; Office Action in Chinese Patent Application No. 201510041943.3 dated Feb. 20, 2017; 17 pages.
Chinese Patent Office; Office Action in Chinese Patent Application No. 201510041821.4 dated Jan. 22, 2017; 19 pages.
Chinese Patent Office; Search Report in Chinese Patent Application No. 201380033455.7 dated Jan. 24, 2017; 5 pages.
Chinese Patent Office; Office Action in Chinese Patent Application No. 201510041988.0 dated Jan. 4, 2017; 19 pages.
Chinese Patent Office; Office Action in Chinese Patent Application No. 201510041943.3 dated Mar. 5, 2018; 22 pages.
European Patent Office; Examination Report in related European Patent Application No. 14 004 403.3 dated Mar. 26, 2018; 5 pages.

* cited by examiner

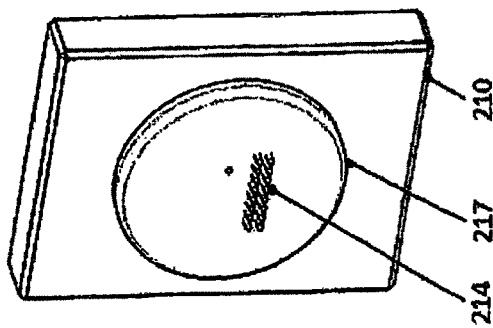
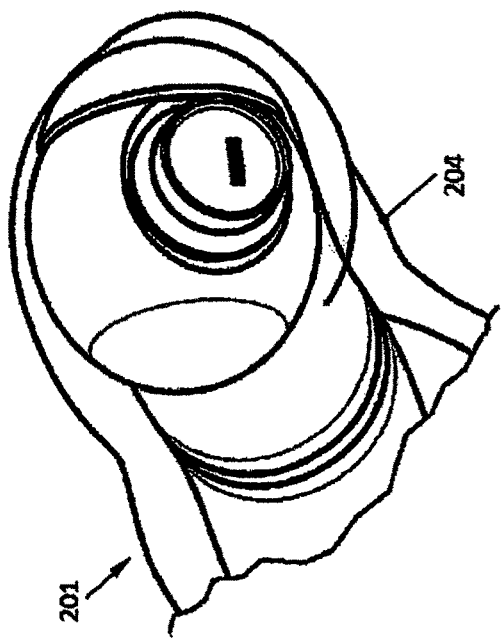
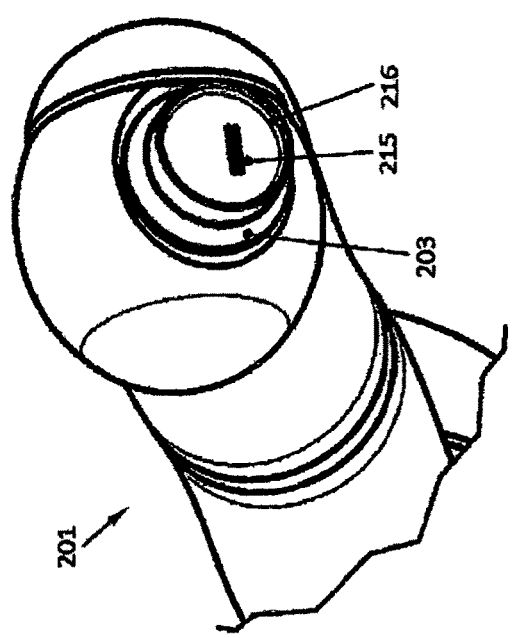
Fig. 6A
Fig. 6B

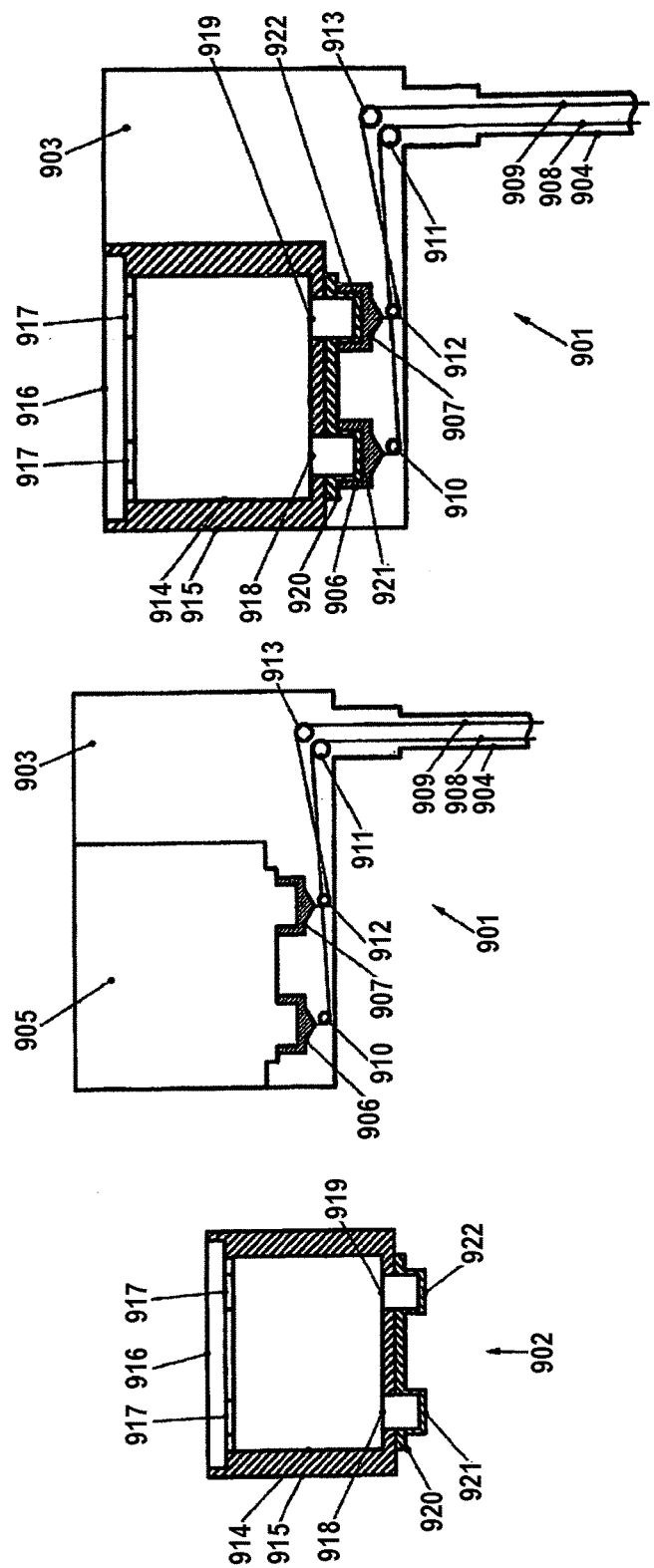

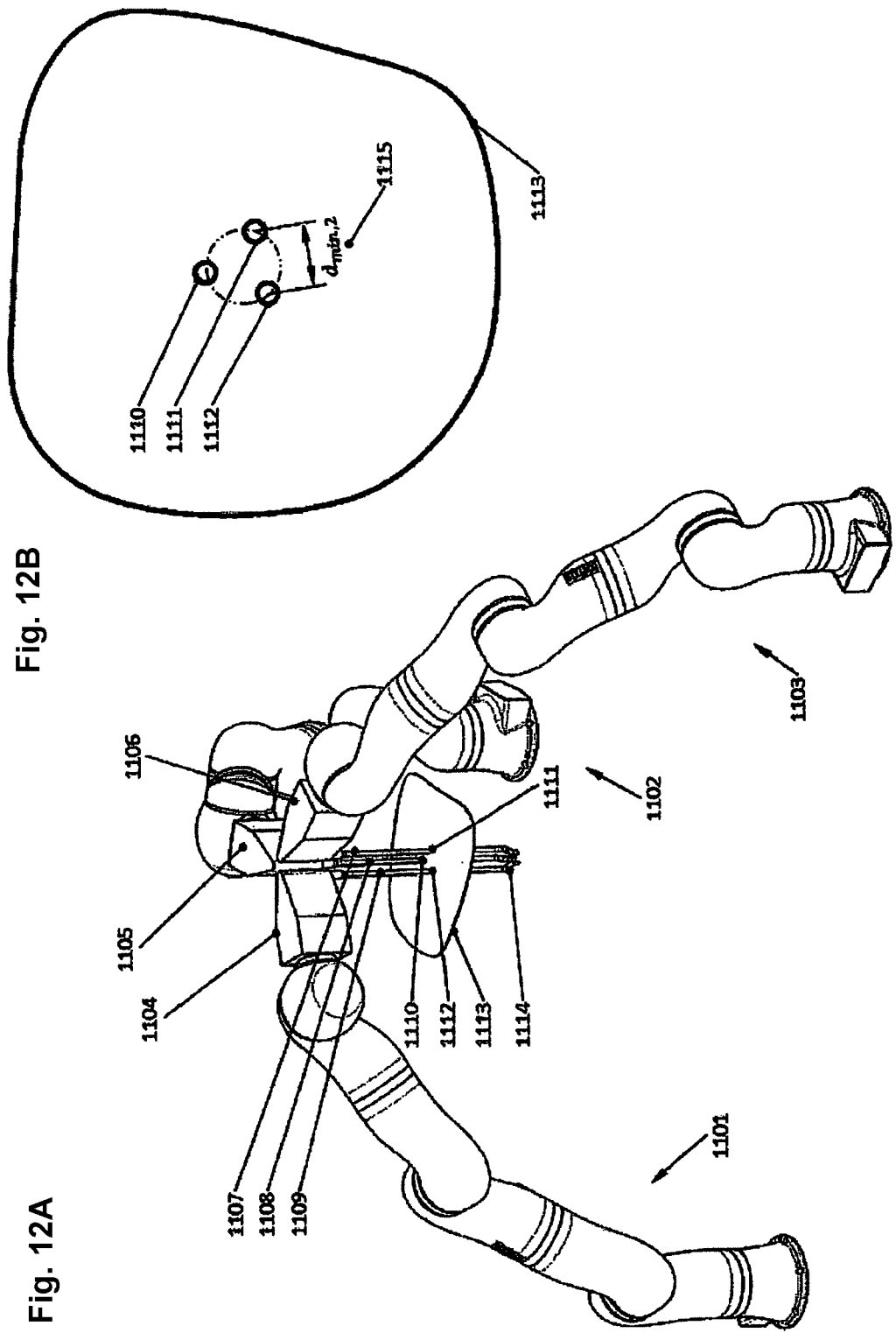

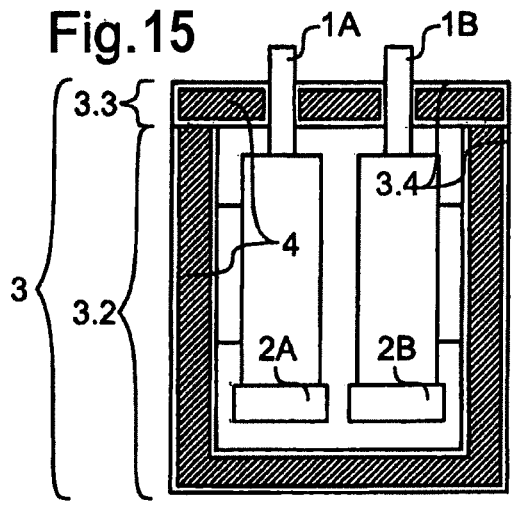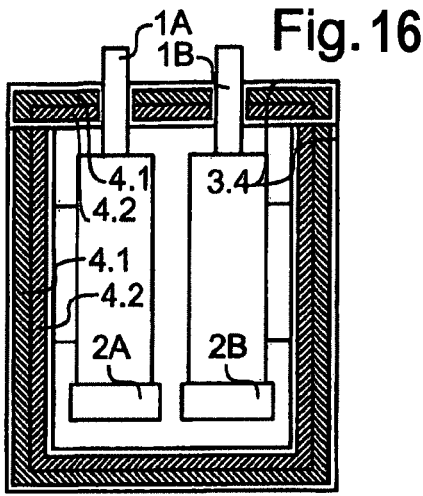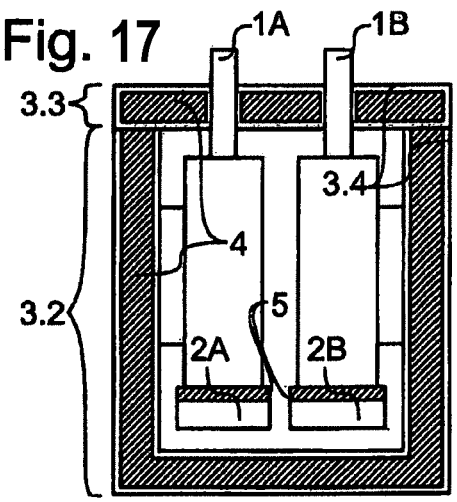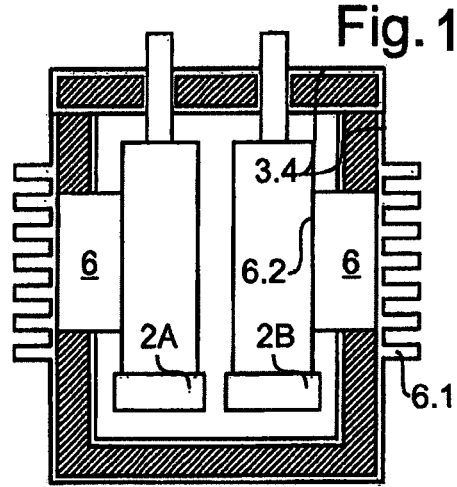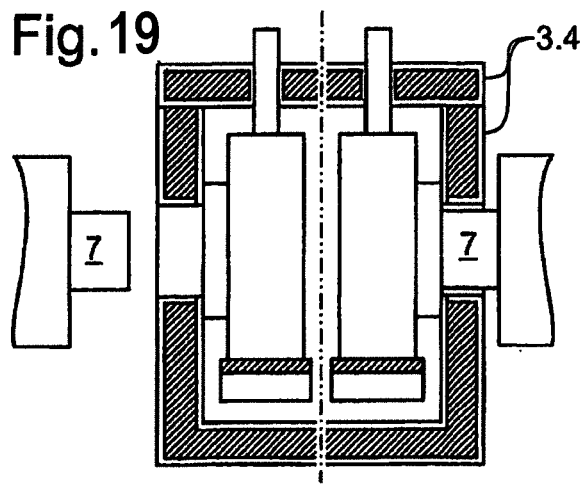

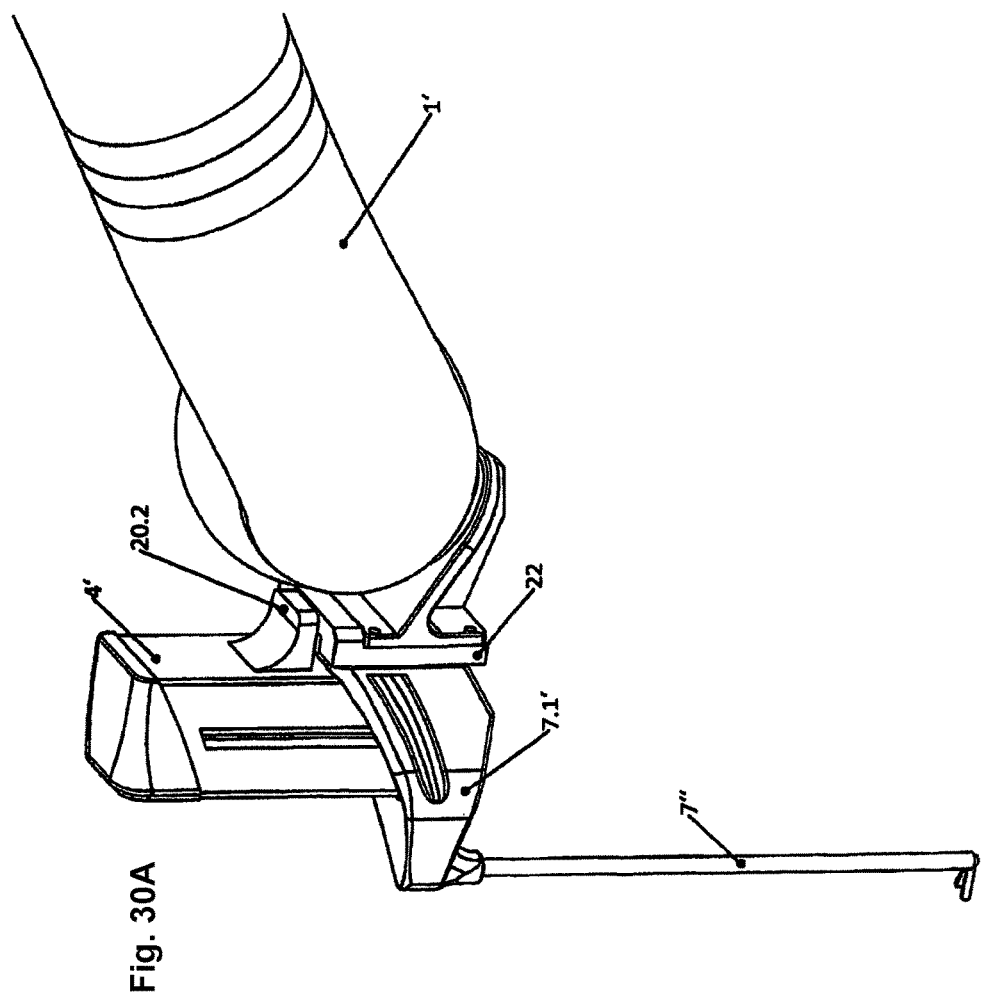

SURGICAL ROBOT SYSTEM

CROSS-REFERENCE

This application is a continuation of International Patent Application No. PCT/EP2013/001252, filed Apr. 25, 2013 (pending), which claims priority to DE 10 2012 008 535.4 filed Apr. 27, 2012, DE 10 2012 015 541.7 filed Aug. 6, 2012, and DE 10 2012 018 432.8 filed Sep. 18, 2012; and is related to U.S. patent application Ser. Nos. 14/523,142, 14/523,280, 14/523,422, 14/523,468, each filed Oct. 24, 2014, the disclosures of which are incorporated by reference herein in their entirety.

TECHNICAL FIELD

One aspect of the present invention relates to a surgical robot system with a robot assembly and an instrument assembly with at least one instrument controlled by the robot assembly, such an instrument assembly and a method for assembling such a surgical robot system or such an instrument assembly.

BACKGROUND

Surgical instruments are required to be as sterile as possible. On the other hand, robots and drives can only be sterilized with difficulty due for example to lubricants, power take-off and the like.

One approach consists in making the instrument itself drive-less and to actuate it by means of a robot connected to it, for example moving an end effector such as forceps, shears or the like using remote manipulators. The drive-less instrument itself is easily sterilized. The non-sterile robot with the drive for the instrument is encased with a static sterile barrier. EP 1 015 068 A1 proposes an adapter attached to a sterile case of the robot, through which the instrument drive is mechanically fed.

If the drive is integrated into the instrument, as is also the case with the present invention, more compact robots can advantageously be used, as the feed-through of the instrument drive can be dispensed with.

Here however several problems arise: for one, instruments with integral drive are larger than drive-less instruments. This can make manipulation more difficult, in particular with several cooperating robots. For another the drive, which as a rule is non-sterilizable or sterilizable only with difficulty, is no longer shielded by the sterile case of the robot.

SUMMARY

An object of one aspect of the present invention is to solve at least one of the aforementioned problems, or to make available an improved surgical robot system.

This object is solved by a surgical robot system with a surgical robot system as described herein. Claims 2 and 11 respectively place an instrument assembly for such a surgical robot system, and a method for assembling such a surgical robot system or such an instrument assembly.

Another aspect of the present invention relates to a surgical robot system with a robot assembly and an instrument assembly coupled thereto, a surgical instrument, a sterilizable drive unit for a surgical instrument and a method for sterilizing such a drive unit.

In order to satisfy sterility requirements, operating room objects are usually sterilized in advance, most by subjecting them to hot steam and/or hot air.

According to internal company prior art, surgical robot systems with one or more robots and surgical instruments controlled by the same are already known, having an instrument shaft and a drive unit that can be coupled thereto for actuating the degrees of freedom of an end effector.

Specific components of such surgical robot systems are in part not designed for thermal loads such as occur during sterilization. This applies in particular to specific electronic components of drive units of robot-controlled surgical instruments, particularly for position sensors, which are particularly advantageous for teleoperated actuation of an end effector in minimally invasive robotic surgery.

Consequently, up until now the complete surgical robot system has been covered with a sterile single-use case, which is costly and waste-intensive and makes manipulation more difficult.

An object of one aspect of the present invention is to improve the sterilization of drive units of surgical instruments of surgical robot systems.

This object is solved by a sterilizable drive unit with the features described herein, a method for sterilizing such a drive unit, a surgical instrument with such a drive unit, and a surgical robot system with such an instrument.

Another aspect of the present invention relates to a surgical robot system with a robot assembly and an instrument assembly, an instrument assembly for such a surgical robot system, a manual operating unit for such an instrument arrangement and methods for equipping such a robot assembly with an instrument, and an instrument with a drive unit.

A generic surgical robot system is known from the applicant's German patent application 10 2012 008 535.4, relating to a surgical robot system, the disclosure content whereof was incorporated in full into the disclosure of the present invention. FIG. 26 shows for explanation by way of an example a surgical robot system according to the invention with three robots 1, 2, 3, each controlling an instrument 4, 5 and 6 respectively, each having at the proximal end near the robot a drive unit and at the distal end remote from the robot an end effector with one or more degrees of freedom for positioning within an operation area 14. An instrument shaft 7, 8 and 9 respectively extends between the proximal and distal ends, which reaches the operation area 14 inside a patient through a small opening 10, 11 and 12 respectively, for example in an abdominal wall 13. Not shown is a haptic input station, from which the surgical robot system is teleoperated.

An object of one aspect of the present invention is to improve a generic surgical robot system.

This object is solved by an instrument assembly for a surgical robot system with the features described herein, a surgical robot system with such an instrument assembly, a manual operating unit for such an instrument assembly, and a method for equipping a surgical robot system or instrument, respectively.

Surgical Robot System

A surgical robot system according to one aspect of the present invention includes a robot assembly with one or more, particularly two, three or four, robots. One or more robots of the robot assembly can, in one embodiment, have six or more joints, particularly rotary joints, more than six joints allowing advantageous positioning of the redundant robot. In one embodiment, the robot(s) have a control. Here, several robots can have a common central control and/or individual controls. In one embodiment, the robot assembly, in particular one or more robots, can be positioned, particularly separably fastened, on an operating table.

Instrument Assembly

An instrument assembly according to one aspect of the present invention includes one or more instruments controlled by the robot assembly; it is accordingly equipped for attachment to the robot assembly, or configured as a robot-controlled instrument assembly. In one embodiment, one instrument each is attached or attachable, respectively, preferably separably, to one or more robots of the robot assembly, particularly with a form-fitting, friction-locking and/or magnetic, particularly electromagnetic connection. In a further development, the instrument assembly can have multiple, particularly different instruments, which can be attached, particularly selectively, to the same or to different robots of the robot assembly.

One or more instruments of the instrument assembly each have a single- or multi-part, particularly tubular and/or flexible or completely or partially or sectionally rigid instrument shaft which is designed for partial insertion into a patient. At its distal end, a single- or multi-part end effector, particularly a scalpel, forceps or shear shank or the like, can be attached, particularly separably. Additionally or alternatively, a light source, an optical imaging device, particularly a camera chip, and/or a light guide end for example can be positioned at the distal end, so that the instrument can be configured as an endoscope.

In one embodiment, an instrument is an endo or minimally invasive surgical instrument ("MIC"), particularly endoscopic, for example laparoscopic or thoracoscopic. In particular, the instrument shaft can be designed and equipped so as to be inserted into the patient through an entrance which preferably matches substantially the outer diameter of the instrument shaft, particularly through a trocar, and actuated there.

The instrument shaft, particularly a distal part and/or an end effector of the instrument shaft, can have one or more degrees of freedom. In particular, one or more parts of the end effector can each have one or two rotational degrees which are preferably perpendicular to a longitudinal axis of the instrument shaft. For example, a two-part end effector can consist of forceps and shears, the shanks whereof swivel in opposite directions about the same axis of rotation.

In one embodiment, to actuate one or more degrees of freedom of the instrument shaft, an instrument has a drive train assembly with one or more drive trains. What is meant by a drive train in the present case is in particular an assembly with one or more transmission means for mechanical, hydraulic and/or pneumatic transmission of motions and/or forces, anti-parallel force pairs, i.e. torques, also being generally designated as forces in the present case for the sake of a more compact presentation. Such transmission means can in particular be or include traction cables, push rods, links, gear trains, particularly gate-type gears for converting between a rotational and a translational motion, pulleys, coupling elements and the like. Consequently, in the present case, a drive train means in particular a chain of mechanically interconnected transmission means which transmit an input-side actuation by a drive unit to the instrument shaft, particularly an end-effector of the instrument shaft, on the output side, and thus actuate a degree of freedom of the instrument shaft. Two or more drive trains of the drive train assembly can in particular be set parallel to and/or cross over one another, at least partially or sectionally.

According to one embodiment, moreover, an instrument has a modular drive unit for actuating the drive train assembly. By a modular drive unit is meant in particular a drive unit which is constructed as a component unit and can be manipulated as a whole, and in particular is separably attachable to the instrument, particularly to an instrument housing.

The drive unit is configured for actuating one or more degrees of freedom of the instrument shaft through the drive train assembly, and can have one or more translational and/or rotational drives for this purpose, which can in particular have one or more hydraulic, pneumatic and/or electric motors. In one embodiment, the drive train assembly can actuate translational and/or rotational degrees of freedom of the instrument shaft and transmit translational and/or rotational actuations of the drive unit translationally and/or rotationally and possibly convert one to the other. In one embodiment, the drive unit can have one or more driven shafts, the rotary motion whereof actuates the drive train assembly. Additionally or alternatively, the drive unit can have one or more pistons (rods), the translational or linear motion whereof actuates the drive train assembly. The drive train assembly can impart or transmit such rotational or translational motions, for example by means of traction cable or push rod drives, to the degrees of freedom of the instrument shaft. In one embodiment, the drive unit has electrical contacts for supplying power and/or for transmitting signals, which can in particular be configured for coupling with the electromechanical interface explained hereafter.

Instrument Housing

According to one aspect of the present invention, one or more instruments of the instrument assembly each have an instrument housing with a drive train housing part, on which at least a portion of the drive train assembly is positioned and which, in one embodiment, can be separably or fixedly or permanently connected to, in particular formed integrally with, the instrument shaft. In the case of a drive train housing part permanently connected with the instrument shaft, the entire drive train assembly, starting from an input interface to the drive unit, can be positioned at, particularly in, the drive train housing part. In the case of a separably connected instrument shaft and drive train housing part, a part of the drive train assembly can be positioned at, particularly in, the drive train housing part and another part, which can be coupled thereto, can be positioned at, particularly in, the instrument shaft. In one embodiment, a degree of freedom, particularly actuated and/or rotary, can be provided or configured between the instrument housing and the instrument shaft, in order to turn the instrument shaft, in particular a distal end with an end effector or the like, about the longitudinal axis. This too is considered as being "connected."

The instrument housing also has a drive unit housing part with a hollow space which is configured to accommodate a drive unit or wherein a drive unit is, particularly separably, accommodated, the drive unit housing part having a seal, for providing a sterile seal for an insertion opening of the hollow space, and a dynamic sterile barrier, which delimits the hollow space in a sterile manner and from or through which the drive train assembly can be actuated.

As further explained hereafter, the, particularly non-sterile, drive unit can be advantageously integrated into a robot-controlled surgical instrument which must satisfy appropriate sterilization requirements in the OR area, by accommodation in a hollow space of the drive unit housing part, which is provided with a sterile seal by the seal and the dynamic sterile barrier, without requiring cumbersome and damage-prone encasing of the drive unit by a film, a sleeve or the like. In the present case, sterile means in particular sterile in the medical, particularly (micro)surgical sense.

By a dynamic sterile barrier is meant, in the present case, a sterile barrier which allows movement of the drive unit and/or of the drive train assembly and in the process provides a sterile seal between two sides or spaces, particularly a sterile barrier through which forces and/or motions of the drive unit can be transmitted or directed.

In one embodiment, a sterile barrier can be made movable and move along with motions of the drive unit and/or of the drive train assembly. Thus for example an elastically deformable membrane can follow a translational motion of a piston of the drive unit and mechanically transmit it to the drive train assembly. Likewise a rotary coupling element under sterile seal can follow a rotary motion of a shaft of the drive unit and transmit it mechanically to the drive train assembly. In one embodiment, the dynamic sterile barrier provides for sterile mutual isolation of the drive unit and the drive train assembly.

In another embodiment, a dynamic sterile barrier can have a sterile moving seal through which a transmission means of one or more drive train assemblies is routed, particularly a contact-less seal such as a gap or labyrinth seal, or a contacting seal, in particular an elastic, pre-tensioned lip or the like. For example, a traction cable or a push rod of the drive train assembly can be routed through a gap, labyrinth or rubbing lip seal, which thus isolates, in a sterile manner, one side of the drive train assembly from the opposite side. In one embodiment, the dynamic sterile barrier isolates, in a sterile manner, two sections of the drive train assembly from one another.

The instrument housing, in particular the drive unit and/or the drive train housing part, is made dimensionally stable, particularly rigid, in one preferred embodiment. It can in particular include, particularly be made of, plastic and/or metal. As explained previously, the manipulation and integration of a non-sterile drive unit into an instrument of a robotic surgical system can be considerably improved, in particular simplified, by this dimensionally stable construction. In one embodiment, however, the drive unit housing part can also be made at least partially flexible. It can in particular have a dimensionally stable, rigid portion, which is provided or configured for connection to the drive train housing part and/or for manipulation, in which in particular one or more grips, recessed grips or the like can be formed. A flexible portion, in particular a film sleeve, which can be cost-effectively manufactured and simplifies storage, can be connected with this dimensionally stable, rigid portion.

In one embodiment, the drive train housing part and the drive unit housing part are separably interconnected, in particular in a form-fitting and/or friction-fitting manner and/or magnetically, particularly electromagnetically, for example screwed together or interlocked or the like. This makes possible even simpler sterile manipulation of the non-sterile drive unit, if it is accommodated in the independent drive unit housing part and can be manipulated along with it, particularly during an operation.

It makes possible in particular the separable connection of two or more drive train housing parts and/or the withholding of two or more drive unit housing parts and their selective interconnection. Thus for example two or more identical or different drive unit housing parts with the same or different drive units can be withheld, so as to be substituted when needed or to be connected with the same drive train housing part. Likewise, two or more identical or different drive train housing parts can be withheld, so as to be substituted when needed or to be connected with the same drive unit housing part.

In one embodiment, in addition or as an alternative to substitution of the drive unit housing part, even in particular in the case of a drive unit housing part permanently connected with a drive train housing part, the modular drive unit separably accommodated in the hollow space can be substituted, optionally. To avoid any possibility of confusion in such cases, two or more drive units and/or two or more drive unit housing parts can have different, particularly mechanical, coding. Mechanical coding can consist in particular of a complementary contour of a drive unit and a drive unit housing part, for example with interpenetrating protrusions and recesses having different shapes, size and/or arrangements. In addition or as an alternative to mechanical coding, the drive unit and/or the drive unit housing part can have optical and/or electrical coding, for example circuitry which can only be completed by the matching counterpart or the like. In addition or as an alternative, particularly to mechanical coding of pairs consisting of a drive unit and a drive unit housing part, separably interconnectable drive unit housing parts and drive train housing parts can also be coded in pairs, mechanically in particular.

In one embodiment, the drive train housing part and the drive unit housing part are permanently interconnected, in particular integrally formed together. This can advantageously provide in particular a more compact and/or more robust instrument housing.

The dynamic sterile barrier can be separably connected with the drive train housing part and/or the drive unit housing part. In particular, it can be inserted into the hollow space in the drive unit housing part, and be fastened there in a form-fitting or friction-fitting fashion. This makes possible cost-effective manufacture of the dynamic sterile barrier as a single-use article. Likewise, the dynamic sterile barrier can be permanently connected, in particular integrated, with the drive train housing part and/or the drive unit housing part, which in particular prevents the dynamic barrier from being forgotten.

Electromechanical Interface

According to one embodiment of the present invention, the instrument assembly has an electromechanical interface for separably attaching the instrument housing, particularly the drive train housing part, to the robot assembly. In the present case, electromechanical interface means in particular an element which is configured for mechanical attachment of an instrument to a robot and for transmitting electrical power and/or electrical signals. Such an element can be separably attached, particularly with a form-fitting or friction fit, to the instrument and/or the robot, for example screwed or interlocking.

In a further development, the electromechanical interface is connected by means of a mechanical plug connection with the instrument housing and/or the robot assembly. For this purpose, the electromechanical interface can be configured as a plug connector on the side facing the instrument housing and/or the robot, which is configured for plug-in connection with a suitable plug connector of the instrument housing or robot, for example as a radial protuberance which engages form-fittingly into a recess or the like.

In a further development, the interface, particularly positively guided by the plug connection, can pass through a static sterile barrier of the robot, particularly a film-like casing, and or of the instrument, particularly a static sterile seal, particularly a contact-less seal such as a gap or labyrinth seal, or a contacting seal such as a rubbing lip seal, while perforating it.

One or more electrical contacts of the electromechanical interface can simultaneously constitute the mechanical plug connection or be integrated therein. Likewise, one or more electrical contacts of the electromechanical interface can also be configured as rubbing contacts, which are not plugged in, particularly spring-loaded contact elements or leaf spring contacts which in particular are contacted on a rigid opposite surface.

Instead of an electromechanical interface, a purely mechanical interface can also be provided, in particular if, in a further development, wireless power and/or signal transmission to the drive unit is provided.

Seal

The seal for sterile sealing of the insertion opening can, in one embodiment, have a cover-like configuration. It can be separably connected with the drive unit housing part, particularly with a form-fitting, friction-locking and/or magnetic, particularly electromagnetic connection, by plugging in, interlocking, screwing or the like for example. In a further development, it extends out beyond the edge of the insertion opening, so that a region of the insertion opening, where the non-sterile drive unit rubs during insertion into the hitherto sterile drive unit housing part and thus contaminates it, is sealed along with it by the seal.

The seal or the insertion opening can be located on a face of the instrument housing facing away from the instrument shaft, so that the drive unit can be removed or inserted on the side opposite the instrument shaft. In addition or as an alternative, the seal or the insertion opening can, for example for more compact space utilization or better manipulation, be positioned on a face of the instrument housing facing the instrument shaft, next to the instrument shaft. For better manipulation in particular, the seal or the insertion opening can also be positioned on an outside surface of the instrument housing, which can preferably extend—at least substantially—transverse to a longitudinal axis of the instrument shaft. In other words, the drive unit can also be inserted into the drive unit housing part sideways—relative to the longitudinal axis of the instrument shaft.

In one embodiment, particularly in a cover-like seal, fixing means for fixing the drive unit can be located in the hollow space and thus fix the same upon closing the cover. In addition or alternatively, fixing means can be located at other places in the hollow space. In one embodiment, one or more fixing means are configured as braces. What is meant by this in the present case is that they brace the drive unit, preferably elastically, for the purpose of fixing it. To this end, a fixing means can have an elastic element, for example an arrangement of one or more springs. In addition or alternatively, one or more fixing means can be configured to interlock and to fix the drive unit with a form-fitting and/or friction fit in the hollow space.

Drive Unit

According to one aspect of the present invention, the drive unit is laterally offset from a longitudinal axis of the instrument shaft toward a connection of the instrument housing to the robot assembly. This means in the present case that the drive unit, viewed in a direction perpendicular to the longitudinal axis of the instrument shaft, is not flush with the longitudinal axis, but is offset from it toward a contact surface of the instrument which is provided or configured for attachment of the instrument to a robot of the robot assembly. The drive unit can in particular be positioned in the lateral direction between the longitudinal axis of the instrument shaft and the connection to the robot assembly. Likewise, it can also extend laterally out beyond the longitudinal axis of the instrument shaft, the volume and/or mass centre and/or an axis of symmetry of the drive unit, however, preferably being positioned in the lateral direction between the longitudinal axis of the instrument shaft and the connection to the robot assembly.

Due to the lateral offset from the instrument shaft, the instrument is advantageously smaller in the region or in the direction of its longitudinal axis. In this manner, the longitudinal axes in particular of several instruments or instrument shafts of cooperating robots of the robot assembly can be placed closer together and thus operated in a smaller space.

In particular, so as to increase the mobility of such closely grouped operating instruments, it is provided in a further development that at least one instrument housing tapers in the lateral direction toward the longitudinal axis of the instrument shaft, and in particular has a wedge-shaped cross-section. A pivoting range of the instrument about the longitudinal axis of the instrument shaft can thereby be advantageously increased, before the tapering instrument housing, which can in particular be a drive train housing part, collides with another instrument.

Assembly Method

In order to assembly an instrument assembly the invention provides, according to one aspect, that a sterile drive unit housing part is initially supplied and sterile covering is provided for an area surrounding the insertion opening, preferably by means of a removable sterile guard. Next, the non-sterile drive unit is inserted into the hollow space of the drive unit housing part and thereby contaminates this hollow space. Now the seal is given a sterile seal, possibly after removal of the sterile cover, a sterile cover for example being inserted or applied so as to form a sterile seal.

In this manner, the non-sterile drive unit can be accommodated in the sterile drive unit housing part and then handled together with it in sterile fashion.

To assembly a robotic surgical system the invention provides, according to one aspect, to package the robot assembly in sterile condition, in particular by encasing one or more robots with a film-like static sterile barrier. In addition or alternatively, one or more drive units of the instrument assembly, in particular as described earlier, can be packaged in sterile condition in a drive unit housing part by inserting them into it and then sealing the seal in sterile fashion.

A mechanical plug connection of an electromechanical interface is then formed between the robot assembly and the instrument assembly. To this end, the electromechanical interface can be connected with the robot assembly and/or the instrument assembly by means of a mechanical plug connection, a protuberance, particularly a radial one, or a recess of the interface being inserted or applied form-fittingly into a suitable recess or onto a suitable, particularly radial, protuberance of the sterile-packaged robot or instrument assembly.

Preferably guided by this mechanical plug connection, the electromechanical interface, which for this purpose can have one or more electrically conductive protrusions, perforates this static sterile barrier. Due to the perforation, the static sterile barrier continues to provide a sterile seal. As in the process penetration occurs only from the sterile into the non-sterile, the sterile is also not contaminated. Overall, in one embodiment, a mechanical plug connection of the electromechanical interface is formed in advance from an electrical plug connection of the electromechanical interface.

Next, the electromechanical interface is fixed. This can occur with a form fit or a friction fit, particularly through the mechanical plug connection itself. In addition or alternatively, it can be set up for screwing the electromechanical interface to the robot and/or the instrument, particularly with perforation of the static sterile barrier.

As previously discussed, a robot-controlled surgical instrument with an integrated drive unit can advantageously be handled in sterile fashion by means of the present invention. Accordingly, in one embodiment, the instrument shaft and/or an instrument housing, in particular a drive unit housing part and/or a drive train housing part, in particular its drive train assembly, are sterile or sterilized. By inserting the non-sterile drive unit, only the hollow space is contaminated, which however is sealed off in sterile fashion by the seal, sealed in a sterile fashion and the dynamic sterile barrier against the external environment. Through the electromechanical interface, an electrical connection with the robot and/or the drive unit can be created, while maintaining sterility, through which electrical power and/or control signals can be transmitted between the robot and the drive unit. Likewise, the drive unit can be supplied with power and/or controlled, wirelessly for example, in particular using alternating electromagnetic fields, perhaps inductively and/or by radio. Likewise, the drive unit can have an energy storage unit, for example a battery or a rechargeable storage battery, and/or have an autonomous control unit.

A sterilizable drive unit according to one aspect of the present invention has an actuator assembly with one or more actuators for actuating one or more degrees of freedom of an end effector of a surgical instrument, and endoscope with distal kinematics in one embodiment. In this embodiment, an actuator can have at least one, preferably force- and/or position-controlled electric motor, or in particular be at least one, preferably force- and/or position-controlled electric motor. A position-controlled electric motor can advantageously improve teleoperating actuation of an end effector during minimally invasive robotic surgery.

The drive unit also has a component assembly with one or more electronic components. In one embodiment, an electronic component can have, or particularly be, a position-determining means, particularly a position sensor, for determining a position of an actuator of the actuator assembly, possibly a resolver, incremental or absolute angle encoder. In one embodiment of the present invention, additionally or alternatively, an electronic component can be configured for processing and/or storing data, for example for filtering signals or the like; it can in particular have, or in particular be, a microchip or microcontroller. In one embodiment of the present invention, the electronic component has an upper temperature limit of at most 100 degrees Celsius, particularly at most 90 degrees Celsius.

The drive unit has a sterilizable housing. A sterilizable housing can in particular be provided or configured to be subjected with hot steam and/or air at a temperature of at least 100 degrees Celsius, in particular at least 120 degrees Celsius, preferably at least 130 degrees Celsius, in particular for at least 5 minutes, preferably at least 20 minutes and/or at a pressure of at least 2 bar, particularly at least 3 bar. In one embodiment the housing can be—substantially at least—of cylindrical or box-shaped construction.

In one embodiment, the housing is fluid-tight, in particular against the aforementioned hot steam, and/or airtight. In one embodiment, it can be made up of two or more parts, at least two housing parts being separably interconnectable or interconnected in a further development, in order to allow access to an interior of the housing. In one embodiment, two interconnected housing parts have a, particularly elastic, gasket, particularly an O-ring seal. In one embodiment, they can be screwed, interlocked, clipped together or the like.

The actuator assembly and the component assembly are located inside the housing. In one embodiment, the actuator assembly is fastened to the housing, separably or permanently, by means of a bracket. The component assembly can in particular be fastened, separably or permanently, to the actuator assembly and/or to the housing.

The housing has a housing wall. A housing wall, for the purpose of the present invention, can be an outer or an inner wall of the housing. A housing wall for the purpose of the present invention can completely enclose the interior of the housing and have for this purpose a plurality of wall parts, in particular angled with respect to one another, for example the side walls of a box-shaped housing or the outside surface of a cylindrical housing as well as their respective face covers, of which preferably at least one is separably attached. The housing wall can, in one embodiment, be dimensionally rigid. It can have metal and/or plastic, and in particular be made thereof.

According to one aspect of the present invention, a thermal insulation layer is placed on the housing wall. This can be located a side of the housing wall facing the component assembly. Additionally or alternatively, a thermal insulation layer can be located on a side of the housing wall facing away from the component assembly. According to one embodiment, then, the housing wall in particular can be an outside wall of the housing, on the inner side whereof, facing the interior of the housing or the component assembly, a thermal insulation layer is located. Likewise, the housing wall can be an inner wall of the housing, on the outer side whereof, facing the interior of the housing or the component assembly, a thermal insulation layer is located. In a further development, another thermal insulation layer can be located on the inner side of such an inner wall facing the interior of the housing or the component assembly, or the inner housing wall can be sandwiched between two thermal insulation layers.

A thermal insulation layer can, in one embodiment, completely cover the inner and/or outer surface of the housing wall, substantially at least, or completely enclose a housing interior, substantially at least. Likewise, a thermal insulation layer can, in one embodiment, be located only on one or more portions or segments of the housing wall, preferably at least at the level of the component assembly or facing the component assembly.

Due to a thermal insulation layer on one or more segments of the housing wall, heat conduction through the entire housing wall, and thus temperature loading of the component assembly, can advantageously be reduced. If a thermal insulation layer completely protects the housing wall, substantially at least, then heat transfer in particular into the interior of the housing, and thus onto the component assembly, can be minimized.

According to one aspect of the present invention, additionally or alternatively to a thermal insulation layer on the housing wall, a thermal insulating layer can be located between the component assembly and the actuator assembly. Heat conduction from the actuator assembly to the component assembly, and thus temperature loading of the component assembly, can be advantageously reduced thereby.

A thermal insulation layer on the housing wall and/or between the component and actuator assemblies can be single- or multi-layer. In one embodiment, one or more layers of a thermal insulation layer can have, in particular be made of, one or more thermal barrier materials, particularly mineral wool, rigid polyurethane foam or the like. Additionally or alternatively, one or more layers of a thermal insulating layer can have vacuum insulation. To this end, the respective layer can have two surfaces spaced apart, delimiting between them a fluid- , particularly air-tight space, which is preferably filled with air or gas at reduced pressure. In a further development, a porous supporting core can be located in the space. In one embodiment, the housing wall forms one surface of a vacuum insulation layer. In a further development, the housing wall is, at least sectionally, of double wall construction and constitutes the two spaced surfaces of a vacuum insulation layer.

A thermal insulation layer in the sense of the present invention can have a thermal conductivity λ at 20 degrees Celsius amounting to at most 1 W/(K m), in particular at most 0.5 W/(K m), preferably at most 0.05 W/(K m).

Heat conduction into the interior of the housing during sterilization, particularly with hot steam or air, can be advantageously reduced by a thermal insulation layer on the housing wall. In operation, however, the actuator assembly in particular can generate waste heat, the escape whereof can be disadvantageously reduced by a thermal insulating layer on the housing wall.

For this reason in particular, it can be provided in one embodiment that—particularly at the level of an attachment of the actuator assembly to the housing wall or facing the actuator assembly on the housing wall—only a thermal insulating layer with high thermal conductivity, in particular thin and/or with fewer layers, is placed, or the housing wall in this region is constructed entirely or partially without an insulating layer. In this manner, in operation, waste heat from the actuator assembly can be conducted through its connection or attachment to the housing wall and transferred from there to the surroundings.

To this end in particular, in one embodiment, a drive unit has a heat conduction assembly with one or more heat conduction means with a heat dissipation surface, which is positioned on an outer side of the housing wall facing the actuator assembly. The heat dissipation surface can in particular be positioned on an outer surface of the housing, or protrude from there. A heat conduction means in the sense of the present invention can in particular have a heat conductivity λ at 20 degrees Celsius amounting to at least 10 W/(K m), in particular to at least 100 W/(K m), preferably to at least 200 W/(K m). A heat conduction means in the sense of the present invention can in particular reach through a thermal insulation layer, or have a heat dissipation surface on the outer side of the housing wall and a heat absorption surface bonded thereto inside the housing, so as to channel the transmission of heat from the heat absorption to the heat dissipation surface.

In one embodiment, one or more heat conduction means or their heat absorption surfaces contact a bracket or a fastening of the actuator assembly on the housing wall; they are preferably connected with such a connection of the actuator assembly, in particular separably or integrally. In this manner, waste heat of the actuator assembly can be transmitted, by heat conduction, through the heat absorption surface(s), from this by heat conduction and/or convection to the heat dissipation surface(s) and transmitted from this or these to the surroundings.

The heat dissipation surface of one or more heat conduction means can have a surface area that is augmented relative to a base area of the heat dissipation surface, so as to increase heat transfer. In particular, a heat dissipation surface can have one or more cooling ribs, fins and/or pins.

The heat dissipation surface of one or more heat conduction means can be separably connected with the respective heat conduction means. In particular, a plug and/or clip connection between the heat dissipation surface and the heat conduction means can be configured or provided. This can make it possible to individually sterilize a surface connecting the heat transfer means to the heat dissipation surface separated from there, which has a smaller surface area than the heat dissipation surface, and the heat transfer surface, less heat entering the housing interior due to the smaller connection surface area. With the heat dissipation surface attached, waste heat from the actuator assembly can be more effectively removed through it. Likewise, the heat dissipation surface can also be permanently connected with the heat conduction means, in particular integrally incorporated into it, in particular by primary forming.

One or more heat conduction means of the heat conduction means assembly, which are also called heat conduction means, can be fixedly or permanently connected to the housing, particularly the actuator assembly, particularly formed integrally with a bracket of the actuator assembly. In particular, its waste heat in operation can be removed by a separable heat dissipation surface and/or a local thermal coupling with the actuator assembly, and heat input into the component assembly during sterilization nevertheless reduced.

In one embodiment, the heat conduction assembly has one or more switchable heat conduction means, which can be switched between a first, more heat conductive and a second, less heat conductive state. By a less heat conductive state is meant, for the purpose of the present invention, a state wherein a heat conduction means, under otherwise identical conditions, particularly at the same temperature difference between the housing interior and the outside, has a heat flux Φ passing through it which amounts to at least 10 times, particularly at least 100 times the heat flux in the less heat-conductive state. A second, less heat-conductive state in the sense of the present invention can in particular be a thermally insulating state wherein the heat conduction means has a heat conductivity amounting to at most 0.05 W/(K m).

In this manner, one or more switchable heat conduction means of the heat conduction means assembly can advantageously be switched into the second, less heat-conductive state during application of the heated fluid, and switched into the first, heat-conductive state so as to better remove waste heat from the actuator assembly during operation.

In one embodiment, one or more switchable heat conduction means can have a gap and a movable element for selective heat-conducting bridging of this gap. The gap can in particular be made fluid-tight, and in a further development can have reduced pressure or a vacuum, so as to reduce its heat conductivity. In one embodiment, the gap can be delimited by an elastic shell, which in a further development can have a folding or a bellows-like configuration. In the first, more heat-conductive state, the movable element bridges the gap and increases the heat conductivity of the heat conduction means; in the second, less heat-conductive state, the gap is not bridged and thus is thermally insulating, so that the heat conduction means can be switched by moving the movable element. In one embodiment, the gap can be located or formed within the thermal insulation layer.

In one embodiment, one or more switchable heat conduction means can each have one or more Peltier elements. By Peltier elements is meant in particular, for the purpose of the present invention, a thermoelectric converter which generates a temperature difference from a current flow based on the Peltier effect, in particular a so-called TEC ("thermoelectric cooler").

In one embodiment, one or more heat conduction means can have a fluid passage with a working fluid which can exchange heat with a heat exchange surface and a heat absorption surface of the heat conduction means. In operation, the working fluid can be present in particular in gaseous and/or liquid form. In particular, the heat conduction means can have, or be in particular, a so-called "heat pipe."

In a further development, a heat conduction means with a fluid passage with a working fluid can be configured as a switchable heat conduction means. To this end, it can have a flow control means for selectively actively streaming and/or blocking the working fluid. A flow control means for selectively actively streaming can in particular have, or in particular be a controllable circulating pump that in particular can be selectively activated for circulating the working fluid between heat absorption and transfer surfaces. By activating or stronger circulation, the heat conduction means can be switched into the first, more heat-conductive state, by deactivation or weaker circulation into the second, less heat-conductive state. Additionally or alternatively, in particular in a heat pump without a circulation pump, a flow control means for selective blocking of the working fluid can have a controllable, in particular openable and closeable, valve. Additionally or alternatively, a switchable heat conducting means with a heat pipe can have two heat pipe sections with thermal contact surfaces separated by a gap and a movable element for selective heat-conductive bridging of this gap.

A surgical robot system according to one aspect of the present invention has a robot assembly with one or more robots, each controlling a surgical instrument which is separably coupled with the respective robot, in particular by means of a robot flange or a robot interface configured for the purpose, mechanically in particular, in a further development also electrically and/or thermally. One or more of the robots can, in one embodiment, have six or more degrees of freedom each, particularly rotary degrees of freedom. They can be stationary or mobile. In particular, one or more of the robots can be fastened to an operating table, separably in particular. Additionally or alternatively, one or more of the robots can be fastened to a mobile platform. The robot-controlled instrument(s) are positioned by the robot assembly in one embodiment.

A surgical instrument according to one aspect of the present invention is robot-controlled, in one embodiment, by being separably coupled with a robot or is configured to that end, having in particular a robot interface configured for this purpose. It has an instrument shaft which, in one embodiment, is provided or configured for partial insertion into a patient, particularly through a trocar, and an end effector, which in one embodiment is provided for operating intracorporally, or to be inserted into a patient through one or more surgical or natural openings. In a further development, the end effector has one, two, three or more degrees of freedom, one or more of the degrees of freedom having, in a further development, a working space that is limited, in particular by stops. The end effector can for example have, or in particular be, a scalpel, forceps, clamps, shears or the like. Likewise, the end effector can have, or in particular be, an optical interface for sending and/or receiving light, particularly laser light or a camera image, and/or a fluid opening for introducing and/or aspirating fluids, particularly liquids and/or gases.

In one embodiment, the instrument shaft can be coupled with the robot assembly, or have a robot interface configured for this purpose. Additionally or alternatively, the drive unit can be mechanically and/or electrically coupled with the robot assembly, or have a robot interface configured for this purpose.

The sterilizable driven unit, in particular its actuator assembly, is in one embodiment separably coupled with the instrument shaft by means of an interface. In this manner, the same instrument shaft can advantageously be selectively coupled with various drive units, so as for example to actuate different degrees of freedom, to vary actuating power and/or accuracy and/or to recharge an energy storage unit, in particular a storage battery.

Accordingly, in one embodiment of the present invention, a sterilizable drive unit has an interface for separable coupling of the actuator assembly with an instrument shaft of a surgical instrument. The drive unit and instrument shaft can, in one embodiment, be separably interconnected, particularly screwed, clamped, interlocked, or clipped together or the like.

The interface can include one or more translationally and/or rotationally movable power take-off shafts of the actuator assembly. A translationally movable take-off shaft can have in particular a sterilizable axial seal, preferably a contact seal, in particular a so-called piston rod seal with one or more elastically deformed elements, which are compressed or stretched between the drive shaft and a guide, a translational relative motion of the drive shaft relative to the guide occurring with rubbing contact, during translational motion, between the elastically deformed element(s) and the drive shaft and/or the guide.

A rotationally movable drive shaft can have in particular a sterilizable radial seal, preferably a rubbing seal, particularly a so-called radial shaft seal with one or more elastically deformed elements which are elastically compressed or stretched between the drive shaft and a guide, a rotary relative motion between the elastically deformed element(s) and the drive shaft and/or the guide occurring, with rubbing contact, during rotary motion of the drive shaft relative to the guide.

In one embodiment, the interface has a shell which covers one or more penetration openings in the housing fluid-tight and encases one part of a drive shaft of the actuator assembly reaching through this opening, the shell preferably being elastically deformed by a motion of this part of the drive shaft(s). To this end, the shell can in particular have a folding or be of bellows-like construction.

For sterilizing a drive unit, according to one aspect of the present invention, an outer surface of the drive unit is exposed, particularly for a predetermined duration, particularly for at least 5 minutes, preferably at least 20 minutes, and/or at a pressure of at least 2 bar, in particular at least 3 bar with heated fluid, particularly steam or air, preferably at 100 degrees Celsius at least, particularly at least 120 degrees Celsius, preferably 130 degrees Celsius.

Here one or more switchable heat conduction means are preferably switched into the second, less heat-conductive state. Separable heat dissipation surfaces are preferably separated from the respective heat conduction means and can be exposed together with the housing.

In operation, the waste heat from the actuator assembly can be advantageously removed if switchable heat conduction means are switched into the first, more heat-conductive state. To this end the drive unit has, in one embodiment, a switchover means for selectively switching over at least one switchable heat conduction means of the heat conduction means assembly into the first, more heat-conductive state.

Selective switchover can be accomplished manually. In one embodiment, the switchover means is constructed or configured for automatic switching, particularly depending on a temperature in an interior of the housing and/or an operating parameter of the actuator assembly. It can for example determine a temperature inside the housing and, upon exceeding a predefined limiting value, switch one or more switchable heat conduction means into the first, more heat-conductive state. Likewise it can determine an operating parameter of the actuator assembly, for example an operating time and/or mechanical or electrical work done, perhaps an integral of electrical power absorbed by the actuator assembly and, upon exceeding a predefined limiting value, switch one or more switchable heat conduction means into the first, more heat-conductive state, as a corresponding quantity of waste heat is associated with it. Likewise, the heat conduction means assembly can also be switched into the first state following sterilization. The switchover means can control in particular a movement of a movable element, the application of current to a Peltier element, a circulation pump, a valve of a switchable heat conduction means. In one embodiment, the switchover means has a mechanism which is automatically operated by temperature control of a bimetallic strip, a shape-memory alloy or the like.

In one embodiment, a switchable heat conduction means can be switched, mechanically in particular, into the first state through the coupling of the drive unit with the instrument shaft and/or with the robot assembly. For example, and element can be moved by the coupling so as to bridge a gap, or a valve can be opened so as to release flow of a working fluid in a heat conduction means.

A surgical robot system according to one aspect of the present invention includes a robot assembly with one or more, particularly two or more identical, and/or two or more robots of different types. In a further development, one or more robots of the robot assembly each have at least 6, in particular at least 7 degrees of freedom, so as to position a robot-controlled, particularly teleoperated instrument.

Moreover, the surgical robot system includes an instrument assembly or an instrument system or set, according to one aspect of the resent invention, which includes one or more, particularly two or more identical and/or two or more instruments of different types, which are configured for attachment to a robot of the robot assembly, or have in particular an instrument interface for attachment to a robot of the robot assembly. In a further development, an instrument interface is configured for separable, particularly form-fitting and/or force-fitting, particularly friction-fitting attachment to a corresponding, particularly complementary robot interface of the robot assembly.

One or more instruments of the instrument assembly each have an instrument shaft which is provided for partial insertion into a patient. To this end, the shaft can be built rigid or movable, particularly articulated or flexible, sectionally or over its entire length, and or have a length amounting to at least 15 times, preferably at least 20 times its maximum diameter. For a more compact presentation, a proximal flange of the instrument shaft, which can have an instrument interface for attaching the instrument to the robot and/or a suitable drive interface for attaching a drive unit, is referred to as part of the instrument shaft.

In a further development, the instrument shaft has at its distal end an end effector with one or more degrees of freedom, in particular a scalpel, a clamp, forceps or shears, a sender and/or receiver, particularly a light source and/or a camera. In a further development, for actuating one or more degrees of freedom of the instrument shaft, particularly of instrument shaft parts relative to one another, and/or of an end effector, a drive train can be positioned in the instrument shaft. By a drive train is meant in particular, in the present case, in a general sense an assembly for mechanical, pneumatic, hydraulic and/or electrical transmission of forces and/or motions, which in a further development can have in particular one or more traction- and/or push-rods, cables, belts, rollers, gears, hydraulic lines and the like. In this connection reference is made to the applicant's German patent application 10 2012 008 537.0 and international patent applications PCT/EP2012/000358 and PCT/EP2012/000719, the disclosure content whereof was fully incorporated into the disclosure of the present invention.

According to one aspect of the present invention, for actuating one or more degrees of freedom of the instrument shaft, particularly of an end effector, a drive unit is provided which in one embodiment is of modular construction, possibly having in particular a mechanical drive interface for separable connection to the drive train assembly. In the present case, modular construction is understood to mean that the unit of modular construction can be handled as a unit, or as a component unit, and in particular can be connected with other parts, or separated from them, many times, and preferably has a housing of its own.

In a further development, an instrument assembly includes two or more modular drive units which can be selectively connected to the same instrument shaft, and/or two or more instrument shafts which can be selectively connected with the same modular drive unit. In particular, the mechanical drive interfaces of one or more modular drive units and the drive train assemblies of one or more instrument shafts can be built to match to one another and to be connectable, in particular complementary or congruent, for example having cooperating coupling means.

A drive unit has, in a further development, a drive part with one or more drives, which in particular have at least one motor, in particular an electric motor, a gear train, a current sensor, reference and end switches and/or a position and/or force sensor which can determine a position of a drive shaft or a force acting upon a drive shaft, and an electronic part with one or more control and/or communication means. A control means can in particular be configured for control of the drive part, particularly of its drive(s), a communication means for communication with the drive part, particularly its drive(s) and/or sensor(s), and/or for communication with a robot of the robot assembly, particularly of an (instrument) control. Accordingly, an electronic part can in particular have or constitute the entire drive, particularly power electronics of one or more drives of the drive part or a portion thereof. Additionally or alternatively, an electronic part can have or constitute one or more signal processing means, particular for sensor signals of the drive part.

According to one aspect of the present invention, the electronic part of one or more drive units of the instrument assembly is modular and has an interface for separable, particularly electrical and/or mechanical connection with a drive part of the respective drive unit, an interface for preferably separable, particularly electrical and/or mechanical connection with the instrument shaft, and/or an interface for preferably separable, particularly electrical and/or mechanical connection with the robot assembly.

Additionally or alternatively, the drive part of one or more drive units of the instrument assembly can also be modular and have an interface for separable, particularly electrical and/or mechanical connection to an electronic part of the respective drive unit, an interface for preferably separable, particularly electrical and/or mechanical connection with the instrument shaft, particularly its drive train, and/or an interface for preferably separable, particularly electrical and/or mechanical connection with the robot assembly.

Due to this subdivision of the mechatronic drive unit into an electronic part and a drive part, of which at least one is of modular construction, is accordingly also called hereafter the electronic module or drive module, and has an interface for separable connection with the other of the electronic and the drive unit, weight and volume of the components to be handled by OR personnel can be advantageously reduced and the operator friendliness of the robot system improved. For example, an electronic module can be handled independently of the instrument with a drive part permanently or separably attached to the instrument and for example can be attached in advance to the robot or (initially) remain on the robot upon removal of the instrument.

A high count of electrical contacts between the two modules can result from the separation of all electronic component assemblies from the motors and sensors of the drive module. Consequently, in one embodiment, one or more control and/or communication means, in particular electronic component assemblies, can also be located in the drive module. In particular, the number of lines can be reduced by integration of the power electronics and/or of the current control into the drive module according to a further development of the present invention.

An interface of the electronic module can, in one embodiment, constitute in particular the mechanical and/or electrical instrument interface for attaching the instrument through the electronic module to a robot of the robot assembly. In particular, the electronic module can be or become attached permanently or separably to the robot, so that its interface for connecting to the drive part and/or to the instrument shaft constitutes an instrument interface. If the electronic module is separably attached through an interface with the robot, this constitutes an (additional) instrument interface for attaching the instrument through the electronic module to the robot.

In one embodiment, the electronic module is made sterilizable, for example by hermetically accommodating, in particular moulding-in, its control and/or communication means except for the interface(s). Additionally or alternatively, it can be entirely or partially surrounded by a sterile shell, which in a further development can also completely or partially surround the robot with which the electronic module is connected.

According to one aspect of the present invention, one or more modular manual operating units are provided for optionally replacing a modular drive unit of an instrument of the instrument assembly of the surgical robot system. By optional replacement is meant in particular, in the present case, that a manual operating unit is optionally attached to the instrument, in particular to its instrument shaft, instead of a motorized drive unit, or that at least one drive and at least one operating unit are so matched to one another that they can be mutually substituted.

In particular, a manual operating unit can have a mechanical drive interface for connection to a drive train assembly of the instrument, which corresponds to a mechanical drive interface of the drive unit to be optionally replaced for connection with that drive train assembly. In other words, the instrument assembly according to this aspect of the invention can have at least one manual operating unit and at least one modular drive unit, the mechanical drive interfaces of this match one another. The mechanical drive interfaces of the operating unit and drive unit to be optionally connected separably to the instrument and can in particular have respective coupling means for connection with the drive train assembly, which match one another in their operation, geometric configuration and/or arrangement relative to one another or to an attachment means for separable attachment of the operating or drive unit to the instrument.

The mechanical drive interfaces of the operating or drive unit can also match one another in the number of degrees of freedom that can be actuated by them, particularly in the number of coupling means, particularly shafts. Likewise it is possible that different degrees of freedom of the instrument, particularly a different number of degrees of freedom, can be actuated by the operating unit and the drive unit, for example, insofar as, at the position of one or more axes of the drive train assembly, no coupling means is provided at the mechanical drive interface of the operating unit or of the drive unit, these axes of the drive train assembly are idled, so to speak, when the operating or drive unit is attached, and are blocked in one, particularly a predefined, position in one embodiment. In a further development, the ability to actuate one or more degrees of freedom of the drive train assembly by means of the manual operating unit can be optionally blocked, preferably in that a corresponding operating degree of freedom of the operating unit or a corresponding axis, particularly mechanical, of its mechanical drive interface is optionally blocked, in particular mechanically, hydraulically or electromagnetically. In one embodiment, the operating unit has for this purpose a blocking device with mechanical elements with which individual parts of the mechanical drive interface, particularly coupling means, can be fixed in a predefined position.

One advantage of robot-controlled instruments is the possibility of integrating degrees of freedom into the distal end so as to achieve increased mobility in the intervention region compared to manual laparoscopic instruments. Likewise, simple operation of the instruments is made possible for the operator by robotic control and actuation of the instrument. If an instrument originally designed for manual operation is connected to a robot and is actuated with the help of its degrees of freedom and/or an instrument-specific drive unit, conversion to manual operation technology and continuing the operation with the same instrument is possible in the event of malfunction.

According to the aforementioned aspect of the present invention, an instrument can be used advantageously with a robot-optimized interface in that the mechanical drive interface of the manual operating unit for connection with a drive train assembly of the instrument structurally emulates or corresponds to the mechanical drive interface of the motorized drive unit. In this manner, a human operator interface is provided for a robot-controlled instrument with distal kinematics. This can result in particular in the advantage of a simpler construction of the drive unit, a better scalability with regard to the distal kinematics and a consistent control design.

In a further development, the mechanical drive interface of the manual operating unit can also have electrical contacts through which in particular information can be exchanged between the operating unit and the instrument and/or energy can be transmitted between the operating unit and the instrument, for example from or to a sensor in an end effector of the instrument shaft.

According to one embodiment, a manual operating unit has a base which has an attachment means for separable attachment to one or various instruments of the instrument assembly, and on which is mounted a hand lever with one or more degrees of freedom, the actuation whereof is transmitted, scaled in particular, to the mechanical drive interface of the operating unit, so as to thus actuate the drive train or the degrees of freedom of the instrument or instrument shaft separably connected to the operating unit. By scaled transmission is meant in particular transmission wherein a linear or rotary operating path is amplified or reduced and/or kinematically transformed, in particular into another axis and/or from a translational into a rotary or from a rotary into a translational motion. The attachment means of the base can be configured to cooperate with a, particularly complementary attachment means of the instrument shaft, for example in the form of a plug, interlocking and/or screw connection.

According to one aspect of the present invention, the instrument interface for attaching one or more instruments of the instrument assembly to the robot assembly has a mounting barrier which is releasable by a drive unit of this instrument, particularly by a drive unit attached to the instrument shaft, preferably only by a drive unit that is correctly attached to the instrument shaft and/or functional.

In this way, the robot can be prevented from controlling a non-functioning instrument.

The mounting barrier can, in one embodiment, operate mechanically and/or electromagnetically, having for example a movable protrusion or bar, which in the extended state positively prevents attachment to the robot assembly. The mounting barrier can, in one embodiment, be actuated by the drive unit, mechanically or by sensor actuation, for example by a protrusion of the drive unit operating a lever of the mounting barrier or the drive unit being detected by a sensor of the mounting barrier, particularly by means of a mechanical switch, inductively, capacitively, optically and/or using RFID. To this end, at least one drive unit can have an RFID transponder, the mounting barrier an RFID reader.

Additionally or alternatively to a mounting barrier, the robot assembly can have a presence detector for detecting the presence of a drive unit on a robot-controlled instrument. To this end a sensor, particularly a mechanical, inductive, capacitive, optical and/or RFID sensor or reader can be provided, in particular preferably on a robot, particularly at an interface of the robot for connection of the instrument interface of the instrument.

According to one aspect of the present invention, an instrument magazine is provided for storing one or more instruments of the instrument assembly, so that, particularly during OR operation, instruments of the instrument assembly that are optionally not used or not robot-controlled can be stored or stowed, in particular instruments equipped with a modular drive unit. Additionally or alternatively, the instrument magazine can be configured to store one or more instrument shafts and/or modular drive units of the instrument assembly separately or isolated from one another. In one embodiment, the instrument magazine can be configured as a translational and/or rotary substitution magazine which, by translational and/or rotary motion, can selectively position different instruments at the same location for accommodation by a robot of the robot assembly.

By means of an instrument magazine, the robot assembly can, particularly during an operation, be easily equipped with different instruments. To this end, a contact surface of the instrument magazine is preferably configured sterile or sterilizable for storing the instrument assembly, or encased in a sterile shell. In this connection, the robot of the robot assembly preferably carries out automatically the application or removal of an instrument into or from the instrument magazine, respectively, so that, advantageously, no additional auxiliary device or no additional robot is needed for changing the instrument.

In a further development, the instrument magazine has a power supply means for contacting or non-contacting power supply to one or more instruments or drive units stored in the magazine. Contact-free power supply can for example be accomplished by means of a transformer magnet arrangement without a closed iron core, wherein the power supply means and drive unit(s) have primary and secondary coil(s). Power transmission can preferably be accomplished in the medium-frequency range. In one embodiment, rechargeable energy storage units of the drive units can be charged, by means of contacting or contact-less power supply to drive units stored in the instrument magazine. Accordingly, in one embodiment of the present invention, one or more drive units of the instrument assembly have rechargeable energy storage units.

Additionally or alternatively to supplying power, at least two of the instrument magazine, the instrument assembly and the robot assembly, particularly the instrument magazine and the instrument assembly, can have a communication means for uni- or bidirectional wired or wireless, particularly inductive or radio-based, communication between at least two of the instrument magazine, the instrument assembly and the robot assembly, particularly between the instrument magazine and the instrument assembly. In particular, at least one of the instrument magazine, the instrument assembly and the robot assembly can have a sender and at least one other of the instrument magazine, the instrument assembly and the robot assembly can have a receiver. A status of the instruments stored in the instrument magazine can thereby be queried and/or such instruments initialized, (re)calibrated and/or reset. In particular, therefore, the instrument magazine and the instrument assembly, the instrument magazine and the robot assembly, in particular a control of the robot assembly, and/or the instrument magazine and the robot assembly, particularly a control of the robot assembly, can have the same or different communication means, particularly one or more of the previously described communication means.

For power supply to drive units positioned on a robot controlled-instrument, these are, in one embodiment, connected with a stationary power source through a sterile cable connection. Additionally or alternatively, a contact-free power supply can be provided, as described previously with reference to power supply to drive units stored in an instrument magazine and by way of example also in EP 2 396 796 A1 and EP 2 340 611 A1, the disclosure content whereof is completely incorporated into the disclosure of the present invention. As described previously, additionally or alternatively to a power supply, a uni- or bidirectional signal transmission can be provided between a drive unit of a robot-controlled instrument and an instrument control, which is generally considered to be a part of the robot assembly. Additionally or alternatively, as described previously, a power and/or signal transmission can also be provided through an interface of the robot assembly and an interface of the electronic and/or the drive part connected with it. Consequently, according to one aspect of the present invention, the surgical robot system can generally have a sterile cable connection, an interface connection or a wireless power and/or signal transmission means for power and/or signal transmission between the instrument assembly and the robot assembly or an instrument magazine.

It is likewise possible to supply a drive unit of a robot-controlled instrument through its instrument interface with the robot.

Particularly in the latter case, upon changing an instrument or a drive unit from an instrument magazine on or at a robot and the reverse, i.e. upon connecting or removing the instrument or the drive unit, its power supply is interrupted. For this case in particular, one or more drive units, according to one aspect of the present invention, each have an electrical energy storage unit for at least temporary autonomous power supply to the drive unit. The energy storage unit is preferably so configured that it can supply power to at least a control and/or communication means of an electronic part of a drive unit, at least during a changeover period, or that it can supply a control and/or communication means with power for at least 10 seconds and/or for at most 5 minutes.

In a further development it is also possible to so dimension the energy storage unit that it can autonomously supply the drive unit with power, particularly during an operation or for at least 30 minutes and/or for at most 5 hours. In this manner, a cable-connected power supply to the instruments, with consequent space constraints and/or interferences, can advantageously be dispensed with.

According to one aspect of the present invention, the surgical robot system has a first communication channel and one or more additional communication channels between the robot assembly, particular an instrument control, and one or more instruments of the instrument assembly. Reliability of operation in particular can be increased thereby.

In a further development, one or more of these additional communication channels operate on other physical carriers or media than the first communication channel, so as to be not only redundant but also diverse from it. For example, one of the first and an additional communication channel can be configured current- or voltage-based, the other of the first and the additional communication channel electromagnetic, optical, inductive or capacitive. At least one additional communication channel is preferably so configured, according to the de-energize-to-trip principle, that a loss of a signal on this communication channel is identified as an error. At least one additional communication channel can in particular be configured for transmitting only status information. Preferably, the robot assembly and/or the instrument assembly, particularly the robot-controlled instrument assembly is safely shut down if an error signal is transmitted on at least one additional communication channel, this being understood to also mean generally, as described earlier, the complementary loss of a release signal. In one embodiment, the presence of an instrument equipped with a drive unit can be transmitted or detected by means of the first and/or an additional communication channel.

According to one aspect of the present invention, a surgical robot system has a single- or multipart, particularly optical and/or acoustic, display for displaying a status of an instrument of the instrument assembly, particularly a changeover status and/or operating status. By changeover status is meant in particular, in the present case, the status of an instrument which is to be changed over, i.e. attached to a robot of the robot assembly or separated from it. By operating status is meant in particular, in the present case, the status of an instrument, which describes its operational readiness, particularly its (remaining) lifespan, and/or its prior operating record, in particular its cumulative operating time or its cumulative number of uses.

In this manner a clear and rapid overview can be made available to the OR personnel of which instruments are to be changed next or are available.

One aspect of the present invention relates to a method for, particularly selectively, equipping a robot assembly of a surgical robot system according to the invention with one or more instruments of the instrument assembly and/or for, particularly selectively, equipping one or more such instruments with a drive unit.

According to one embodiment, the method includes registration of an instrument by a modular operating unit during coupling or connection of this operating unit with the instrument, in particular the instrument shaft. The registration can in particular occur automatically. In the process, in a further development, particularly following establishment of a mechanical connection between the instrument and the drive unit, coupling with an instrument of the drive unit is detected and a registration procedure for concretely defining the connected instrument is activated. The instrument can actively identify itself or actively transmit signals or data to the drive unit, or be passively identified.

In one embodiment, the instrument data registered in the drive unit, for example an identification number and/or specification of the instrument shaft, perhaps its degrees of freedom and/or kinematic parameters, particularly individual calibration data, are transmitted to the robot assembly or its instrument control, preferably during registration or following connection to a robot.

In one embodiment, data of registered instruments are stored in the robot assembly, particularly its instrument control, particularly in a database, and preferably updated periodically or on an event-driven basis.

In one embodiment, one or more instruments, particularly instrument shafts, of the instrument assembly are stored in an instrument magazine without a drive unit, the application of the drive unit to an instrument occurring during the changeover process. For this purpose, in a further development, the instrument magazine has a drive unit manipulator for handling the drive unit during the instrument change. The drive unit manipulator preferably has no degrees of freedom of its own—with the exception of a tensioning mechanism for the drive unit; all positioning movements are carried out by the instrument-controlling robot(s) of the robot assembly. The number of drive units and/or the total number of the actuated degrees of freedom contained in the robot system can thereby be reduced. In addition, this concept can reduce the expenditure for power supply to the drive units, as no power supply is required for the instruments without drive units stored in the magazine; in one embodiment, power supply to the drive unit need only be ensured for the period wherein it is not adapted to the manipulator arm and supplied with power from there. The power supply to the drive unit during this period can be accomplished in particular through the drive unit manipulator.

In order to be able to handle different drive units, the drive unit manipulator can optionally equipped with a plurality of grippers, which can also have differing designs. In a further development, the drive unit manipulator has one or more translational and/or rotational degrees of freedom, so as to make available the respectively required unit.

Two or more of the aspects explained earlier and their embodiments and developments can be advantageously combined with one another.

BRIEF DESCRIPTION OF THE DRAWINGS

Further advantages and features will be apparent from the claims and the description of exemplary embodiments. These show, in partially schematic form:

FIGS. 6A, 6B, and 7: details for connecting the instrument of the robot surgical system according to FIG. 4, 5 in perspective view (FIG. 6) or in cross-section (FIG. 7);

FIG. 11A, 11B: an instrument of an instrument assembly according to another embodiment of the present invention in a view corresponding to that of FIG. 1 with a drive unit housing part separated from a drive train housing part (FIG. 11(*a*)) and combined with it (FIG. 11(*b*));

FIG. 12A: a robot surgical system according to another embodiment of the present invention in perspective view;

FIG. 12B: a plan view of an operating area of the robot surgical system according to FIG. 12(*a*);

FIG. 15: a sterilizable drive unit of a surgical instrument of a surgical robot system according to another embodiment of the present invention;

FIGS. 16-20, 21A, 21B, 22-24: one sterilizable drive unit each of a surgical instrument of a surgical robot system according to other embodiments of the present invention;

FIGS. 30A, 30B: the surgical robot system of FIG. 27A in another viewing direction (FIG. 30A) and without an attached drive unit (FIG. 30B);

DETAILED DESCRIPTION

Figure 1:
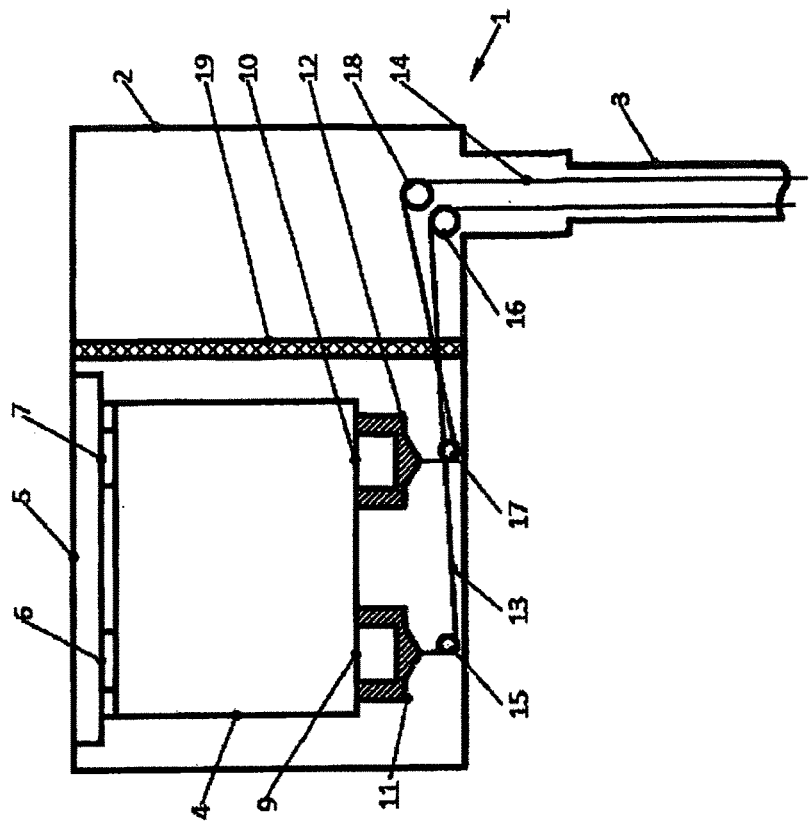
FIG. 1: an instrument of an instrument assembly according to one embodiment of the present invention.

FIG. 1 shows an instrument 1 of an instrument assembly according to one embodiment of the present invention in cross-section, with an instrument housing 2, having an instrument shaft 3, a drive train housing part built integral with it, in which a drive train assembly 11 through 18, explained in more detail later, is positioned, and a drive unit housing part with a hollow space built integrally therewith, in which a drive unit 4 is accommodated. A cover-like seal 5 provides a sterile seal for an insertion opening of the hollow space. A dynamic sterile barrier 8, through which the drive train assembly can be actuated, provides sterile separation between the hollow space and the surroundings. In one variation, a degree of freedom, actuated and/or rotary in particular, can be provided or configured between the instrument housing 2 and the instrument shaft 3.

The drive unit 4 provides the mechanical drive power for all active degrees of freedom of the surgical instrument 1. It is positioned on the proximal end of the instrument, and is designed as an independent module, the connection whereof to the instrument can be released. The number of active degrees of freedom, range of motion and power data are of universal design, so that the drive unit is replaceable and is suited for driving various instruments. Likewise it is conceivable to make available different drive units, for example to be able to use special instruments, with a large number of active degrees of freedom or other peculiarities, with the robot system.

The drive unit 4 is positioned in the desired position on and attached to the surgical instrument using a drive interface. It also includes a plurality of separable couplings which establish the flow of force between the individual drives of the drive unit and instrument-side drive trains of the drive train assembly. The separable couplings in the drive interface can be designed for turning, or rotary or for translational positioning motions; arbitrary combinations of the two principles are also possible.

A robot surgical system usually includes a few non-sterile components, for example a robot (arm) and the drive unit. These components are isolated from the sterile components of the robot surgical system, so as to prevent contamination of the operating area. In one embodiment, a static sterile barrier is implemented as a single-use film sleeve.

In the embodiment of FIG. 1, the instrument 1 and the drive unit 4 form an integral unit during an operative intervention. In the process, the drive unit 4 is positioned with a lateral offset with respect to the longitudinal axis (vertical in FIG. 1) of the instrument shaft 3, hereafter also called the shaft axis for the sake of brevity, and isolated from the sterile portion of the instrument 1 by a separate dynamic sterile barrier 8. Consequently the separable instrument interface also acts simultaneously as a sterile barrier between the non-sterile drive unit 4 and the sterile instrument 1. The separate dynamic sterile barrier 8 can be removed from the instrument 1 after an intervention and be configured as a single-use item or as a re-processable component.

At the proximal end of the instrument 1 is located the housing 2, in the drive shaft housing part whereof the drive trains of the kinematics and of the end effector are housed, which are located on the distal end of the instrument shaft 3. The integrally constructed drive shaft housing part has a hollow space for accommodating the non-sterile drive unit 4. The seal cover 5 isolates the non-sterile drive unit 4 from the sterile portion of the instrument 1. Mechanical mounting of the drive unit 4 in the housing 2 can for example be accomplished using attachment means or elements 6, 7 located on the seal cover. These elements can for example be implemented as linear or visco-elastic springs, and thus generate a preload force between the cover and the drive unit. Additionally or alternatively, the drive unit 4 can be positively mounted in the housing 2 with tensioning or latching mechanisms.

The hollow space in the housing 2 is sterile prior to the insertion of the drive unit 4, but it is contaminated by the insertion of the non-sterile drive unit 4. Consequently, in this embodiment, a separate sterile barrier 8 is integrated between the drive unit 4 and the bottom of the hollow space, which isolates or separates the contaminated hollow space from the sterile remainder of the instrument 1. The dynamic sterile barrier 8 contains a plurality of motion transmission elements for the individual drives 9 and 10 of the drive unit, which can be designed as rotary and/or linear drives. When inserting the drive unit into the housing 2, the individual drives 9 or 10 are connected with instrument-side coupling elements 11 or 12 respectively, and through them by means of traction cables 13, 14 with the distal instrument kinematics and the distal end effector (not shown). In the exemplary embodiment, the traction cables 13, 14 actuating the instrument kinematics and the end-effector are guided through pulleys 15 and 16, or 17 and 18 respectively, into the instrument shaft.

In the schematic view of the embodiment of FIG. 1, the drive unit 4 is inserted proximally, or from the side facing away from the instrument shaft 3, into the hollow space of the housing 2. Alternatively, instruments are also conceivable wherein the drive unit 4 is inserted distally, or from the side facing the instrument shaft 3, or laterally, through the outer surface of the housing 2.

Figure 2:
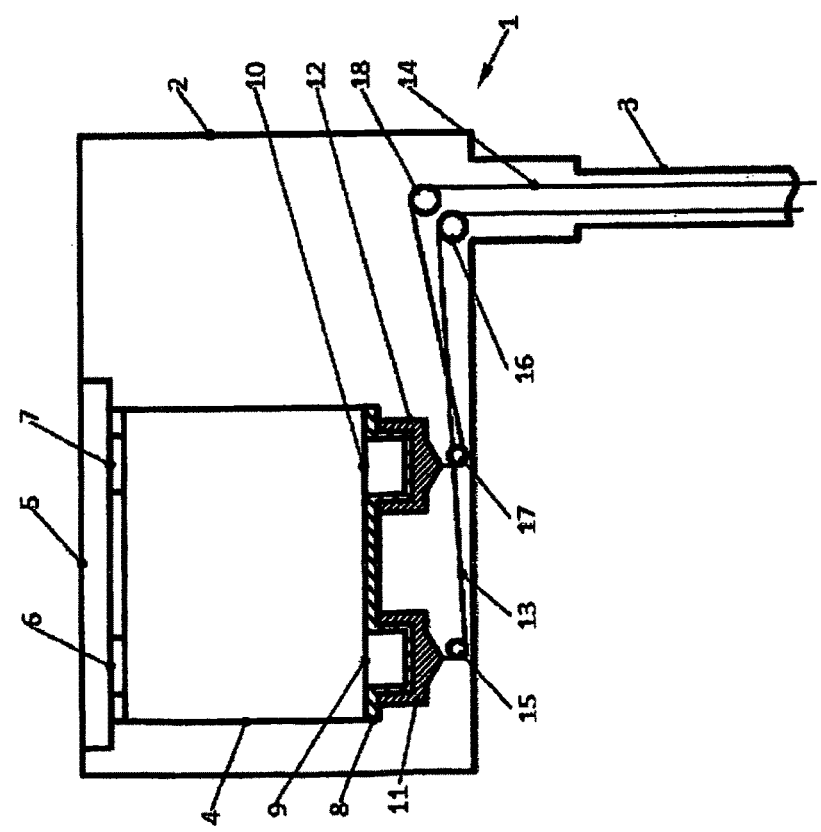
FIG. 2: an instrument of an instrument assembly according to another embodiment of the present invention in a view corresponding to that of FIG. 1.

FIG. 2 shows an instrument of an instrument assembly according to another embodiment of the present invention in a view corresponding to that of FIG. 1. Corresponding elements are designated with identical reference symbols, so that for this purpose, reference is made to the foregoing description and only the differences are discussed hereafter.

In the embodiment according to FIG. 2, the sterile barrier 19 is integrated into the instrument for isolating the non-sterile drive unit 4 from the sterile instrument, and is thus processed together with the instrument. The hollow space in the housing 2 is sterile prior to insertion of the drive unit 4, but it is contaminated by the insertion of the non-sterile drive unit 4. Consequently a dynamic sterile barrier 19 is integrated into the housing 2, which isolates the contaminated hollow space from the sterile portion of the instrument 1. The integrated dynamic sterile barrier 19 can, for example, have gap or labyrinth seals or contacting seals, through which the instrument-side drive trains, here their traction cables 13, 14 are guided. As in the embodiment of FIG. 1 with the separate, replaceable dynamic sterile barrier 8, the drive train assembly can consequently be actuated through the dynamic sterile barrier; in particular, the forces and motions can be transmitted through the dynamic sterile barrier, while it provides sterile separation between the hollow space contaminated by the non-sterile drive unit 4 and the sterile surroundings.

Figure 3:
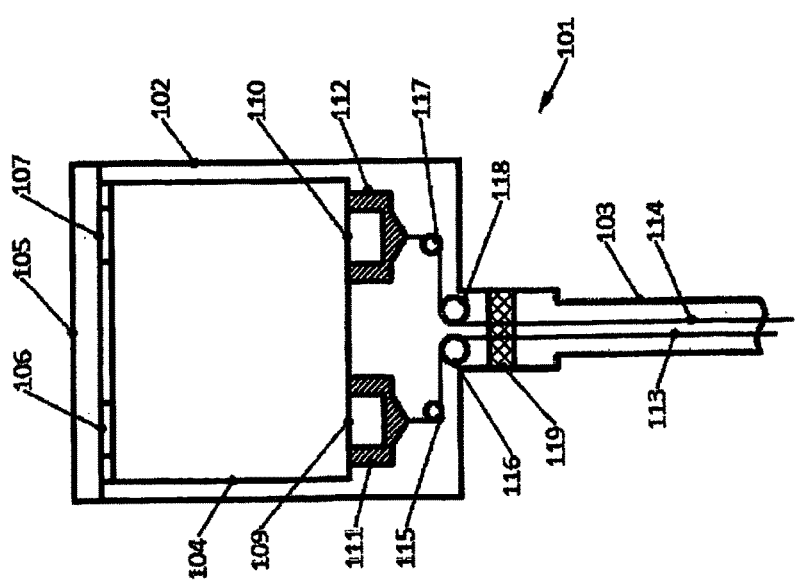
FIG. 3: an instrument of an instrument assembly according to another embodiment of the present invention in a view corresponding to that of FIGS. 1, 2.

FIG. 3 shows an instrument of an instrument assembly according to another embodiment of the present invention in a view corresponding to that of FIGS. 1, 2. Corresponding elements are designated with identical reference symbols, so that for this purpose reference is made to the foregoing description and only the differences are discussed hereafter.

In the embodiment according to FIG. 3, a housing 102 is located on the proximal end of the instrument 101 with an instrument shaft 3, a drive train housing part built integrally with it, in which are housed the drive trains of the kinematics and the end effector which are located at the distal end of the instrument shaft 103, and a drive train housing part built integral with it with a hollow space for accommodating a non-sterile drive unit 104. A seal cover 105 isolates the non-sterile drive unit 4 from the sterile portion of the instrument 101 or the surroundings, or seals off the hollow space in sterile fashion. Mechanical mounting of the drive unit 104 in the housing 102 can for example be accomplished with one or more attachment means or elements 106, 107 located on the seal cover 105. These elements can for example be configured as linear or visco-elastic springs and thus generate a preload force between the cover and the drive unit. Additionally or alternatively, the drive unit 104 can be positively mounted inside the housing 102 with tensioning or latching mechanisms.

The drive unit has a plurality of individual drives 109 and 110, which can be configured as rotary and/or translational or linear drives. When inserting the drive unit into the housing 102, the individual drives 109 or 110 are connected with the respective instrument-side coupling elements 111 or 112, and through their traction cables 113 and 114 with the distal instrument kinematics and the distal end effector (not shown).

In the embodiment of FIG. 3, the instrument kinematics and the end effector are actuated with the traction cable 113 and 114, which are guided by pulleys 115 and 116 or 117 and 118 respectively into the instrument shaft. The hollow space in the housing 102 is sterile prior to insertion of the drive unit 104, but it is contaminated by the insertion of the non-sterile drive unit 104. Consequently, a sterile barrier 119 is integrated into the housing, which isolates the contaminated hollow space from the sterile portion of the instrument 101 or from the surroundings. The integrated dynamic sterile barrier 119 can be integrated, as explained previously with reference to FIG. 2, in the form of gap or labyrinth seals or as contacting seals of the instrument-side drive trains for example.

Figure 4:
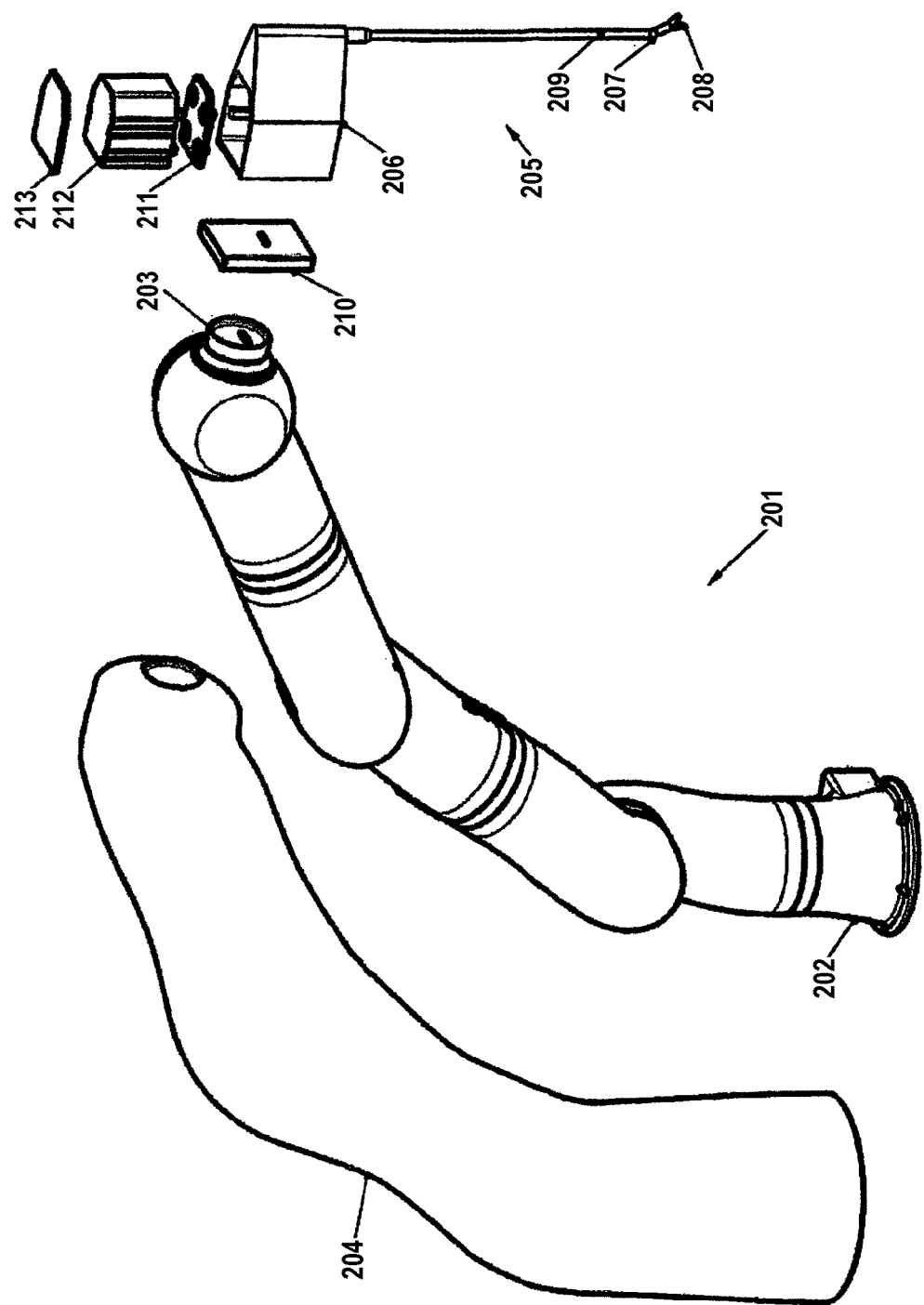
FIG. 4, 4A: a robot surgical system according to one embodiment of the present invention with the instrument of FIG. 1 in perspective exploded view.
Figure 4A:
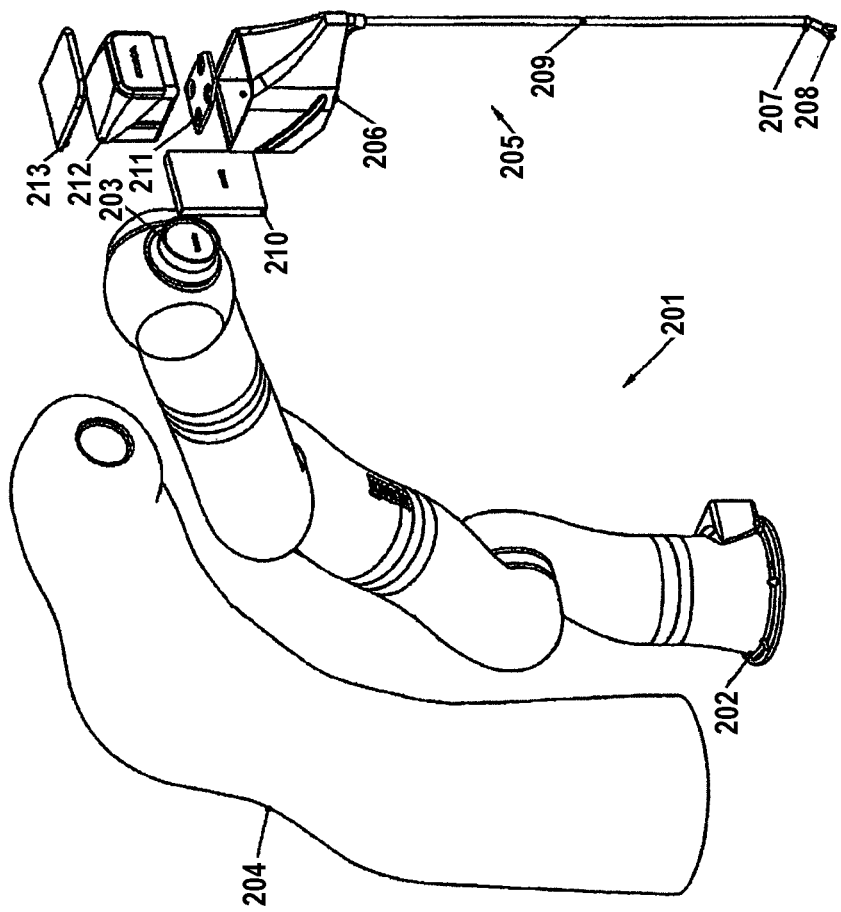
Figure 7:
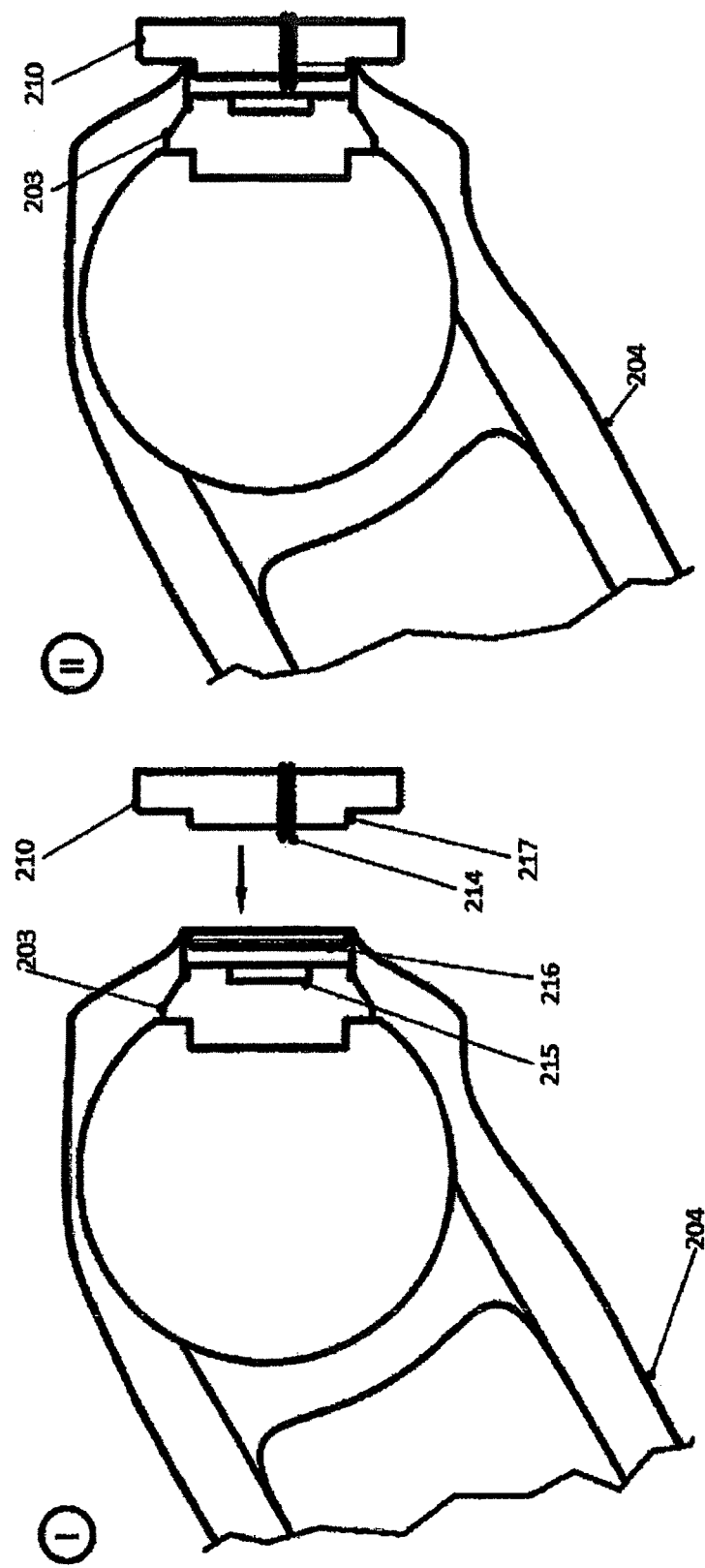

FIG. 4 shows a robot surgical system according to one embodiment of the present invention with the instrument of FIG. 1, in perspective view, FIG. 4 the robot surgical system in the assembled state, FIGS. 6A, 6B, and 7 details regarding connection of the instrument in perspective view (FIGS. 6A, 6B) and in cross-section (FIG. 7).

The robot surgical system has a robot or manipulator arm 201, the proximal base 202 whereof can be mounted relative to a patient (not shown). The manipulator arm contains preferably 6 or more actuated joints, so as to be able to freely position the distal end 203 of the manipulator arm 201 in space. The manipulator arm 201, including its distal end 203, is surrounded by a static sterile barrier in the form of a sterile shell 204 so as to prevent contamination of the sterile operating area by non-sterile robot components. A surgical instrument 205 is mounted onto a distal end 203, thus encased in sterile fashion, by means of a sterile electromechanical interface, hereafter also called the instrument adapter 210.

The surgical instrument 205 corresponds to the instrument 1 previously described with reference to FIG. 1, so that reference can be made to its description for additional information.

At the proximal end of the instrument 205 is located an instrument housing 206, which has a mechanical interface to the instrument adapter 210. In the exemplary embodiment shown, an instrument shaft 209 is located distally on the housing 206, which bears distal instrument kinematics 207 and a surgical end effector 208 and is made integrally with a drive unit housing part and a drive train housing part made integrally therewith, or is separately mounted on the drive train housing part. The drive unit housing part and the drive train housing part together constitute the one-piece instrument housing 206 of this embodiment.

In the exemplary embodiment of FIGS. 4, 4A, 5-7, the drive unit 212 is proximally inserted into the housing 206 together with a separate dynamic sterile barrier 211. A seal cover 213 isolates the non-sterile drive unit 212 from the sterile operating area.

A detail view of a possible embodiment of the connection between the sterile instrument adapter 210 and the distal end 203 of the manipulator arm 201, by which an airtight separation of the manipulator arm 201 from the sterile operating area is achieved, is shown in FIGS. 6A and 6B. In addition, this embodiment is distinguished by an especially simple embodiment of the sterile shell 204, which can be made from a thin-walled film sleeve, made of plastic film for example. The encasing of the distal end 203 of the manipulator arm 201 is preferably made as a thin-walled formed plastic part, so as to simplify the application of the sterile shell 204 onto the manipulator arm 201. This formed part can for example be made of a deep-drawn or blow-moulded plastic film and is then welded to the thin-walled film sleeve. Due to the simple manufacture of the sterile encasement 204, running costs to the user for single-use items are reduced. As the drive unit 212 is not located inside the sterile shell 204 in the exemplary embodiments according to the invention, no transmission of the drive motions through the sterile shell 204 to the instrument 205 is necessary.

If electrical signals and power required for operation and for control need to be routed to the drive unit 212 and consequently through the sterile shell 204, a plurality of sockets 215 are integrated into a recess 216 at the distal end 203 of the manipulator arm 201. Similarly, a plurality of contact pins 214 are integrated into a radial protuberance 217 of the sterile instrument adapter 210. The recess 216 and the radial protuberance 217 between the distal end 203 of the manipulator arm and the sterile instrument adapter 210 constitute a mechanical plug connection, the sockets 215 and contact pins 214 an electrical connection of the electromechanical interface 210.

The mechanical plug connection 216, 217 is designed as a form-fitting connection wherein the wall thickness of the static sterile barrier constituted by the sterile shell 204 lying in between is taken into account, so as to achieve the most exact and tilt-resistant connection possible between the sterile instrument adapter 210 and the distal end 203 of the manipulator arm 201. Furthermore, the connection between the interface 216 and 217 leads the electrical connection between the contact pins 214 and the sockets 215. Due to the prior mechanical routing of the insertion components 203 and 210, the connection of the electrical contacts 214 and 215 is considerably simplified and consequently more robust under field operating conditions. In order to make the sterile shell 204 as simple and as cost-effective as possible, no electrical contacts are integrated. The electrical contact between the contact pins 214 and the sockets 215 are created by the contact pins perforating the sterile shell 204 at the contact sites during insertion of the sterile instrument adapter 210 at the distal end 203. To this end, the contact pins 214 are pointed at the end that is inserted into the sockets 215. FIG. 7 clarifies the insertion procedure of the sterile instrument adapter 210 onto the distal end 203 of the sterile-encased manipulator arm 201.

Figure 13:
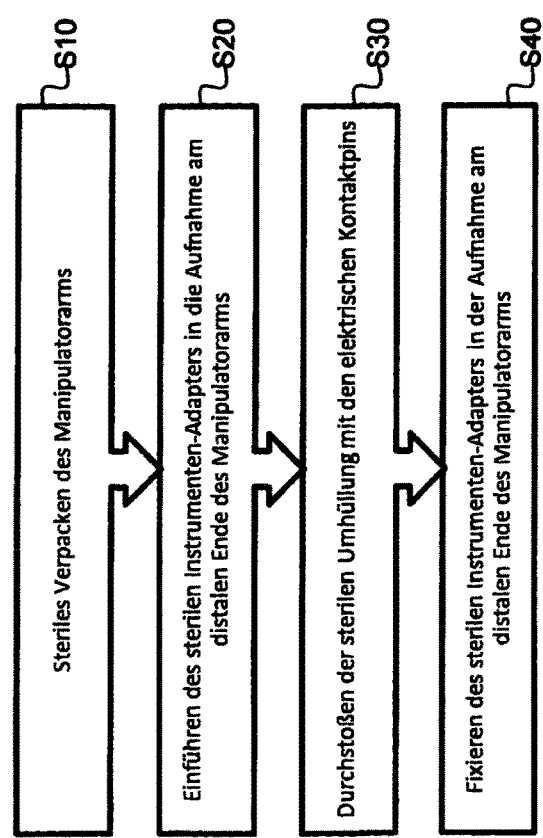
FIG. 13: a method for assembling the robot surgical system according to FIGS. 4 through 7.

FIG. 13 shows a method for assembling the robot surgical system described earlier:

First, the manipulator arm 201 is packed in sterile fashion with the sterile shell 204 (step S10). Then the sterile instrument adapter 210 is inserted with its radial protuberance 217 into the recess 216 at the distal end 203 of the manipulator arm 201 and a mechanical plug connection of the electromechanical interface 210 is thus established (step S20, FIG. 7, left or "I"). The leading mechanical plug connection 216, 217 provides sufficient guidance of the sterile instrument adapter 210 into the correct orientation relative to the distal end 203 of the manipulator arm 201, so that the static sterile barrier in the form of the sterile encasement 204 is perforated by the contact pins 214 and the electrical contact is generated between the contact pins 214 and the sockets 215 (step S30). Finally, the sterile instrument adapter 210 is mechanically mounted in the accommodation 215 at the distal end 203 of the manipulator arm 201 (step S40; FIG. 7, right or "II"). This can be accomplished by means of a screw connection for example, the sterile shell 204 being perforated by the screw as described in connection with the contact pins 214.

The assembly of the electromechanical interface 210 on the robot was explained above. The electromechanical interface 210 can also be positioned on the drive unit housing part in identical or similar fashion. For example, this can have a sterile barrier in the form of a through opening which is provided with a sterile seal by a lip seal, and which is perforated by contact pins of the interface 210 when it is connected by means of a plug connection with the drive unit housing part.

Prior to a robot surgical intervention, all required instruments are first prepared and each equipped with its own drive unit. In the process, the instruments are not allowed to be contaminated by the non-sterile drive units.

Figure 5:
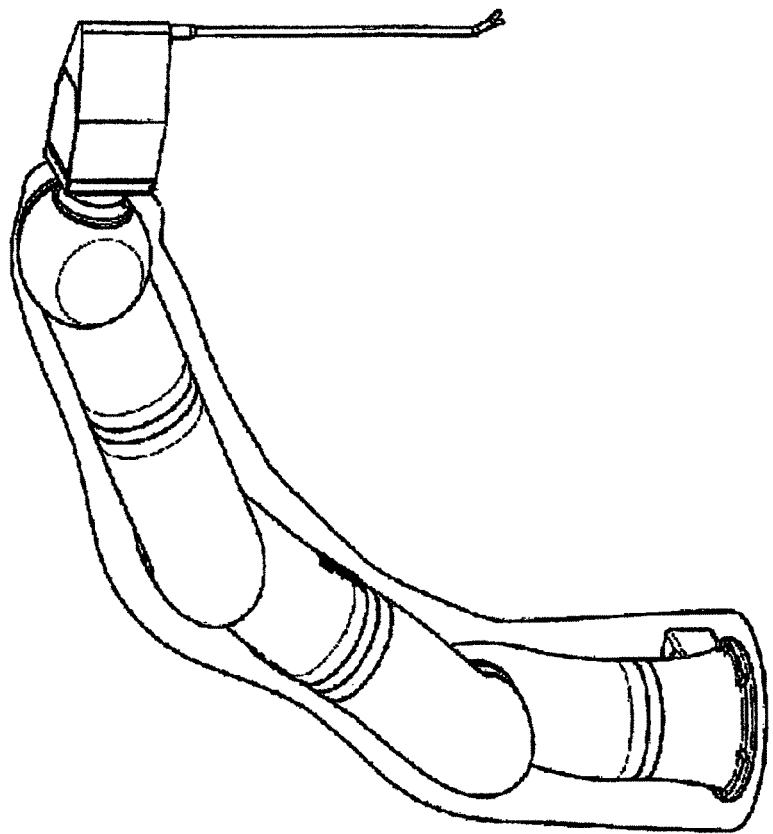
FIG. 5: the robot surgical system according to FIG. 4 in the assembled state.
Figure 8:
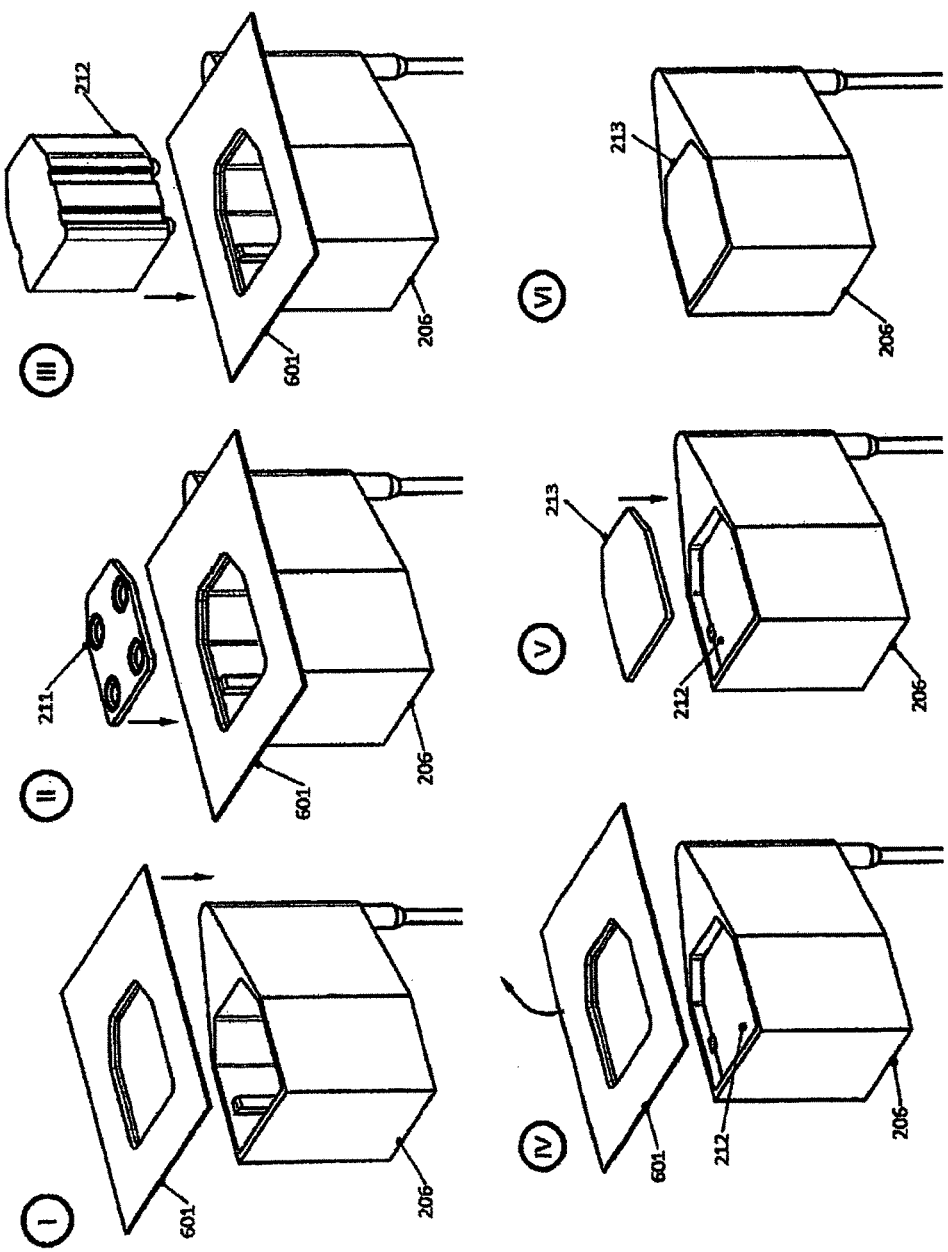
FIG. 8: a method according to one embodiment of the present invention for assembling an instrument assembly according to FIGS. 1, 4 and 5.
Figure 14:
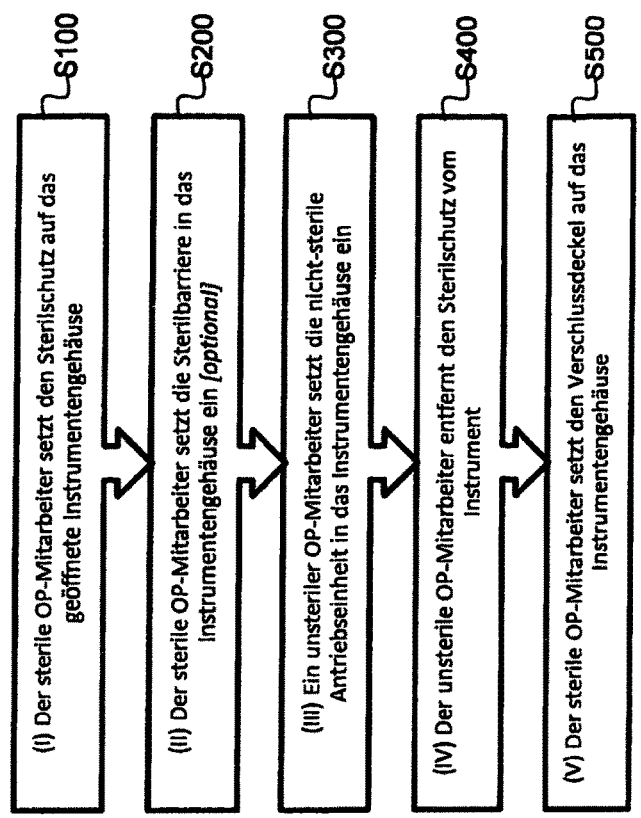
FIG. 14: the sequence of the method according to FIG. 8.

FIG. 8 shows in a figure sequence, FIG. 14 in a flow diagram, a method according to an embodiment of the present invention for assembling the instrument assembly of FIG. 1, 4 or 5, particularly for equipping with a drive unit. The instrument of FIG. 8 corresponds to the instrument 1 of FIG. 1 or 205 of FIGS. 4, 5.

For inserting the drive unit, two persons are advantageous:
A sterile OR worker for handling the instruments and for carrying out "sterile manipulations,"
A non-sterile OR worker for handling the drive unit and for carrying out all "non-sterile manipulations."

Prior to installation of the drive unit, all required components are pre-positioned, the non-sterile drive unit 212 being pre-positioned separately from the sterile components (instrument, separate dynamic sterile barrier 211, seal cover 213, sterile protection 601), so as to avoid contamination. Provided that seal cover 213 is an integral component of the instrument 201, the sterile OR worker opens the seal cover 206 on the proximal instrument housing 206, before the drive unit is inserted. Alternatively, the seal cover 213 can be removable from the proximal instrument housing 206. In this case, it is set aside by the sterile OR worker. Alternatively, the seal cover 206 can also be pre-positioned separately from the instrument 201.

In step S100 (see FIG. 14; FIG. 8: "I"), the sterile OR worker sets the sterile protection 601 on the opened proximal instrument housing 206, so as not to contaminate the sterile instrument 201 when inserting the drive unit 212. In step S200 (FIG. 8: "II"), the sterile OR worker inserts the sterile barrier 211 into the proximal instrument housing 206. This process step is required only in the case of a separate dynamic sterile barrier (see 8 in FIG. 1; 211 in FIG. 8) and is dispensed with in the case of an integrated sterile barrier (see 19 in FIG. 2; 119 in FIG. 3). Following this preparatory work, the non-sterile OR worker, in step S300 (FIG. 8: "III") can insert, and mount if applicable, the drive unit 212 into the proximal instrument housing 206. Next, the non-sterile OR worker, in S400 (FIG. 8: "IV"), removes the sterile protection 601 from the proximal instrument housing 206. Finally, the sterile OR worker sets the seal cover 213 on the proximal instrument housing 206 (FIG. 14: S500; FIG. 8: "VI"). The non-sterile drive unit 212 is thereby enclosed in the proximal instrument housing 206.

Figure 9B:
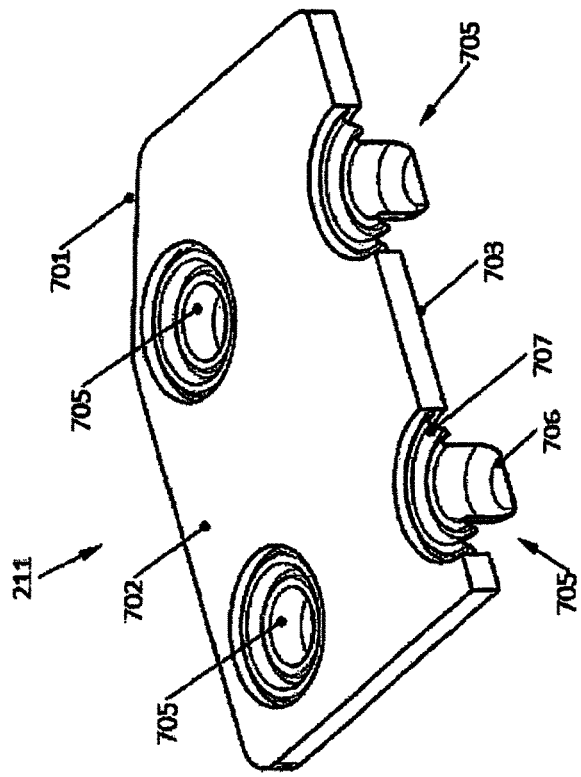
FIGS. 9A, 9B: a dynamic sterile barrier of the instrument assembly according to FIGS. 1,4 and 8.
Figure 9A:
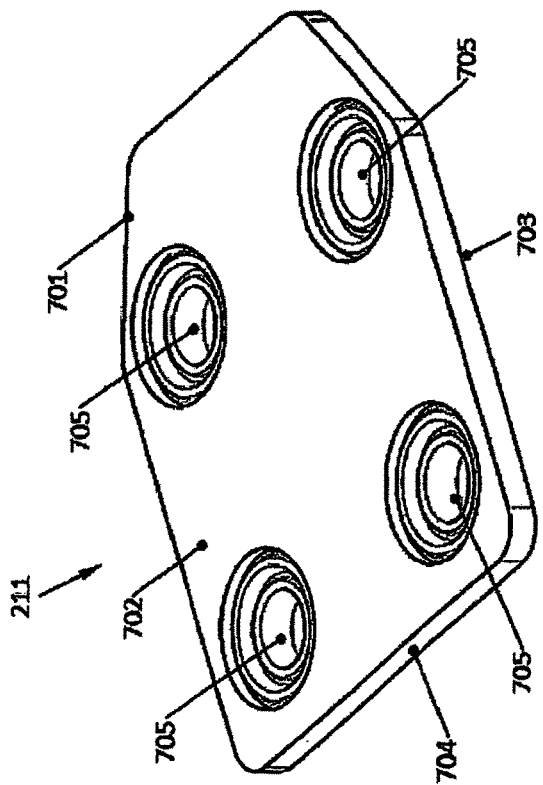

FIG. 9A shows in a perspective full view, and in a sectional view (FIG. 9B) a dynamic sterile barrier of the instrument assembly according to FIGS. 1, 4 and 8. The sterile barrier 211 of FIGS. 9A and 9B corresponds to the sterile barrier 8 of FIG. 1 or 211 of FIG. 8. It consists of a rigid intermediate plate 701, on the side 702 whereof rests the drive unit. The side 703 facing the side 702 lies on the bottom surface of the hollow space in the proximal instrument housing 206. The outer dimensions of the rigid plate 702 are somewhat offset with respect to the boundary of the hollow space in the proximal instrument housing 206, so as to be able to manually insert the sterile barrier without great effort. So as to achieve better isolation or sterile sealing off of the drive unit 212 from the sterile portion of the instrument, a circumferential contacting seal (not shown) can alternatively be integrated on the side 703 or the circumferential surface 704 of the rigid plate 702. Such a seal can in particular have a seamless foamed-in-place seal, of polyurethane for example, and/or an annular elastomer seal, particularly an O-ring, seal lip or the like.

Apertures are provided in the rigid plate 701 corresponding to the number of actuated degrees of freedom or drive trains. In each of these apertures is integrated one motion transmission element 705, which couples an individual drive of the drive unit 212 to the associated instrument-side drive train while ensuring sterility. The right portion of FIG. 9 shows a section through the sterile barrier 211, so as to clarify a possible embodiment of a motion transmission element 705 for linear positioning motions. In the example shown, the motion transmission element 705 is configured as a thin-walled membrane structure. The coupling elements of the individual drive are positioned in a cylindrical eversion 706 in the centre of the motion transmission element 705. The instrument-side coupling element 11 (see FIG. 1) surrounds, in the coupled state, the eversion 706. In order to make possible for the eversion 706 to move in a direction normal to the rigid plate 701, the eversion 706 is fastened with an elastic membrane 707 into the aperture of the rigid plate. This separate dynamic sterile barrier is consequently designed to be movable.

One advantage of a replaceable instrument drive is the possibility of being able to also use instruments with variant requirements for the drive unit (number of actuated degrees of freedom, positioning forces, etc.) when necessary. So as to rule out incorrect operation and damage to the instruments, a confusion-proof design of the drive units is proposed.

Figure 10C:
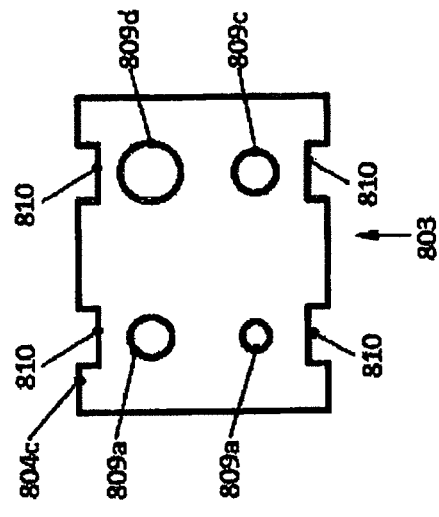
FIGS. 10A, 10B, 10C: various mechanical codings of drive units of the instrument assembly according to one of FIGS. 1 through 8 and 11(*a*), 11(*b*)
Figure 10B:
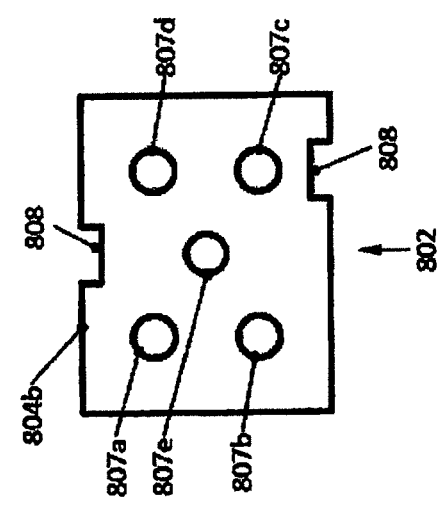
Figure 10A:
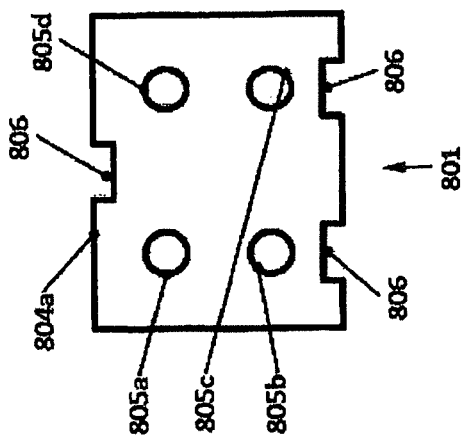

FIGS. 10A, 10B, and 10C show various mechanical codings of drive units of the instrument assembly according to one of FIGS. 1 through 8 and 11A, 11 B, so as to prevent confusion of individual drive units. The figure shows views of three drive units 801, 802, 803 from the direction of the coupling elements of the individual drives. The drive units 801, 802, 803 correspond for example to the drive unit 4 of FIG. 1, 2 or 3, 212 of FIG. 4 and 8 or 914 of FIGS. 11A, 11B.

They differ in the configuration of the individual drives. By way of example, drive unit 801 (FIG. 10A) has individual drives 805a, 805b, 805c, 805d. Drive unit 802 (FIG. 10B) has by way of example individual drive 807a, 807b, 807c, 807d, 807e. Drive unit 803 (FIG. 10C) has by way of example individual drive 809a, 809b, 809c, 809d.

In order to rule out confusion of the drive units during installation in an instrument, the housings 804a, 804b and 804c of drive units 801, 802 and 803 respectively have different mechanical coding 806, 808 and 810 respectively. In the example shown, the mechanical codings 806, 808, 810 are each implemented as a combination of one or more grooves, which extend in the direction of insertion of the drive units 801, 802, 803 into the proximal instrument housing 206. Due to the different groove patterns 806, 808, 810, confusion of the drive units is ruled out.

FIGS. 11A, 11B show an instrument of an instrument assembly according to another embodiment of the present invention in a view corresponding to that of FIG. 1, with a drive unit housing part separate from a drive train housing part (FIG. 11A) or joined to it (FIG. 11B). The instrument can correspond with the embodiments described above except for the differences explained hereafter, so that reference can be made in this connection to their description and only differences are described hereafter.

In this embodiment, the drive unit housing part constitutes, with the drive unit, an independent functional unit and can, if necessary, be separated during operation from the remainder of the instrument, particularly the drive axes housing part. For the drive unit, a sterilizable and multiply re-usable drive unit housing part is provided, which is easier for OR personnel to handle than a sterile shell in the form of a thin film sleeve. Alternatively, the sterile drive unit housing part can also be designed as a single-use item. Unlike the embodiments described above, separation of the drive unit housing part with the drive unit and the rest of the instrument, in particular the drive axes housing part, is possible, so that a drive unit can be used for different instruments during an operation.

FIGS. 11A, 11B show the structure of the functional units of the instrument 901 that can be separably joined together, namely the separate drive unit housing part 902 with the drive unit 914 (left in FIG. 11A) and the drive axes housing part 903 (right in FIG. 11A).

The drive axes housing part 903 is integrally formed at the proximal end of the instrument shaft 904, or joined to it, particularly separably. Positioned in the drive axes housing part 903 are the drive trains of the kinematics and of the end effector, which are located at the distal end of the instrument shaft 904. The drive axes housing part 903 has an adapter 905 for accommodating the drive unit 914 packaged under sterile conditions by the drive unit housing part 902. In the drive axes housing part 903, a plurality of coupling elements 906, 907 and traction cables 908, 909 of instrument-side drive trains are provided, which couple the respective individual drives of the drive unit 902 with the distal instrument kinematics or the distal end effector. Besides the coupling elements 906, 907, and traction cables, the drive trains have pulleys 910 through 913, by which these are guided into the instrument shaft 904.

The drive unit housing part 902 has a non-sterile drive unit 914, which is housed in a sterile housing 915 made of a rigid material. Advantageous materials for the sterile housing 915 are in particular corrosion-resistant steels, titanium or medical-grade thermoplastic or thermosetting plastics. A seal cover 916 isolates the non-sterile drive unit 914 from the sterile operating area. Mechanical mounting of the drive unit 914 in the sterile housing 915 can for example be accomplished using one or more attachment means or elements 917 located on the seal cover 916. These elements can for example be configured as linear or visco-elastic springs, and thus generate a preload force between the cover and the drive unit. Additionally or alternatively, the drive unit 914 can be positively mounted in the housing 915 using tensioning or latching mechanisms. In order to isolate the non-sterile drive unit 914 from the sterile operating area, a dynamic sterile barrier 920 is provided, which contains a plurality of motion transmission elements 921, 922 for the individual drive 918, 919 of the drive unit. The individual drives 918, 919 can be configured as rotary and/or linear drives. The sterile barrier 920 can be configured either as an integral component, not separable without destruction, of the housing 915, or as a separate component removable by the user and separably connected with the housing 915. It can be configured as a single-use item or as a re-processable component. The housing 915, the seal cover 916 and the dynamic sterile barrier 920 together constitute the drive unit housing art 902, which accommodates the non-sterile drive unit 914 under sterile conditions. This can for example, as described earlier with reference to FIGS. 8, 14, be placed in the drive unit housing part 902.

FIG. 11B shows the drive unit housing part 902 with the drive axes housing part 903 connected to the instrument 901. Motion transmission from the drive unit 902 to the drive trains 906 through 913 is accomplished by connecting the individual drives 918, 919 with the respective instrument-side coupling elements 906, 907 by or through the motion transmission elements 921, 922. Coupling of the drive unit 914 to the instrument-side drive trains is accomplished during installation of the drive unit housing part 902 to the adapter 905.

In the embodiment of FIGS. 11A, 11B, the adapter 905 for the drive unit housing part 902 is located for example on the drive axes housing part 903. Alternatively, instruments 901 are also conceivable wherein the adapter 905 is located distally or laterally. Additionally or alternatively, the confusion-proof configuration of the drive units explained with reference to FIG. 10 can be provided in this embodiment: here the mechanical coding can be provided either solely on the housing 915 or both on the drive unit 914 and also on the housing 915.

In this embodiment, as in the embodiments of FIGS. 1, 2, 4 through 11, the drive unit is positioned with a lateral offset relative to the shaft axis. Consequently, reference is again made to the remaining description. As shown with reference to FIG. 3, however, a drive unit coaxial with the instrument shaft 904 is also fundamentally possible.

FIG. 12A shows a robot surgery system according to another embodiment of the present invention in perspective view, FIG. 12B a plan view on its operating area.

In this embodiment, the radial dimensions both of the instrument and of the manipulator arm in the region of the instrument shaft are minimized. With this measure, the collision risk in multi-arm applications or with several robots cooperating can be reduced. For the user, this means increased flexibility in trocar placement and/or smaller trocar spacing.

In order to reduce spacing, the drive unit of the instrument is positioned with a lateral offset relative to the shaft axis. Thus the bulkier components of the robot system, particularly the distal end of the manipulator arm, the drive unit, mechanical interfaces to the instrument can be positioned outside the narrower interaction radius of the manipulator arm. FIG. 12A shows by way of example an application with three manipulator arms or robots. Each of the manipulator arms 1101, 1102 and 1103 bears at its distal end a surgical instrument 1104, 1105 and 1106 respectively, each having a drive unit at its proximal end, which is laterally offset from the longitudinal axis of the instrument shaft 1107, 1108 and 1109 respectively. From the deployment of the manipulator arms 1101, 1102, 1103 relative to the operating area 1114 and the proximal dimensions of the instruments 1104, 1105, 1106 result the penetration points of the instruments 1110, 1111, 1112 of the instrument shafts 1107, 1108, 1109 through the abdominal wall 1113. FIG. 12B shows the minimum spacing 1115, d(min, 1) of the penetration points 1110, 1111, 1112 resulting from this arrangement.

FIG. 15 shows a sterilizable drive unit of a surgical instrument of a surgical robot system according to one embodiment of the present invention.

The sterilizable drive unit has an actuator assembly with one or more actuators in the form of force- and/or position-controlled electric motors, of which two are shown by way of example in FIG. 15, the drive axes whereof are designated 1A and 1B respectively. In the exemplary embodiment, these drive axis 1A, 1B are actuatable in translation (vertical in FIGS. 1 through 25), for example by the electric motors having suitable conversion gearing for converting rotary into translational drive motion, or are configured as linear electric motors.

The actuator assembly is separably coupled by means of an interface with an instrument shaft of the surgical instrument of the surgical robot system (not shown). The interface has a shell 100 (see FIG. 25), which seals penetration openings 3.1 of a housing 3 of the drive unit fluid-tight and encases a part of a drive axis 1A, 1B of the actuator assembly reaching through one of these penetration openings. The shell 100 is of bellows-like configuration, or has a folding and is provided for following translational motions of the drive axes 1A, 1B. The shell 100 can be connected with the housing separably, particularly with screws, or inseparably, particularly permanently bonded, preferably by welding or gluing. Translational motions of the drive axes 1A, 1B actuate corresponding degrees of freedom of an end effector of the instrument shaft (not shown).

The drive unit also has a component assembly with a plurality of electronic components consisting of position sensors for determining positions of the actuators, of which two position sensors 2A, 2B are shown by way of example in FIG. 15. The drive unit can optionally contain other electronic components or component assemblies, particularly for signal detection, signal conditioning and/or processing, for controlling the motors and/or for communication with a higher-level control.

The actuator assembly and the component assembly are positioned inside the sterilizable housing 3, which has two separably connectable housing parts consisting of a housing vessel 3.2 and a cover 3.3 screwed fluid-tight to it, between which is positioned an O-ring seal.

The two housing parts have a dimensionally stable housing wall 3.4, which in the exemplary embodiment consists, as an outer wall, of metal and/or plastic.

On the inside of this housing wall 3.4 is placed a thermal insulation layer 4, which in the exemplary embodiment is configured as a vacuum insulation layer or has a vacuum insulation.

To this end, an inner housing wall is located parallel to the outer housing wall 3.4, or the outer housing wall 3.4 is of double-wall construction. The outer and inner housing walls delimit between them an airtight space which is filled with air under low pressure or is evacuated. The inner housing wall can optionally be dispensed with, particularly in the case where the insulation layer is configured without vacuum.

The thermal insulation layer 4 covers the inner surface of the inner housing wall 3.4 completely except for the penetration openings 3.1 (see FIG. 25) or encloses the interior of the housing with the actuator and component assemblies, at least substantially completely. In this manner, heat entry into the interior of the housing during treatment with hot steam and/or air for sterilizing the unit can be minimized and consequently a thermal overloading, in particular of the temperature-sensitive position sensors 2A, 2B, can be prevented. This insulation layer can, in one variation, have additional discontinuities, particularly for cable feedthroughs, plug connectors, electrical contacts, screwed connections or the like.

FIG. 16 shows, in a view corresponding to that of FIG. 15, a sterilizable drive unit of a surgical instrument of a surgical robot system according to another embodiment of the present invention. Matching features are designated with identical reference symbols, so that reference is made to their description and only the differences in the embodiments will be discussed.

In the embodiment of FIG. 16, the thermal insulating layer is of multilayer construction and has two layers 4.1, 4.2, of which one has in particular a barrier material, perhaps mineral wool or rigid polyurethane foam, the other possibly being configured as a vacuum insulation layer as previously described. The thermal insulation of the housing 3 can thereby be further increased.

FIG. 17 shows, in a view corresponding to that of FIGS. 15, 16, a sterilizable drive unit of a surgical instrument of a surgical robot system according to another embodiment of the present invention. Matching features are designated with identical reference symbols, so that their description is referred to and only differences between the embodiments are discussed.

In the embodiment of FIG. 17, in addition to the thermal insulation layer 4, a thermal insulation layer 5 is located on the housing wall 3.4 between the component assembly 2A, 2B and the actuator assembly, made for example in of plastic in the exemplary embodiment, with a heat conductivity $\lambda < 0.4$ W/(K m). Heat conduction from the actuator assembly to the component assembly, and consequently the impact of temperature on the component assembly, can thereby be advantageously reduced. Such an additional thermal insulating layer 5 can likewise also be provided in a multi-layer thermal insulation layer 4.1, 4.2 on the housing wall 3.4, as explained with reference to FIG. 16.

While in the embodiments of FIGS. 15 through 17 a thermal insulation layer completely covers the inner surface of the outer housing wall 3.4, except for the penetration openings 3.1, it is only placed on part or sections of the housing wall 3.4 in the embodiments explained hereafter with reference to FIGS. 18 through 25, particularly at the level of the component assembly 2A, 2B, or facing said component assembly.

FIG. 18 shows, in a view corresponding to that of FIGS. 15 through 17, a sterilizable drive unit of a surgical instrument of a surgical robot system according to another embodiment of the present invention. Matching features are designated with identical reference symbols, so that their description is referred to and only differences in the embodiments are discussed.

In the embodiment of FIG. 18, stationary heat conduction means 6 made of copper, aluminium or the like reach through the thermal insulation layer 4. They are permanently connected to the actuator assembly and have a heat dissipation surface 6.1 on the outside of the housing wall 3.4 and a heat absorption surface 6.2, bonded with it, on the inside of the housing, which can be firmly fastened, in particular integrally configured, with the attachment of the actuator assembly with the housing. In particular, the heat absorption surface 6.2 can be in contact with a housing of the electric motors, or be in heat-conducting connection with it.

Waste heat from the electric motors can be removed during operation from the sectionally thermally insulated housing interior by the heat conduction means 6. To this end, the heat dissipation surfaces 6.1 have an increased surface area with cooling ribs, fins and/or pins. The heat dissipation surfaces 6.1 can be separably connected with the heat conduction means 6.

FIG. 19 shows, in a view corresponding to that of FIG. 18, a sterilizable drive unit of a surgical instrument of a surgical robot system according to another embodiment of the present invention. Matching features are designated with identical reference symbols, so that their description is referred to and only differences in the embodiments are discussed.

In the embodiment of FIG. 19, the heat conduction means are designed to be switchable and can be switched between a first, more heat-conductive state, which is illustrated in the right half of the subdivided FIG. 19, and a second, less heat-conductive state which is illustrated in the left half of FIG. 19. The heat conduction means can for example have, or in particular be, cooling bodies 7 connected with the robot, which in the first, more heat-conductive state reach through recesses in the thermal insulation layer 4 and make contact with the housing of the electric motors (see FIG. 19, right). This contact can be automatically brought about during coupling of the drive unit to the robot. In the second, less heat-conductive state by contrast, the electric motors and the heat sinks 7 are separated by a gap (see FIG. 19, left).

Figure 20:
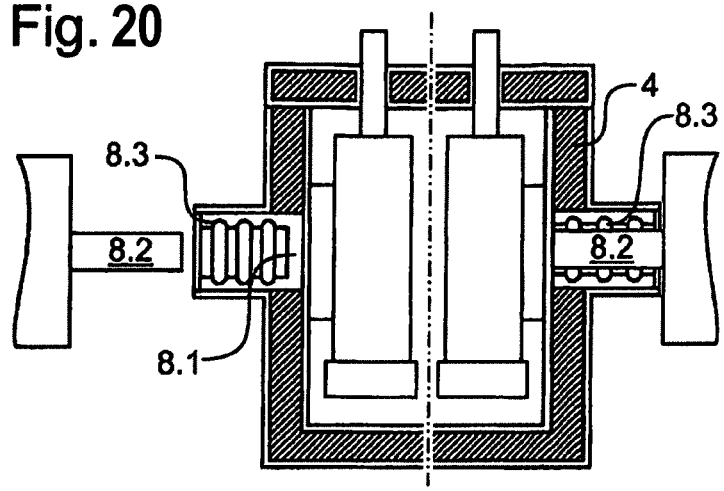

FIG. 20 shows a view corresponding to that of FIG. 19 of a sterilizable drive unit of a surgical instrument of a surgical robot system according to another embodiment of the present invention. Matching features are designated with identical reference symbols, so that their description is referred to and only differences in the embodiments are discussed.

In the embodiment of FIG. 20, the heat conduction means are also configured to be switchable and can be switched between a first, more heat-conductive state, which is illustrated in the right half of the subdivided FIG. 20, and a second, less heat-conductive state which is illustrated in the left half of FIG. 20.

The heat conduction means have a gap 8.1 in the thermal insulation layer 4 and a movable element 8.2 for selective heat-conducting bridging of this gap. The gap 8.1 is made fluid-tight and has a reduced pressure or vacuum, so as to reduce its heat conductivity. The gap is delimited by an elastic shell 8.3, which has a folding or is of bellows-like construction. In the first, more heat-conductive state (see FIG. 20, right) the movable element 8.2 bridges the gap and thus increases the heat conductivity of the heat conduction means; in the second, less heat-conductive state (see FIG. 19, left), the gap 8.1 is not bridged and thus is thermally insulating, so that the heat conduction means can be switched over by moving the movable element 8.2.

FIG. 21 shows, in a view corresponding to that of FIG. 20, a sterilizable drive unit of a surgical instrument of a surgical robot system according to another embodiment of the present invention. Matching features are designated with identical reference symbols, so that their description is referred to and only differences in the embodiments are discussed.

Figure 21A:
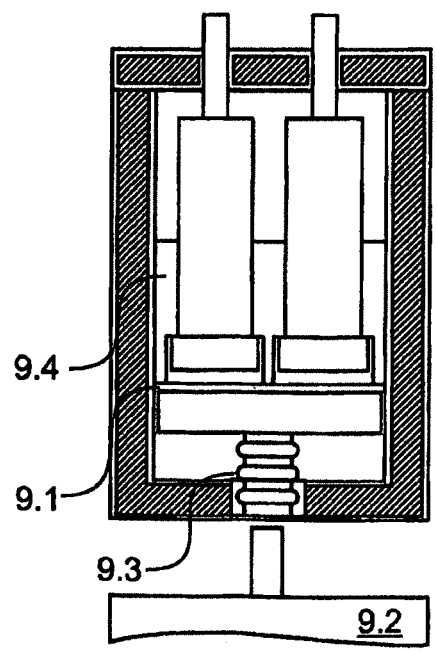
Figure 21B:
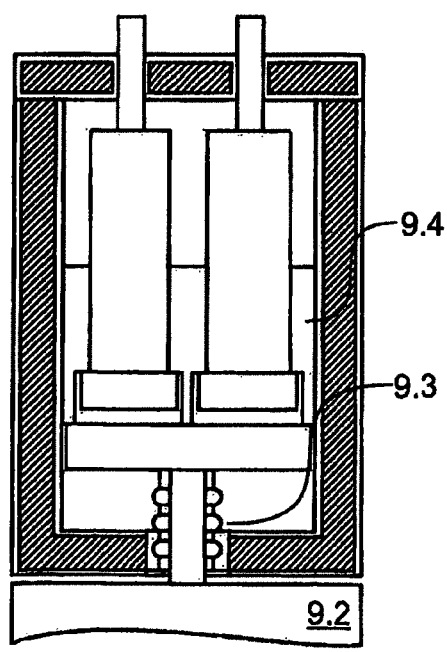

In the embodiment of FIG. 21, a heat conduction means is also configured to be switchable and can be switched between a first, more heat-conductive state, which is illustrated in FIG. 21B, and a second, less heat-conductive state which is illustrated in FIG. 21A.

Unlike the embodiment of FIG. 20, no direct contacting of the electric motor housing by the movable element is provided for in the embodiment of FIG. 21. In one embodiment of the present invention, as shown by way of example in FIG. 21, a heat collection means is generally provided (9.4, for example, in FIG. 21), which is in permanent contact with multiple, in particular all actuators of the actuator assembly, and which can be selectively contacted by a movable element 9.2

A gap 9.1 is also formed in this embodiment, which can be selectively bridged by the movable element 9.2. The gap is delimited fluid-tight by an elastic shell 9.3, which has a folding or is of bellows-like construction. In the exemplary embodiment of FIG. 21, it has no reduced pressure. In a variation, however, the interior of the housing can be evacuated, so to advantageously reduce thermal insulation of the component assembly, in which case the gap 9.1 also has reduced pressure. In general, in one embodiment of the present invention, the interior of a housing can be evacuated or be filled with air or gas under reduced pressure.

In the exemplary embodiment of FIGS. 21A, 21B, the movable element is constructed in two parts, one part, which is permanently located in the shell 9.3, being movably and captively positioned inside the housing 3, while another part can selectively contact this part and can move within the housing. The part located in the shell 9.3 is elastically pre-loaded by it away from the heat collection means 9.4 and can be moved by the other part against the heat collection means 9.4 in order to bridge the gap to it.

Figure 22:
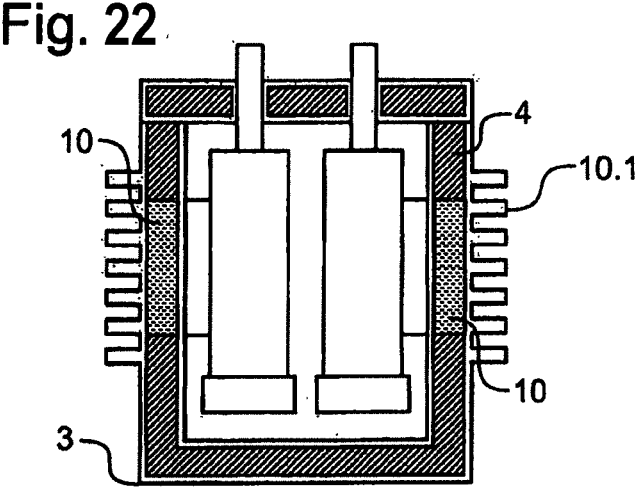

FIG. 22 shows, in a view corresponding to that of FIG. 15, a sterilizable drive unit of a surgical instrument of a surgical robot system according to another embodiment of the present invention. Matching features are designated with identical reference symbols, so that their description is referred to and only differences in the embodiments are discussed.

In the embodiment of FIG. 22, the switchable heat conduction means has a plurality of Peltier elements 10. By applying a voltage, a temperature difference, and consequently a first, more heat-conductive state, can be generated. The Peltier elements 10 have heat dissipation surfaces 10.1 which are located on the outer side of the housing 3.

Figure 23:
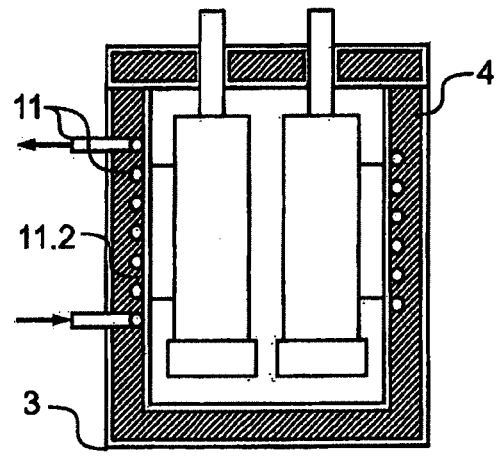

FIG. 23 shows, in a view corresponding to that of FIG. 22, a sterilizable drive unit of a surgical instrument of a surgical robot system according to another embodiment of the present invention. Matching features are designated with identical reference symbols, so that their description is referred to and only differences in the embodiments are discussed.

In the embodiment of FIG. 23, the heat conduction means has fluid passages 11 with a working fluid, for example a liquid refrigerant, which can exchange heat with a heat exchange surface (not shown) on the outer side of the housing 3 and a heat collection surface 11.2 of the heat conduction means. A flow control means for selective active streaming in the form of a controllable, selectively activatable circulation pump (not shown) can circulate the working fluid during operation between the heat collection and heat dissipation surfaces, as indicated in FIG. 23 by working fluid flow arrows.

Figure 24:
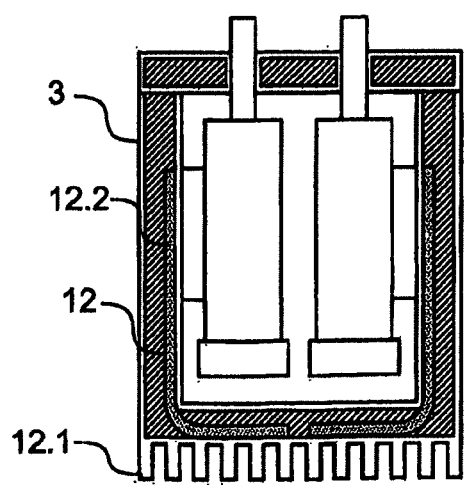
Figure 25:
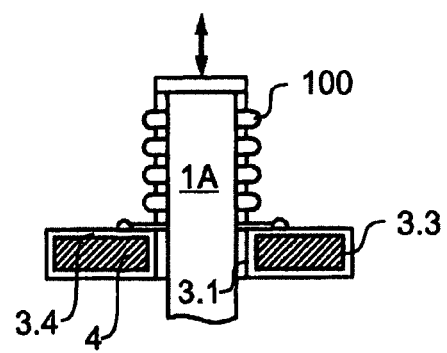
FIG. 25: a portion of the sterilizable drive unit according to one of FIGS. 15 through 24.

FIG. 24 shows, in a view corresponding to that of FIG. 23, a sterilizable drive unit of a surgical instrument of a surgical robot system according to another embodiment of the present invention. Matching features are designated with identical reference symbols, so that their description is referred to and only differences in the embodiments are discussed.

In the embodiment of FIG. 24, the fluid passages are configured as heat pipes 12 not having a circulation pump, with a working fluid which can exchange heat, with phase changes, with a heat dissipation surface 12.1 and a heat collection surface 11.2 of the heat conduction means. A flow control means for selectively blocking the working fluid in the form of a controllable valve (not shown) can, in operation, can allow or impede flow of the working fluid in the heat pipe.

For sterilizing the drive unit, as was explained earlier with reference to FIGS. 15 through 25, an outer side of the drive unit is subjected for a predetermined period of time, preferably at least 5 minutes, preferably at least 20 minutes and/or at a pressure of at least 2 bar, particularly at least 3 bar, with heated fluid, particularly steam or air, preferably at 100 degrees Celsius at least, particularly at least 120 degrees Celsius, preferably at least 130 degrees Celsius.

Switchable heat conduction means 7, 8.2, 9.2, 10, 11 and 12 are in this case switched into the second, less heat-conductive state (left in FIGS. 19, 20; FIG. 21A). In operation, a switchover means switches these over into a first, more heat-conductive state (right in FIGS. 19, 20: FIGS. 21B, 22, 23, 24). This can be accomplished manually or automatically, particularly by coupling to the robot, by which the movable elements 7, 8.2, 9.2 can be brought into contact with the actuator assembly or the heat collection means 9.4, or depending on a temperature in an interior of the housing. To this end, a switchover means (not shown) can determine a temperature inside the housing 3 and, when a predefined limiting value is exceeded, switch one or more switchable heat conduction means into the first, more heat-conductive state, activating for example a circulation pump of the embodiment of FIG. 23, a opening a valve of the embodiment of FIG. 24 or supplying current to a Peltier element of the embodiment of FIG. 22.

Figure 26:
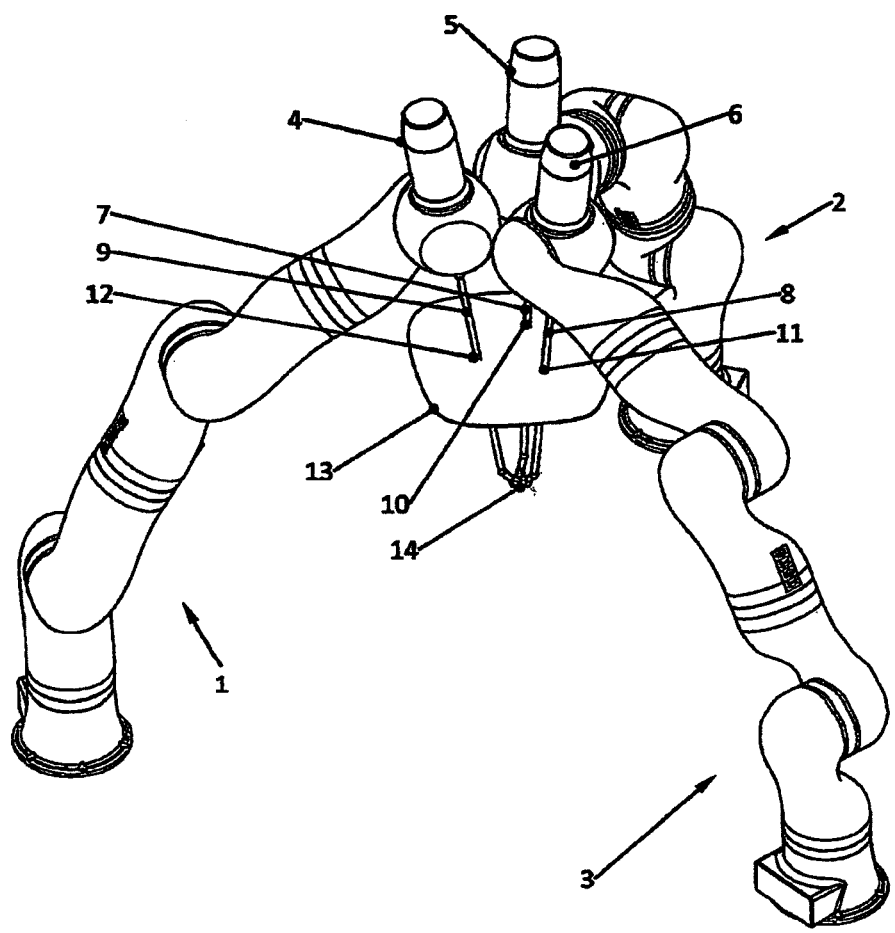
FIG. 26: a surgical robot system according to another embodiment of the present invention.

FIG. 26 shows, as preliminarily described, a surgical robot system according to one embodiment of the present invention, with a plurality of robots 1, 2 and 3, to the distal ends whereof is separably attached one instrument each, 4, 5 and 6 respectively, of an instrument assembly according to one embodiment f the present invention.

Figure 27B:
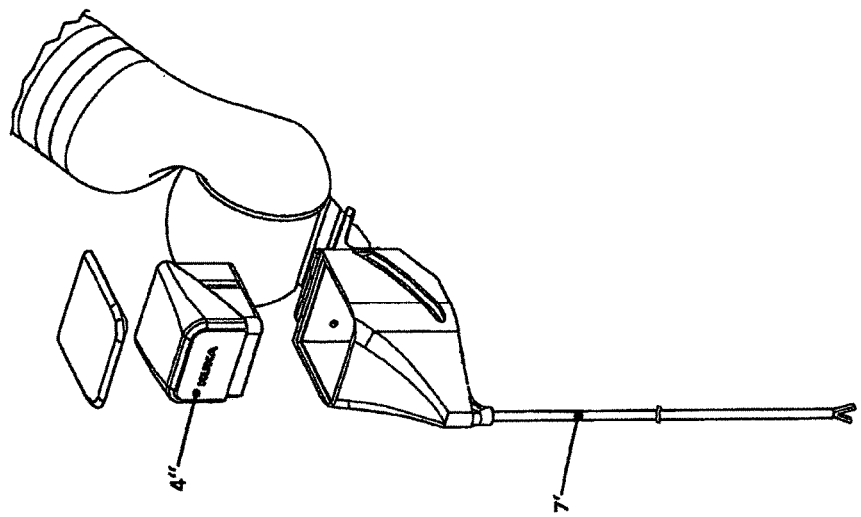
FIG. 27A, 27B: a robot-controlled instrument of an instrument assembly according to one embodiment of the present invention.
Figure 27A:
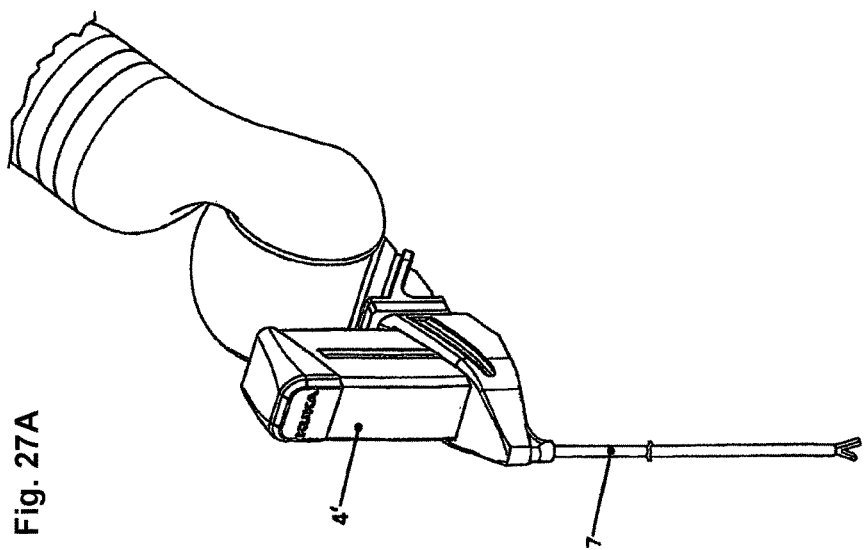

FIGS. 27A, 27B show various embodiments of a robot-controlled instrument with various drive units, which are separably attached to the surgical instrument or instrument shaft so as to ensure simple preparation and the most cost-effective possible implementation of the instrument. In the embodiment according to FIG. 27A, during the operation, the modular drive unit 4' is repeatedly separable from the instrument, or can be repeatedly applied to an instrument. To this end, the non-sterile drive unit 4' is pre-operatively [encased] with a sterile shell. Alternatively, the drive unit can also be configured as a sterilizable module, whereby the sterile encasing can be dispensed with. In contrast, in the embodiment of FIG. 27B, a non-sterile drive unit 4" is pre-operatively inserted into a proximal instrument housing of the instrument shaft 7', and this is sealed under sterile conditions. In this concept, the drive unit 4" advantageously remains in the proximal instrument housing for the entire duration of an operative intervention, and is taken out again only after its end and prior to preparation.

Optionally, an interface between the drive unit and the instrument shaft can have a mounting barrier releasable by a drive unit of said instrument, which prevents an instrument lacking a drive unit from being adapted to the robot. For example, the proximal instrument housing can have a mechanical barrier, which is deactivated or released when a drive unit is inserted. The instrument housing can only be adapted to a manipulator arm with the barrier deactivated. Alternatively or in addition to the mechanical barrier, with the drive unit not inserted, described above, the presence and/or the correct position of the drive unit on the instrument can be checked with presence sensor technology integrated between the robot and the drive unit.

Figure 28:
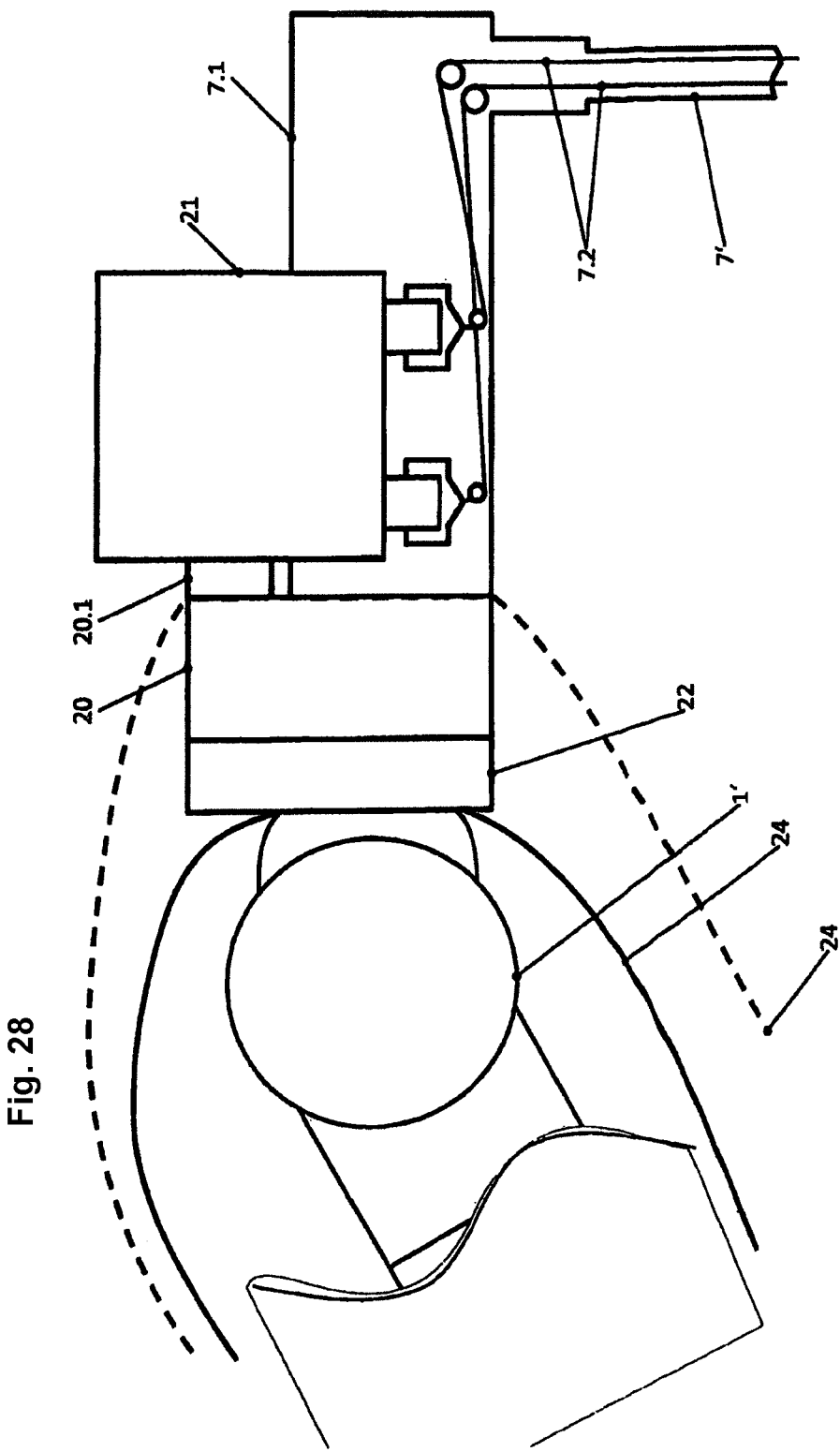
FIG. 28: a robot-controlled instrument of an instrument assembly according to one embodiment of the present invention.

FIG. 28 shows a robot-controlled instrument of an instrument assembly according to one embodiment of the present invention, with subdivision of the mechatronic drive unit into an electronic module 20 and a drive module 21. By this subdivision it is possible to handle, and in particular to apply the drive electronics to the robot, independently of the instrument drives. This reduces the weight and volume of the module to be handled by the OR personnel; user-friendliness of the system is improved.

The electronic module 20 contains, in one embodiment, the entire drive electronics, or at least a portion thereof. Thus in particular components of units needed for signal processing for sensor signals, for regulation and control of drive motors, and/or a communication interface for connecting to the robot can be contained in the electronic module. The drive module 21 contains for example a drive motor for each degree of freedom of the instrument, a reduction gear train if needed, a sensor system for speed and/or position determination, and/or other sensors, for example force sensors, moment sensors, current sensors, reference and end switches or the like.

The electronic module 20 is preferably placed with an instrument adapter 22 at the distal end of the robot 1'. The instrument adapter 22 constitutes the mechanical connection between the robot and the drive unit and ensures accurately repeatable positioning and attachment of the drive unit relative to the distal end of the robot.

Optionally, the instrument adapter 22 also constitutes the required electrical connections between the drive unit and the robot. The electronic module 20 can either be configured as a sterilizable module, or be encased by a sterile shell, which advantageously also encases the manipulator arm. By way of example, two possible routings of such a sterile shell 24 are shown, with solid and dashed lines, which encase a non-sterile electronic module 20 and a non-sterile instrument adapter 22 together with the robot 1' (FIG. 28: dashed) or, in the case of a sterile electronic module 20 and a sterile instrument adapter 22, only the robot 1' (FIG. 28: solid).

Optionally, the electronic module 20 described is also suitable for an instrument with an integrated drive part, not removable by the user. In this case, the size and costs of the instrument can be reduced by the outplacement of the entire, or of significant portions of, the drive electronics.

In FIG. 28, a proximal flange 7.1 is also indicated schematically, as well as a drive train 7.2 of the instrument shaft 7' and an electrical interface 20.1 between the electronic and the drive part 20, 21.

Figure 29:
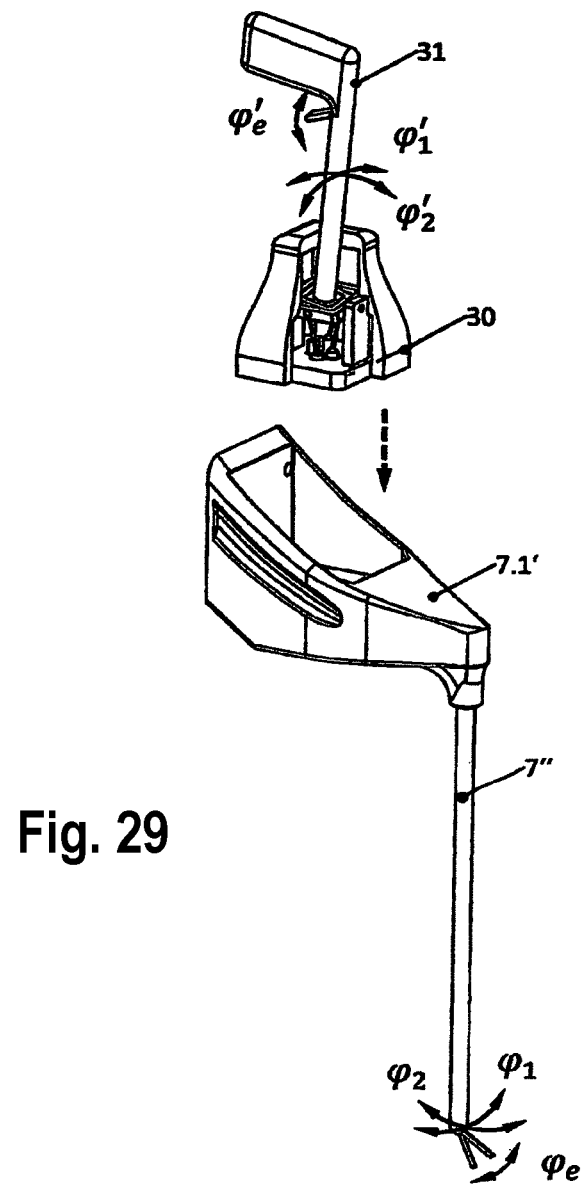
FIG. 29: a manual operating unit of an instrument assembly according to one embodiment of the present invention.

FIG. 29 shows a manual operating unit of an instrument assembly according to one embodiment of the present invention which can be attached, instead of a modular drive unit (not shown in FIG. 29; see for instance FIG. 27A, FIG. 30A), as shown for example in FIGS. 26 through 28, to the proximal flange 7.1' of the instrument shaft 7''.

The operating unit of this exemplary embodiment is configured for manual actuation of two motion degrees of freedom $\varphi_1$ and $\varphi_2$ and an operating degree of freedom $\varphi_e$ of an end effector at the distal end of the instrument shaft 7''. A hand lever 31, which is mounted in a base, or hand lever housing 30 with degrees of freedom $\varphi'_1$ and $\varphi'_2$, serves as the user interface. These degrees of freedom correspond in the embodiment shown to the distal motion degrees of freedom $\varphi_1$ and $\varphi_2$ of the instrument. In addition, another degree of freedom $\varphi'e$ is provided at the hand lever 31 for actuating the operating degree of freedom $\varphi_e$ of the distal end effector. The hand lever housing 30 has a mechanical interface (not visible in FIG. 29) for repeated separable coupling to the instrument shaft, which corresponds to the mechanical interface of the mechatronic drive unit to be replaced (not shown).

Moreover, the hand lever housing 30 contains one or more mechanisms and/or gear trains, which converts the positioning motions of the hand lever 31 into the motions provided for in the interface, optionally scaled, and connects with coupling elements of the interface. Optionally, the interface of the removable operating unit can also have electrical contacts, through which for example information is exchanged between the hand lever and the instrument and/or power is transmitted between the hand lever and the instrument.

The possibility of limiting to selected distal degrees of freedom, which can be operated by a person, is optionally provided in the operating unit. For this purpose, the interface can contain a blocking device for mechanically fixing one or more distal degrees of freedom in a predefined joint position. Preferably, the blocking device contains mechanical elements with which individual parts of the instrument-side coupling elements can be fixed in a predefined position.

Figure 30B:
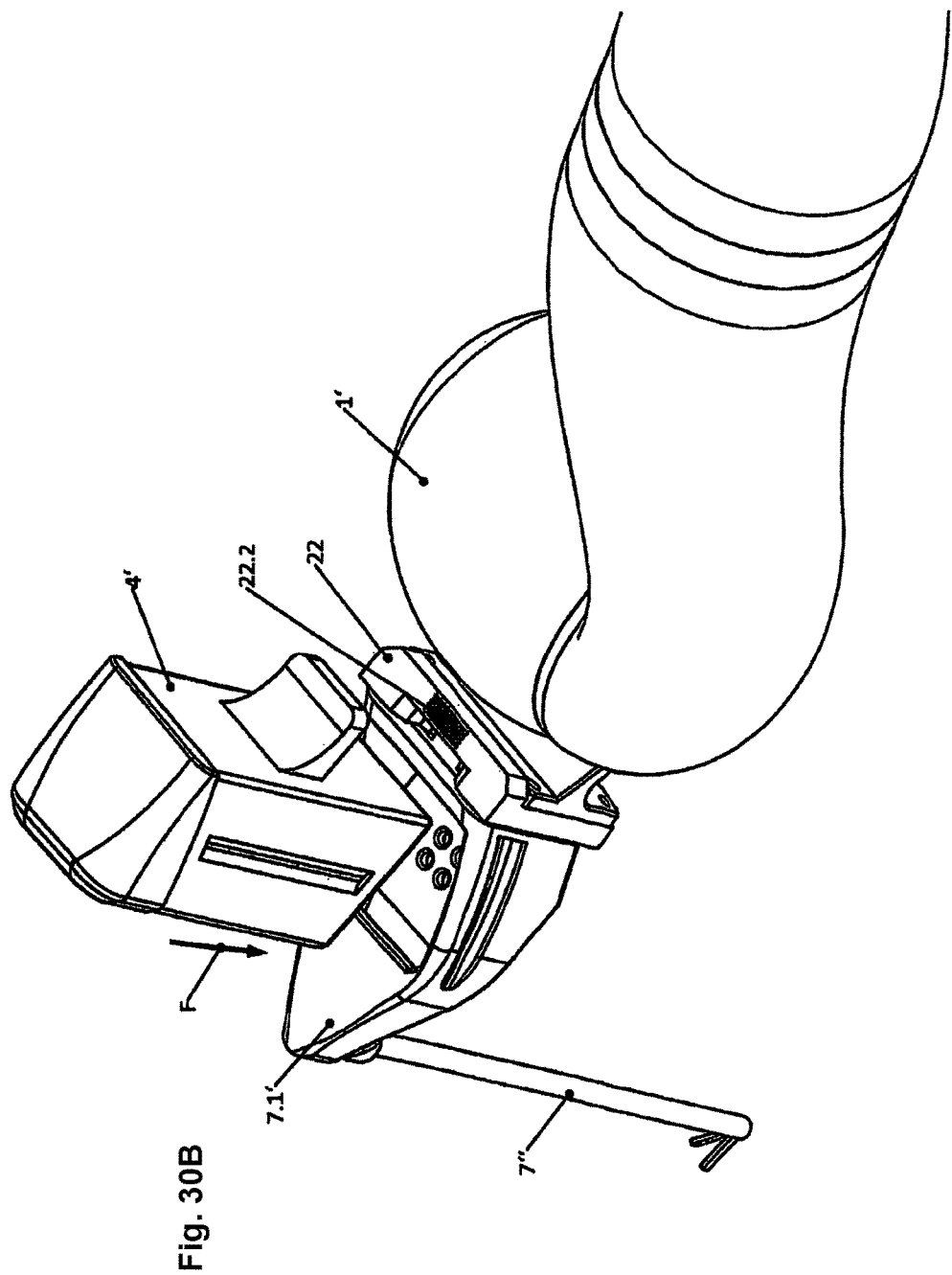

FIG. 30A shows the robot-controlled surgical robot system of FIG. 27A, equipped with the modular drive unit 4', from another viewing direction. Just as in FIG. 27 and FIGS. 31 through 33, a sterile encasement of the robot is not shown for better clarity. This encloses the robot entirely or partially, particularly part of the sterile instrument adapter. In this embodiment, the electrical interface 20.2 of the drive unit directly grasps an electrical interface 22.2 of the sterile instrument adapter 22 (see FIG. 28), so that the number of contacts to be sterilized is minimized and consequently the contact reliability can be increased. A detail view of the electrical interface 22.2 between the sterile instrument adapter and the drive unit is shown in FIG. 30B. It should be noted that the direction of insertion F of the electrical interface advantageously matches the direction of insertion of the drive unit into the sterile instrument adapter. In order to compensate for small positioning and dimensional discrepancies between the contact pairs, the electrical interface can advantageously contain devices for tolerance compensation.

Figure 31:
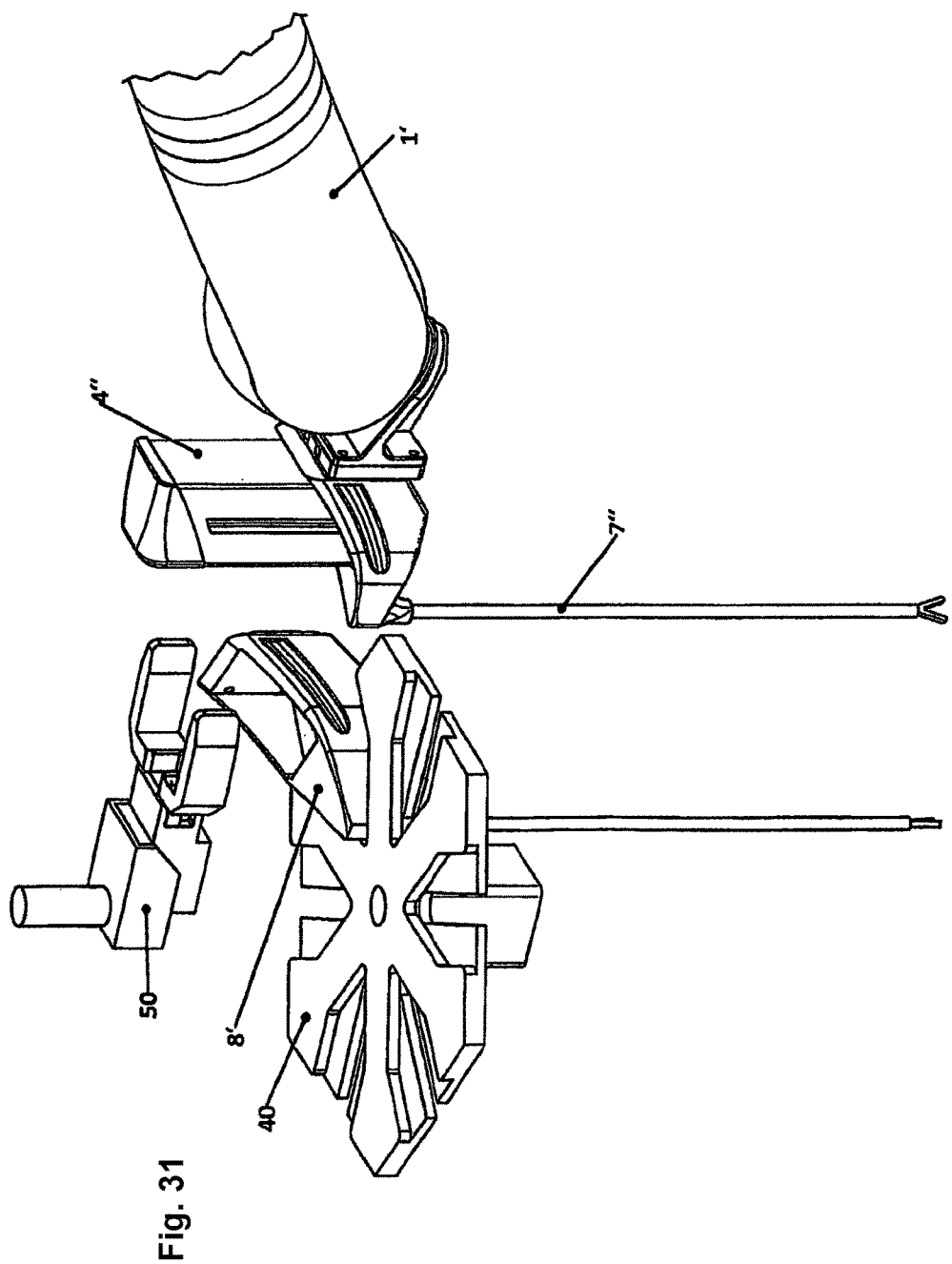
FIG. 31: a surgical robot system according to one embodiment of the present invention with an instrument magazine.

FIG. 31 shows a surgical robot system according to one embodiment of the present invention with an instrument magazine for selective storage of instruments of the instrument assembly, as was explained previously with reference to FIGS. 26 through 30.

In the instrument magazine 40, prepared instruments, particularly with drive units inserted, can be stored under sterile conditions prior to use and likewise be supplied with power. Besides power supply, there also optionally exists a communication link between the drive units not mounted to the robot and an (instrument) control of the robot assembly (not shown). The instrument magazine can be configured as a sterilizable unit and/or be enclosed in a sterile shell, which can be advantageously made as a single-use item. The instrument magazine can in particular have two or more accommodation shells for individual or multiple instrument shafts 7'', 8' and/or drive units. The individual drive units are positioned at the located provided for them by the accommodation shells and the electrical contacts or other, particularly wireless, power and/or data transmission units are correctly positioned relative to one another. Likewise, the instrument magazine can also be configured, particularly plate-like, for free storage of instrument shafts and/or drive units, i.e. not, or only optionally, provided with dedicated accommodation shells. This embodiment is particularly suited for drive units with wireless power and data transmission, wherein the power and/or data transmission units of the instrument magazine can be arranged in a grid, so that arbitrary storage locations for the drive units are possible. In this solution, easier cleaning and sterile covering in particular are advantageous.

To fasten an instrument or a drive unit to a robot, it is removed from the sterile instrument magazine. To maintain power supply to at least the signal processing electronics of this drive unit for the period following removal from the instrument magazine until mounting on a robot, to prevent repeating booting and initialization following mounting on a manipulator arm, the drive unit has an energy storage unit, so that autonomous power supply of at least the signal processing electronics is possible. This energy storage unit is located, in one embodiment, in the modular drive unit and/or can be regenerated or recharged upon connection to an external power supply, particularly on the robot or in the instrument magazine. Simple operation and service by OR personnel is thus possible. Likewise, the drive unit can also be supplied with power by the energy storage unit for the entire duration of an intervention. Another alternative consists of a sterile cable connection between the robot assembly and the mounted and/or un-mounted instruments or instruments fastened to the robot assembly or drive units for power supply and/or data exchange. In another embodiment, wireless power transmission to drive units can be provided, which can allow a distinctly increased mobility of drive units and instruments compared in particular to cable-connected systems. Advantageous compared to supply by an energy storage unit are the smaller size and the lower weight of the drive units. All electrical contacts can be dispensed with, whereby sterile shells can be made distinctly simpler and more cost-effective. Due to the elimination of sterile electrical contacts, the preparation of the instruments or drive units is also simplified.

In one embodiment, particularly for increasing operating safety of drive units with wireless power and/or communication links, an additional communication channel independent of the intrinsic communication channel can be provided for status reporting. This additional communication channel preferably operates according to a physical principle different from the intrinsic communication channel, optically for example. It preferably does not serve for transmitting large quantities of data, but rather only for exchanging status reports between a robot and a drive unit mounted thereon. The additional communication channel runs preferably in parallel to the intrinsic data connection. It can operate on the de-energize-to-trip principle, so that an emergency disconnection of at least the effected robot and the affected drive unit can be initiated as soon as the connection is broken or the status of the robot or the instrument or drive unit changes.

With reference to the figure series of FIGS. 32A-32D, 33A-33D, method steps of a method for, particularly selectively, equipping a robot assembly of a surgical robot system with an instrument and an instrument with a drive unit according to one embodiment of the present invention is explained in more detail hereafter.

Registration of an instrument shaft coupled to a drive unit can occur automatically. In the process, one or more of the following steps preferably occur following establishment of a mechanical connection between the instrument shaft and the drive unit:

1) Coupling with an instrument shaft is detected and a registration procedure for concretely defining the attached instrument is activated;
2) The instrument or the instrument shaft can identify itself, particularly through active communication between the drive unit and a controller integrated into the instrument shaft, preferably a microcontroller. Alternatively, a coupled instrument can be identified, particularly by means of a non-volatile memory chip, an EEPROM for example, in the instrument, the information being available for query from the drive unit.

An instrument or instrument shaft preferably contains one or more of the following data: identification code, instrument name, serial number, number of remaining or still available uses, calibration parameters for compensating manufacturing and assembly tolerances and/or kinematic and/or dynamic parameters which characterize and instrument type, for example weight, center of gravity location, inertia sensor, origin and orientation of the end effector coordinate system, kinematic-specific transformation matrices, joint angle limits and Cartesian working space.

After successful registration, the drive-unit-equipped instrument of the robot assembly is known, so that one or more of the following steps can be carried out:

3.1) Passing on the instrument data to the instrument control of the robot assembly and/or a control layer of the drive unit, particularly an electronic part. This can preferably be accomplished as early as upon connection of the instrument shaft and the operating unit, particularly in the instrument magazine, or only upon connection with the robot. If for example a decentralized current control of the drive unit is implemented within it, a position control centrally in the instrument control of the robot assembly, the drive unit can function as a gateway and retransmit all instrument data to the instrument control, via a fieldbus for example.
3.2) Status changes of the drive unit after confirmation by the instrument control, particularly signalling the status to an operator.

All registered instruments can be stored in a database, which can be continuously updated during an intervention. This informational connection of all instruments or drive unit—not only those mounted on or attached to the robot assembly—to the instrument control of the robot assembly offers some advantages, both for control of the robot assembly and for the user: the operator has at all times an overview of the instruments currently ready for service and their status; the operational state, for example "ready for operation," (various) error conditions, elapsed lifetime and the like of each instrument or each drive unit can be signalled to the OP personnel. This can be accomplished acoustically or optically for example, by means of one or more mono- or polychromatic signal lights, particularly LEDs, particularly on the drive unit. Similarly, the operational states of all or individual instruments or drive units can be signalled to the operator at an input console by suitable overlays.

During an instrument change, the operator can select at an input console a registered instrument to be exchanged, as well as the robot on which the selected instrument is to be mounted. This information can be used to support a manual instrument change and to make it easier for the OR personnel, or to initiate an automatic instrument change.

In one embodiment, one or more robots of the robot assembly and/or one or more instruments and/or drive units of the instrument assembly have available a signal device, for example a, particularly polychromatic, signal light. In preparation for an instrument change, the signal light of the affected robot is activated in a particular colour and/or a particular blink sequence. The OR personnel are thereby clearly notified of which robot(s) is (are) affected by the impending instrument change. Likewise, the signal light of the instrument to be exchanged is activated in a particular colour and/or a particular blink sequence, so as to clearly indicate to the OR personnel, which instrument is to be exchanged. Likewise, a successful instrument change can be indicated to the OR personnel by a special colour or blink pattern of the signal lights on the manipulator arm and the instrument. Alternatively or in addition to optical signalling, an acoustic signal is also possible.

FIGS. 32A-32D, 33A-33D show a method according to the invention for automatic instrument exchange or equipping a robot assembly with an instrument of the instrument assembly, and an instrument with a drive unit. To this end, the surgical robot system has an instrument exchange magazine wherein all required instruments are stored ready for use and are kept in readiness. All instruments are stored in the exchange magazine without a drive unit, as the application of the drive unit to an instrument occurs during the exchange procedure. For this purpose, the exchange magazine has available a drive unit manipulator 50 (see FIG. 31) for handling the drive units during instrument exchange. The drive unit manipulator has, in one embodiment, no degrees of freedom of its own, with the exception of a tensioning mechanism for the drive unit; all positioning movements are carried out by the robot. For example, a drive unit can, with the help of this drive unit manipulator, be separated from one instrument and connected with another. The number of drive units can thereby be reduced, as not every instrument present in the exchange magazine need be equipped with a drive unit. Besides, this concept allows less expenditure for power supply to the drive units, as no power supply is required to the instruments stored in the exchange magazine. Power supply of the drive units need only be provided for the period wherein they are not mounted on a robot and supplied with power from there. Power supply to the drive unit during this period can, in one embodiment, be accomplished through the drive unit manipulator.

A rotary instrument exchange magazine is shown in FIGS. 31, 32A-32D. A linear instrument exchange magazine can likewise be used. In order to be able to handle various drive units, the drive unit manipulator can optionally be equipped with a plurality of grips, which can have different configurations. In this case, the drive unit manipulator preferably has one or more translational and/or one or more rotary motion options, so as to handle the required drive unit.

Figure 32A:
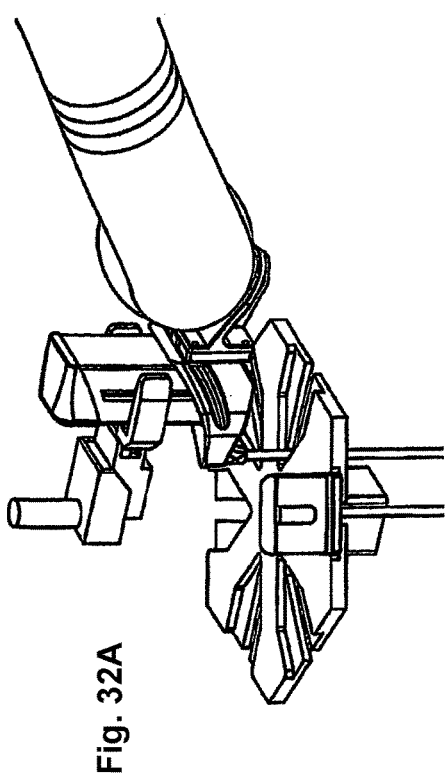
FIGS. 32A-32D, 33A-33D: a method according to the invention for automatically equipping a robot assembly with an instrument of the instrument assembly and an instrument of this instrument assembly with a drive unit according to one embodiment of the present invention.
Figure 32B:
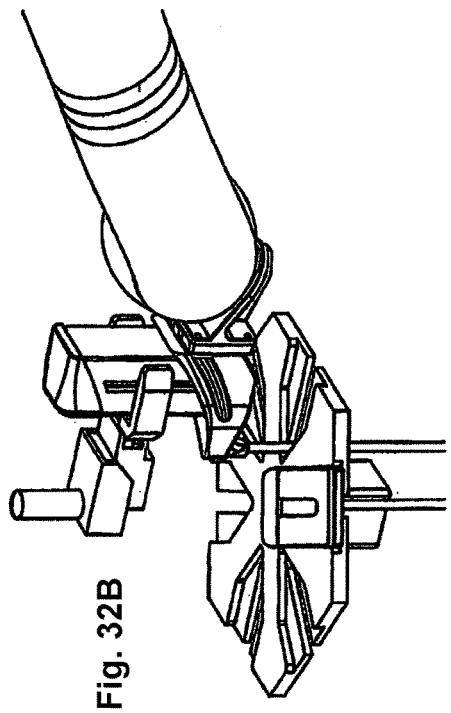
Figure 32C:
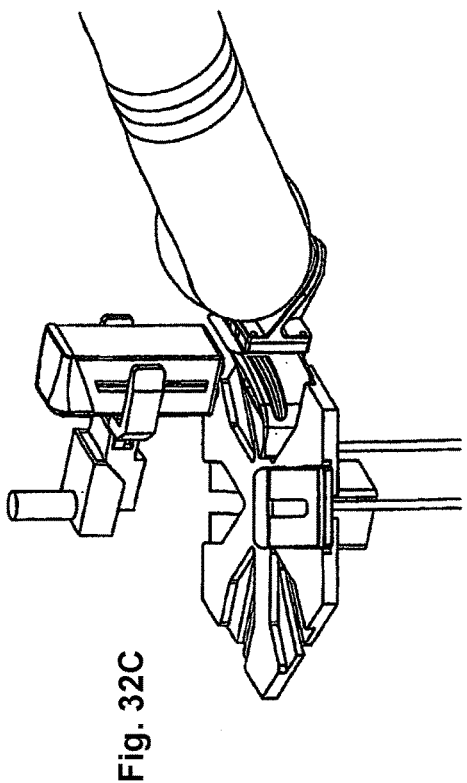
Figure 32D:
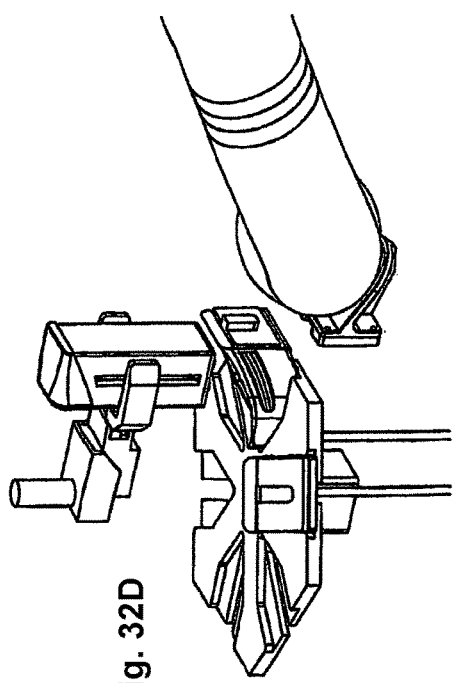

FIGS. 32A-32D show steps in stowing an instrument in the instrument exchange magazine, as they can occur in particular during an automatic tool exchange. First, the robot is moved out of the operating area to the tool magazine in the output position for instrument storage (FIG. 32A). Then the drive unit is mounted or fastened onto the drive unit manipulator, shown for example in FIG. 32B as a two-jaw gripper. If necessary, an attachment between the drive unit and the instrument is released. Optionally, maintenance of power supply to the drive unit occurs, particularly by contact or contactless, perhaps through the drive unit manipulator. Then the instrument shaft is stored in the exchange magazine (FIG. 32C), the connection between it and the drive unit manipulator being released. Finally, the robot moves away from the exchange magazine, the connection between the instrument shaft and the robot being released thereby or beforehand (FIG. 32D).

Figure 33A:
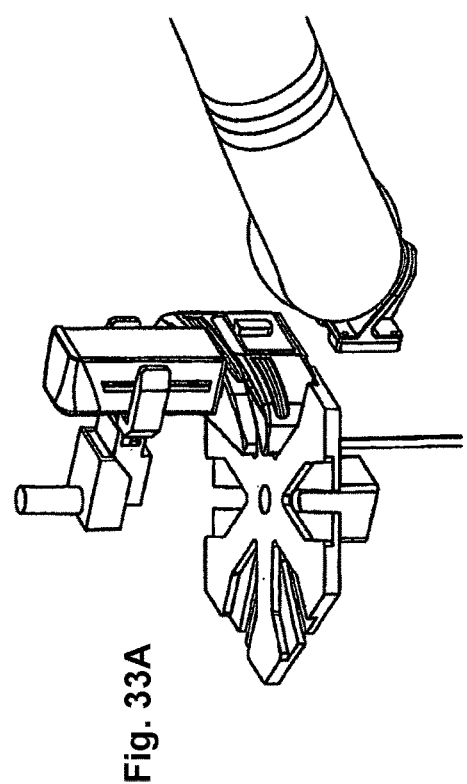
Figure 33B:
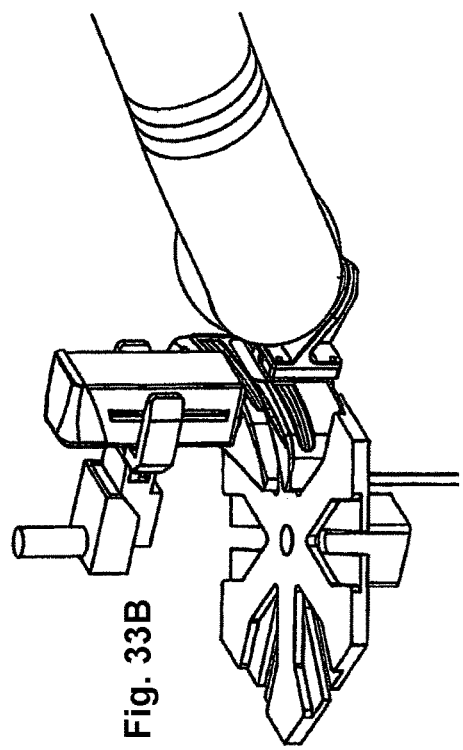
Figure 33C:
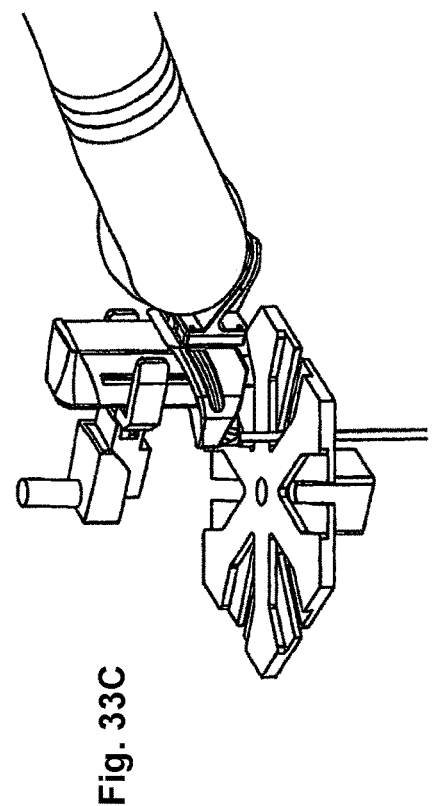
Figure 33D:
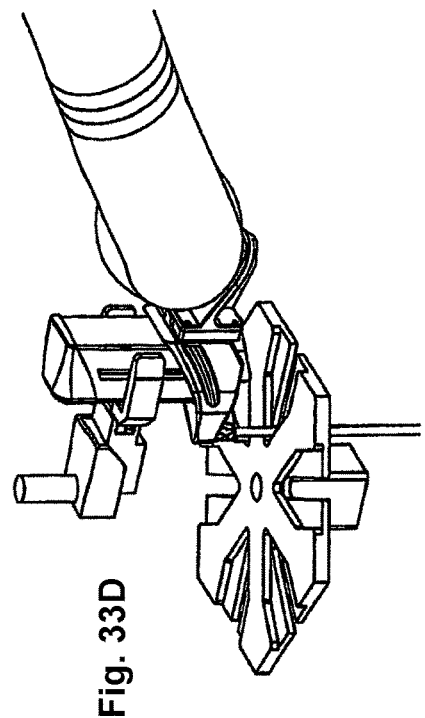

FIGS. 33A-33D show steps for reception of an instrument from the exchange magazine by a robot: first, the instrument to be exchanged is made ready by operation of the instrument exchange magazine, the drive unit being placed in the correct position by the drive unit manipulator (FIG. 33A). Then the instrument shaft is mounted on the robot (FIG. 33B), which transports it to the drive unit mounted on the drive unit manipulator, where it is adapted or mounted on the instrument shaft (FIG. 33C). The attachment of the drive unit in the drive unit manipulator is released. Thereafter, the substituted instrument-drive unit is ready for use (FIG. 33D) and can be operated under robot control.

It is noted that in these method steps, synergistically, the robot assembly on the one hand is selectively equipped with an instrument (see in particular FIG. 32C, FIG. 32D, stowing a robot-controlled instrument; FIG. 33B, reception of a robot-controlled instrument by a robot), and on the other hand a robot-controlled instrument stored in an instrument magazine is selectively equipped with a drive unit (see in particular FIGS. 32B, 32C, separation of the drive unit; FIGS. 33B, 33C, attachment of the drive unit to the instrument shaft).

REFERENCE SYMBOL LIST

In FIGS. 1 Through 14
1 instrument
2 instrument housing
3 instrument shaft
4 drive unit
5 seal
6,7 attachment means/elements
8,19 sterile barrier
9,10 individual drives
11,12 coupling elements
13,14 traction cables
15-18 pulleys
101 instrument
102 instrument housing
103 instrument shaft
104 drive unit
105 seal
106,107 attachment means/elements
109,110 individual drives
111,112 coupling elements
113,114 traction cables
115-118 pulleys
119 sterile barrier
201 robot/manipulator arm
202 proximal base
203 distal end
204 sterile shell
205 instrument
206 instrument housing
207 instrument kinematics
208 surgical end effector
209 instrument shaft
210 instrument adapter
211 sterile barrier
212 drive unit
213 seal cover
214 contact pin
215 socket
216 recess 217 radial protuberance
601 sterile protection
701 rigid intermediate plate
702 side of the rigid intermediate plate
703 facing side of the rigid intermediate plate
704 circumferential surface
705 motion transmission element
706 eversion
707 elastic membrane
801-803 drive unit
805a-805d, 807a-807e, 809a-809d individual drives
804a-804c housing
806,808,810 mechanical coding
901 instrument
902 drive unit housing part
903 drive unit housing part
904 instrument shaft
905 adapter
906,907 coupling element
908,909 traction cables
910-913 pulleys
914 drive unit
915 housing
916 seal cover
917 attachment means/elements
918,919 individual drives
920 sterile barrier
921,922 motion transmission element
1101-1103 manipulator arm
1104-1106 surgical instrument
1107-1109 instrument shaft
1110-1112 penetration point
1113 abdominal wall
1114 operation area
1115 minimum spacing
In FIGS. 15 Through 25
1A, 1B power take-off shaft of an actuator of an actuator assembly
2A,2B position sensor (electronic component)
3 housing
3.1 penetration openings
3.2 housing vessel (housing part)
3.3 housing cover (housing part)
3.4 housing wall
4; 4.1, 4.2 thermal insulation layer
5 thermal insulation layer
6; stationary heat conduction means
6.1 heat dissipation surface
6.2 heat absorption surface
7 movable element (switchable heat conduction means)
8.1; 9.1 gap
8.2; 9.2 movable element (switchable heat conduction means)
8.3; 9.3 shell
9.4 heat collection means
10 Peltier element (switchable heat conduction means)
10.1 heat dissipation surface
11 working fluid passage (switchable heat conduction means)
11.2 heat absorption surface
12 heat pipe (switchable heat conduction means)
12.1 heat dissipation surface
12.2 heat absorption surface
100 shell
In FIGS. 26 Through 33
1; 1',2, 3 robot assembly
4; 4'; 4",5, 6 modular drive unit 7; 7'; 7", 8; 8', 9 instrument shaft
7.1; 7A' flange
7.2 drive train
10,11,12 opening
13 abdominal wall
14 operation area
20 electronic module (drive unit)
20.1; 20.2, 22.2 interface
21 drive module (drive unit)
22 instrument adapter
24 sterile shell
30 base (operating unit)
31 hand lever (operating unit)
40 instrument magazine
50 drive unit manipulator

The invention claimed is:

1. An instrument assembly for a surgical robot system that includes at least one robotic manipulator, the instrument assembly comprising:
at least one instrument with at least one instrument shaft configured for partial insertion into a patient;
a drive train assembly with at least one drive train for actuating a degree of freedom of an end effector of the instrument shaft;
at least one modular drive unit for actuating the drive train assembly, whereby the degree of freedom of the end effector is actuated; and
an instrument housing, comprising:
at least one drive train housing part on which at least a part of the drive train assembly is located, and
at least one drive unit housing part with a hollow space which is configured for accommodating the drive unit, the drive unit housing part having a seal for sealing an insertion opening of the hollow space under sterile conditions and a dynamic sterile barrier, which isolates the hollow space under sterile conditions and through which the drive train assembly can be actuated;
wherein the drive unit is laterally offset with respect to a longitudinal axis of the instrument shaft in a direction toward a connection of the instrument housing with a robot of the surgical robot system.

2. The instrument assembly of claim 1, wherein the drive train housing part and the drive unit housing part are one of:
separably interconnected,
permanently interconnected, or
made integrally with one another.

3. The instrument assembly of claim 2, wherein at least two drive train housing parts or drive unit housing parts are configured for selective connection with the other of the drive train housing parts or drive unit housing parts.

4. The instrument assembly of claim 1, comprising at least two modular drive units or at least two drive unit housing parts with differing encodings.

5. The instrument assembly of claim 4, wherein the at least two modular drive units or at least two drive unit housing parts have different mechanical encodings.

6. The instrument assembly of claim 1, wherein the dynamic sterile barrier is one of separably or permanently connected with the drive unit housing part.

7. The instrument assembly of claim 1, further comprising an electromechanical interface for separably connecting the instrument housing to the robot assembly.

8. The instrument assembly of claim 7, wherein the electromechanical interface separably connects the drive train housing part to the robot assembly.

9. The instrument assembly of claim 7, wherein the electromechanical interface is connected with at least one of the instrument housing or the robot assembly by a mechanical plug connection.

10. The instrument assembly of claim 9, wherein the mechanical plug connection perforates a static sterile barrier.

11. The instrument assembly of claim 1, further comprising structure attaching the drive unit inside the hollow space.

12. The instrument assembly of claim 11, wherein the structure attaching the drive unit inside the hollow space is configured for at least one of tensioning, interlocking, or fixed attachment.

13. The instrument assembly of claim 1, wherein the insertion opening is located on an end face that faces toward or away from the instrument shaft, or is located on a lateral surface of the instrument housing.

14. A method for assembling an instrument assembly for use with a surgical robot system, the method comprising:
   obtaining an instrument assembly according to claim 1;
   covering the surroundings of the insertion opening in a sterile manner;
   inserting the drive unit into the hollow space of the drive unit housing part; and
   sealing the seal in a sterile manner.

15. A method for assembling a surgical robot system that includes a robot assembly having at least one robot, and an instrument assembly including at least one instrument according to claim 1, wherein the instrument is controlled by the robot, the method comprising:
   sterile packing of at least one of the robot assembly or at least one drive unit of the instrument assembly into a drive unit housing part;
   establishing a mechanical plug connection of an electromechanical interface between the robot assembly and the instrument assembly;
   perforating a static sterile barrier of at least one of the robot assembly or of the instrument housing, guided by the mechanical plug connection; and
   fastening the electromechanical interface.

16. An instrument assembly for a surgical robot system having at least one robotic manipulator, the instrument assembly comprising:
   at least one instrument with an instrument housing, and an instrument shaft configured for partial insertion into a patient;
   a drive assembly with at least one drive train for actuating a degree of freedom of an end effector of the instrument shaft; and
   a drive unit for actuating the drive train such that the degree of freedom of the end effector is actuated, the drive unit laterally offset with respect to a longitudinal axis of the instrument shaft in a direction toward a connection of the instrument housing with the robotic manipulator.

17. The instrument assembly of claim 16, comprising an instrument housing which tapers laterally with respect to the longitudinal axis of the instrument shaft.

18. A surgical robot system, comprising:
   a robot assembly with at least one robotic manipulator, and
   an instrument assembly according to claim 16, with at least one instrument controlled by the robot assembly.

* * * * *